(12) United States Patent
Beauchesne et al.

(10) Patent No.: US 12,088,600 B1
(45) Date of Patent: Sep. 10, 2024

(54) MACHINE LEARNING SYSTEM FOR DETECTING ANOMALIES IN HUNT DATA

(71) Applicant: Rapid7, Inc., Boston, MA (US)

(72) Inventors: Jocelyn Beauchesne, Saint-Lormel (FR); John Lim Oh, Mukilteo, WA (US); Vasudha Shivamoggi, Cambridge, MA (US); Roy Donald Hodgman, Cambridge, MA (US)

(73) Assignee: Rapid7, Inc., Boston, MA (US)

( * ) Notice: Subject to any disclaimer, the term of this patent is extended or adjusted under 35 U.S.C. 154(b) by 215 days.

(21) Appl. No.: 17/024,481

(22) Filed: Sep. 17, 2020

Related U.S. Application Data

(60) Provisional application No. 62/901,991, filed on Sep. 18, 2019.

(51) Int. Cl.
*H04L 9/00* (2022.01)
*G06N 20/00* (2019.01)
*G16B 40/30* (2019.01)
*H04L 9/40* (2022.01)

(52) U.S. Cl.
CPC ......... *H04L 63/1416* (2013.01); *G06N 20/00* (2019.01); *G16B 40/30* (2019.02); *H04L 63/0823* (2013.01)

(58) Field of Classification Search
None
See application file for complete search history.

(56) References Cited

U.S. PATENT DOCUMENTS

| | | | |
|---|---|---|---|
| 7,689,455 B2 | 3/2010 | Fligler et al. | |
| 7,698,071 B2 | 4/2010 | Harris | |
| 8,838,511 B2 | 9/2014 | Kristal et al. | |
| 8,948,540 B2 | 2/2015 | Robinson et al. | |
| 9,210,181 B1 | 12/2015 | Nandy et al. | |
| 9,843,596 B1 | 12/2017 | Averbuch et al. | |
| 9,906,405 B2 | 2/2018 | Mankovskii | |

(Continued)

OTHER PUBLICATIONS

Jonathon Shlens, "A Tutorial on Principal Component Analysis", dated Apr. 3, 2014, pp. 1-12.

(Continued)

*Primary Examiner* — Daniel B Potratz
*Assistant Examiner* — Syed M Ahsan
(74) *Attorney, Agent, or Firm* — Ashwin Anand; Lei Sun

(57) ABSTRACT

An anomaly detection system is disclosed capable of reporting anomalous processes or hosts in a computer network using machine learning models trained using unsupervised training techniques. In embodiments, the system assigns observed processes to a set of process categories based on the file system path of the program executed by the process. The system extracts a feature vector for each process or host from the observation records and applies the machine learning models to the feature vectors to determine an outlier metric each process or host. The processes or hosts with the highest outlier metrics are reported as detected anomalies to be further examined by security analysts. In embodiments, the machine learnings models may be periodically retrained based on new observation records using unsupervised machine learning techniques. Accordingly, the system allows the models to learn from newly observed data without requiring the new data to be manually labeled by humans.

20 Claims, 29 Drawing Sheets

(56) References Cited

U.S. PATENT DOCUMENTS

| | | | |
|---|---|---|---|
| 9,910,941 | B2 | 3/2018 | Dusanapudi et al. |
| 10,235,601 | B1 | 3/2019 | Wrenninge et al. |
| 10,270,788 | B2 | 4/2019 | Faigon et al. |
| 10,311,368 | B2 | 6/2019 | Lokare et al. |
| 10,372,910 | B2 | 8/2019 | Martin et al. |
| 10,599,957 | B2 | 3/2020 | Walters et al. |
| 10,645,601 | B2 | 5/2020 | Kleinbeck et al. |
| 10,743,778 | B2 | 8/2020 | Zuckerman-Stark et al. |
| 10,846,188 | B2 | 11/2020 | Tien et al. |
| 11,348,034 | B1 | 5/2022 | Jain et al. |
| 11,399,039 | B2 | 7/2022 | Rubin et al. |
| 2006/0230451 | A1* | 10/2006 | Kramer .............. G06F 21/56 726/22 |
| 2012/0030731 | A1* | 2/2012 | Bhargava .............. H04L 63/10 726/3 |
| 2015/0341376 | A1 | 11/2015 | Nandy et al. |
| 2016/0036837 | A1 | 2/2016 | Jain et al. |
| 2016/0078361 | A1 | 3/2016 | Brueckner et al. |
| 2017/0063907 | A1 | 3/2017 | Muddu et al. |
| 2017/0353477 | A1* | 12/2017 | Faigon .............. H04L 63/1416 |
| 2018/0096261 | A1 | 4/2018 | Chu et al. |
| 2018/0153495 | A1 | 6/2018 | Itu et al. |
| 2018/0248904 | A1* | 8/2018 | Villella .............. G06N 3/047 |
| 2018/0319015 | A1 | 11/2018 | Sinyavskiy et al. |
| 2019/0124045 | A1 | 4/2019 | Zong et al. |
| 2019/0215329 | A1 | 7/2019 | Levy |
| 2020/0125734 | A1 | 4/2020 | Light et al. |
| 2020/0379868 | A1* | 12/2020 | Dherange .............. G06N 20/20 |
| 2022/0038332 | A1 | 2/2022 | Umakanth et al. |
| 2022/0207434 | A1 | 6/2022 | Xue et al. |

OTHER PUBLICATIONS

Nicolas Gillis, "Why and How Nonnegative Matrix Factorization", dated Mar. 7, 2014, pp. 1-25.

Zhongyuan Zhang et al, "Binary Matrix Factorization with Applications", pp. 1-10,.

Seokho Lee et al, "Sparse Logistic Prinipal Components Analysis for Binary Data", dated Jan. 2009-2010, pp. 1-23.

Emmanuel J. Candes et al, "Robust Principal Component Analysis", dated Dec. 17, 2009, pp. 1-39.

Haozhe Xie et al, "A Survey of Dimensionality Reduction Techniques Based on Random Projection", dated May 30, 2018, pp. 1-10.

Utkarsh Porwal et al, "Credit Card Fraud Detection in e-Commerce: An Outlier Detection Approach", dated May 7, 2019, pp. 1-10.

Larry M. Manevitz et al, One-Class SVMs for Document Classification, dated 2001, pp. 1-16.

Tianqi Chen et al, "XGBoost: A Scalable Tree Boosting System", dated Jun. 10, 2016, pp. 1-13.

Jasper Snoek et al, "Practical Bayesian Optimization of Machine Learning Algorithms" pp. 1-9.

Eric Brochu et al, "A Tutorial on Bayesian Optimization of Expensive Cost Functions with Application to Active User Modeling and Hierarchical Reinforcement Learning", dated Dec. 14, 2010, pp. 1-49.

Xian Wu et al, "Local Density Estimation in High Dimensions", dated Sep. 20, 2018, pp. 1-45.

Han Liu et al, "Sparse Nonparametric Density Estimation in High Dimensions Using the Rodeo", pp. 1-8.

* cited by examiner

Approach to Find Ideal # of Dimensions

Brute force analysis on existing leaves:
- Leave out one column
- Reduce size of dataset to k in [1, 100]
- Train logistic regression to predict left out column
- Check AUC
- Iterate across all columns Predict optimal k to reach maximum AUC using Random Forest (MSE 0.25 on testing set)

MACHINE LEARNING SYSTEM FOR DETECTING ANOMALIES IN HUNT DATA

This application claims benefit of priority to U.S. Provisional Application No. 62/901,991, filed Sep. 18, 2019, titled "Unsupervised Anomaly Detection Pipeline," which is hereby incorporated by reference in its entirety.

TECHNICAL FIELD

This disclosure is related to cybersecurity computing systems. In particular, this disclosure is related to anomaly detection using machine learning models in managed detection and response (MDR) scenarios of cybersecurity computing environments.

BACKGROUND

In 2016, UBER reported that hackers stole the information of over 57 million riders and drivers. In 2017, 147.9 million consumers were affected by the EQUIFAX breach. In 2018, UNDER ARMOUR reported that its "My Fitness Pal" service was hacked, affecting 150 million users. By 2021, damages related to cybercrime is projected to hit 6 trillion dollars. As the world becomes increasingly digital, the threat of cyberattacks looms large. On a regular basis, reports surface of cyberattacks by ill-intentioned individuals or groups to obtain proprietary data and resources from companies that can be leveraged for significant profit. As a result, the cybersecurity industry has recently seen dramatic growth in the demand for third-party network monitoring and data analytics services to guard company networks against cyberattacks.

A Managed Detection and Response (MDR) service is a service that relies on the expertise of security analysts to scour metadata about a computer network to detect and respond to cyberattacks. The MDR service works by collecting large volumes of data about computers on a client network and presenting the data to cybersecurity experts to be examined for signals indicating compromise of the computers, in process is called a "hunt." However, because the hunt process relies heavily on manual data analysis, it can be extremely slow, tedious, and error-prone. Moreover, human analysts are not always sensitive to subtle patterns in the data and cannot easily identify events associated with novel types of attacks, causing some attacks to escape detection in many cases. Better techniques are needed to improve the performance and effectiveness of the hunt process, and to reduce the amount of human analysis needed for hunts.

SUMMARY OF EMBODIMENTS

Disclosed herein are methods, systems, and processes for implementing a machine learning anomaly detection system capable of detecting anomalies (e.g. outlier processes or hosts) in hunt data gathered from a computer network. Embodiments of the anomaly detection system implement a detection pipeline comprising multiple stages, including pre-processing (e.g. feature engineering), dimensionality reduction, anomaly scoring using machine learning algorithms, and an interpretability layer. In some embodiments, the pipeline employs machine learning models that can be trained in an unsupervised manner. Accordingly, the pipeline allows the models to gradually learn from newly observed data without requiring the new data to be manually labeled. In some embodiments, the anomaly detection system will report a set number of the most anomalous processes or hosts during each observation period (e.g. determined based on a ranking of an outlier metric). Accordingly, the system is designed to surface only a small set of anomalies for each observation period, so that security analysts will not be flooded with a large volume of alerts.

Figure 1A:
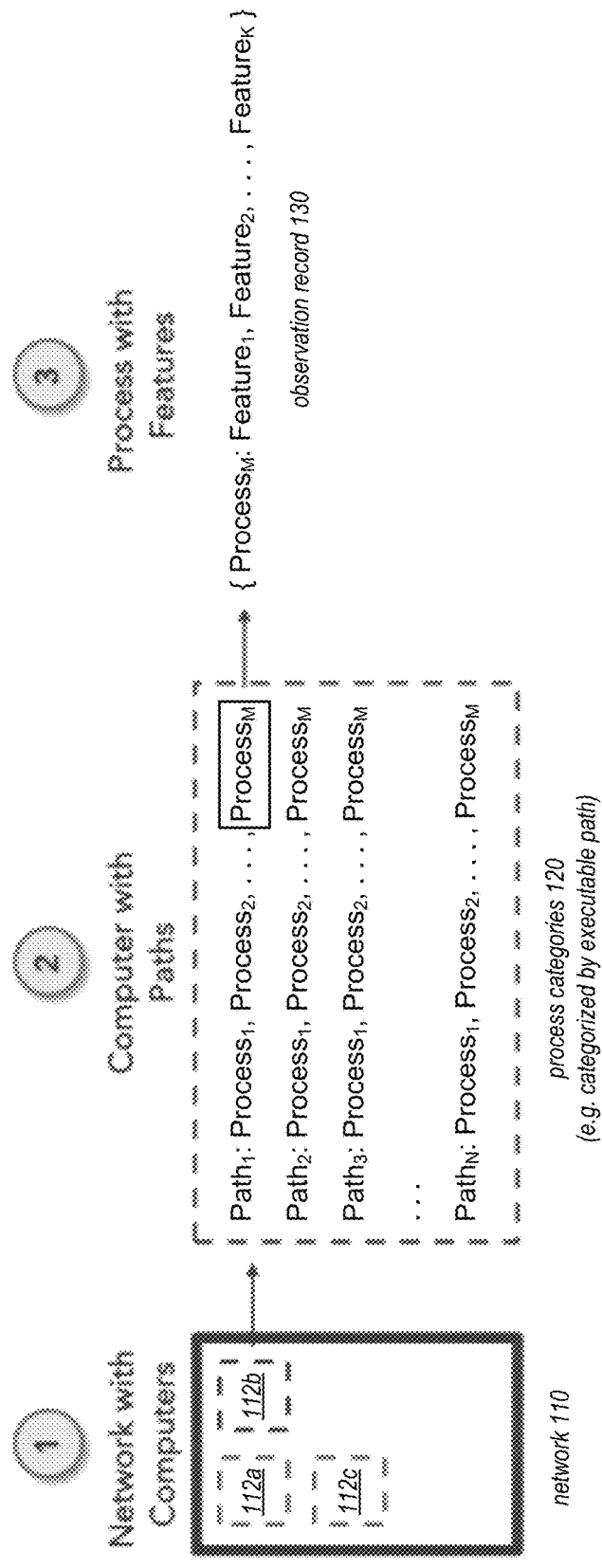
FIGS. 1A and 1B depict a block diagram 100 illustrating a tree structure used to contextualize hunt data in a machine learning anomaly detection system, according to some embodiments.

While the disclosure is open to various modifications and alternative implementations, specific embodiments of the disclosure are provided as examples in the drawings and detailed description. It should be understood that the drawings and detailed description are not intended to limit the disclosure to the particular form disclosed.

DETAILED DESCRIPTION

1. Introduction

A Managed Detection and Response (MDR) service is a service that relies on the expertise of security analysts to scour data about a computer network to extract insights about the behavior of the network. The MDR service typically works by collecting large volumes of data about computers on a client network and presenting the data to cybersecurity experts to be examined for small signals indicating compromise of the computers. This process is called a "hunt." The hunt process relies on manual analysis of a large amount of data. For example, cybersecurity technologies companies that provide MDR services such as RAPID7 of Boston, MA may collect upwards of 40 terabytes of raw hunt data over just one year.

The massive amount of hunt data poses significant challenges for cybersecurity companies that offer MDR services. Firstly, the daunting amount of data impacts the speed at which clients can find out about cyberattacks and potential breaches, exacerbating the impact to their business and their clients. Secondly, security analysts in a Security Operations Center (SOC) are having to spend a significant amount of time on mechanical tasks to manage the collected data (e.g., formatting the data) to perform a hunt, thus leaving them less time to work on higher impact tasks (e.g., running investigations based on quirks in the data). Lastly, there is little room to scale this largely manual process to consume more data or take on additional clients.

To address these and other problems of the state of the art, embodiments of a machine learning pipeline system are disclosed herein to detect outlier events in collected data of computer networks. The system improves upon conventional MDR systems by using machine learning (ML) techniques to improve the speed and efficiency of processing large amounts of data and prioritizing the investigations analysts should perform. The system allows security analysts to better utilize their time and expertise to focus on the suspicious outlier events detected by the system, and drastically reduces the amount of time it takes to detect an attack or compromise, thus minimizing the chances of potentially crippling outcomes.

Machine learning in an MDR setting is faced with a host of technology-related challenges, including the following. First, due to the manual nature of the MDR review process and the rarity of actual attacks or breaches, there is little or no labeled data, making it difficult to develop high quality anomaly detection models. Second, information about the behavior of computers in networks is particularly complex, and the observation data for hunts have extremely high dimensionality. Third, the signals for cyberattacks can evolve very quickly, as hackers can be extremely creative in devising variations of old attack methods to evade detection.

In short, security analysts are faced with the difficult task of looking for a rare signal of an attack or compromise that they are not sure exists. Worse, the analysts are not even sure what an actual signal might look like. It is a needle in the haystack problem, where the needle may not be a needle and it may or may not exist. Moreover, because the amount of data collected for a hunt can be overwhelming, it can be a challenge to filter out the noise in the data. The sheer volume of hunt data also makes the hunt process difficult to scale (e.g. to very large networks).

Accordingly, in order to address all of the aforementioned issues, the machine learning anomaly detection system disclosed herein implements a scalable yet highly granular system that is capable of detecting outliers and quantifying the associated level of risk of the outliner events. As discussed in detail below, the disclosed system provides security analysts a natural way to prioritize their work by programmatically identifying anomalies in a computer network that are indicative of threats to be examined by the hunt process.

2. Data and Natural Tree Structure

2.1 Hunt Data

As shown in FIG. 1A, an embodiment of the anomaly detection system may be used to collect hunt data from a network 110 of computers (computers 112a-c). Client data for a hunt process can include upwards of 40 TB of compressed data. Further breaking this down, this represents an average of 10 to 30 GB per client per month (e.g., collected over the course of a year). In some embodiments, hunt data may also include data collected from ancillary data sources (e.g., reports of known malicious activities published by companies such as REVERSINGLABS).

In some embodiments, the data retrieved by a MDR service may include data about processes that were executed on a computer. The process data may be captured in a process log and uploaded by a data collection agent to the anomaly detection system. In some embodiments, the anomaly detection system may perform pre-processing on the collected data to group the processes into a set of process categories 120. Each process category may include a set of processes that are expected to have similar execution behaviors. As shown in this example, the processes are grouped according to the file system path of the executable that was executed by the process. In some embodiments, the file system path may be normalized to remove undesired information for categorization purposes, such as a version number of the executable, or a drive letter assigned to the root of the path. In other embodiments, other types of process attributes or features may be used to group processes into categories. For example, processes may be grouped according to their executable MD5, the user who launched the process, or the time that the process was launched, etc., or some combination of such features or attributes.

In some embodiments, a process record (e.g. observation record 130) retrieved by a MDR service may include various features of a process. These features may be used to construct an input feature vector for consumption by various machine learning models of the anomaly detection system. Depending on the embodiment, these process features may include some or all of the following: (1) the command line used to launch the process on the host, including any specific options; (2) signing details or certificate used to sign the executable executed by the process by its editor to prove where it comes from, which is helpful to assess the authenticity of a software; (3) a digital fingerprint (e.g. a Message Digest 5 (MD5) value computed from the executable, which is specific to the contents of the binary file (e.g., a single change in one bit in the file leads to an entirely different string); (4) network information about the process such as Internet Protocol (IP) addresses the host or process connected to and how; and (5) information about modules that were dynamically loaded the process, including (a) the file system path of the dynamic link library (DLL) loaded, (b) the digital fingerprint or MD5 of the DLL, and (c) the name of the DLL.

In some embodiments, other types of process attributes or features may also be included in the process record 130 and used for anomaly detection. Depending on the embodiment, other process attributes or features may include the time (e.g. time of the day) when the process was launched, the length of time that the process executed, the amount of resources used by the process (e.g. CPU, memory, network, or storage usage), the identity and/or type of host that executed the process, the identity and/or type of user who initiated the process, the execution mode of the process, the termination status of the process (e.g. whether the process terminated due to an unexpected error), information about any files accessed by the process, and information about the parent process or any child process that are initiated by the process, among many others.

In some embodiments, the raw observation record 130 of a process may be encoded as a document during at least the pre-processing stage of the anomaly detection pipeline. In some embodiments, the observation record may be encoded in a bag-of-words representation, where individual attributes or features of the process are represented as distinct terms seen in the document.

2.2 Tree Structure

In some embodiments, for a specific computer program (e.g., a software program) executing on a computing device, typical program behaviors are mined using machine learning. For example, if a software program or software application is used in a malicious manner, the behavior of the program or application will deviate from baseline behaviors (e.g. the behavior of previous processes in the same process category).

In some embodiments, processes are aggregated or categorized based on the file system path of the executables across hosts and across hunts. This categorization of processes is used to at least: (1) contextualize each process to other processes that are similar (e.g., allowing a GOOGLE CHROME process to be compared to other GOOGLE CHROME processes rather than a MICROSOFT EXCEL process), and (2) mine for patterns in the data to single out outliers in each category.

Figure 1B:
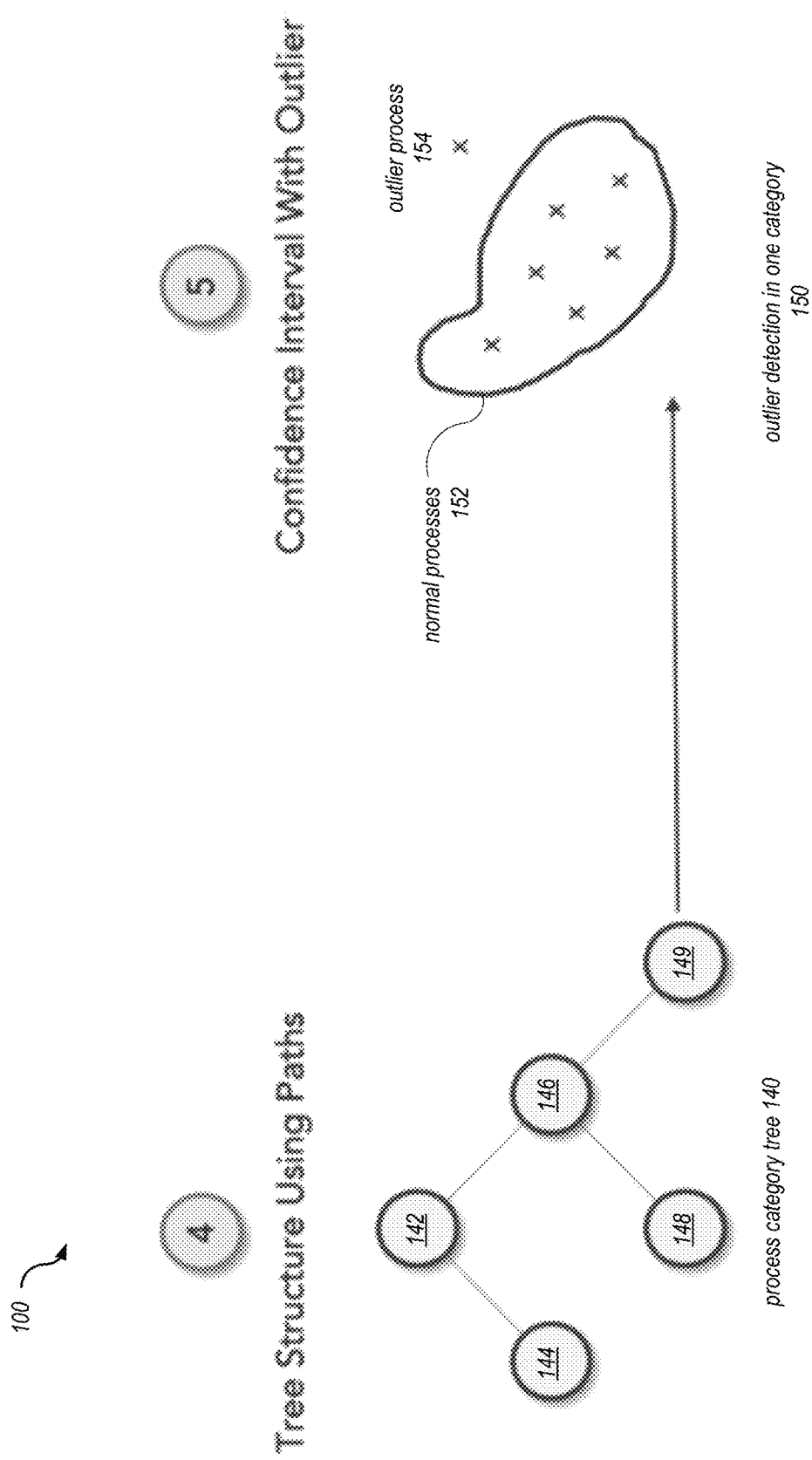

As shown in FIG. 1B, based on the natural structure of process categories 120, a tree (e.g. process category tree 140) may be created. In this example, each node 142, 144, 146, 148, and 149 may present a particular directory seen in the file system hierarchy of a host 112 in the computer network 110. In some embodiments, the individual leaves of the tree (e.g. nodes 148 and 149) represent different categories 120 of similar processes.

In some embodiments, the collected data may include a huge number of processes and process categories 120. To cope with the amount of data, in some embodiments, hosts are considered individually to aggregate processes for a given leaf. Each leaf is then merged together across all hosts to obtain a collection of all processes and features with that same path. In some embodiments, the generation of the leaves may include the following steps: (1) group dataset collected from the network by the host identifier; (2) for each sub-dataset of a host, create a tree (e.g. process category tree 140 in FIG. 1B) where each leaf contains the engineered features of all processes with the same executable path; and (3) once all the trees have been computed (e.g. via parallelized computations), the trees are recursively merged into a single tree across the hosts. In some embodiments, the leaves are stored as sparse matrices, and the merging process merges the columns of the matrices so that the columns are the same across all matrices (e.g. by padding with zeros any missing features in the individual leaf matrices).

In some embodiments, the anomaly detection system may use machine learning techniques to identify outlier processes in each process category using the sparse matrix as the input dataset. As shown in FIG. 1B, for a given observation period and a given process category 149, the anomaly detection system may perform an outlier detection process 150 to determine one or more outlier processes 154 observed during the period. The outlier process 154 may be sufficiently different from the "normal" processes 152 previously observed in the category, as determined based on one or more machine learning models.

3. Pre-Processing

3.1 Feature Extraction

In some embodiments, the anomaly detection system performs a pre-processing or feature engineering stage to extract features from the process records 130 into input feature vectors that can be used by the machine learning models. In some embodiments, the feature extraction process may be performed using: (1) binarization, where the data is casted to a binary value {0, 1} indicating the presence or absence of a process feature value, thus normalizing the data to a common format and removing question of magnitude; or (2) a TF-IDF (term frequency-inverse document frequency) process, where the feature values in the observation records are scaled according to a term frequency to identify frequency value to highlight more relevant information in the observation records.

In some embodiments, to determine the TD-IDF metric of feature values, an observation record is treated as a document, and each distinct feature value in the observation record is treated as a term. A term frequency tf(t,d) of a term may be calculated as the raw count of a term t in document d. Then, the inverse document frequency of the term may be determined using the formula:

$$idf(t, D) = \log\left(\frac{N}{\text{number of documents in corpus } D \text{ that contain } t}\right)$$

where N is the total number of documents in the corpus D. In some embodiments, the corpus D may include a body of many historical process records that are stored by the anomaly detection system. The inverse document frequency represents a measure of how rare a term is in the corpus of documents. Finally, the TF-IDF score of the term may be determined as the product of the two quantities:

$$tfidf(t,d,D)=tf\cdot idf$$

As will be appreciated by those skilled in the art, there are a number of variations in the manner that a TF-IDF metric can be calculated. Depending on the embodiment, these other methods may also be used by the anomaly detection system to encode the feature vectors.

In some embodiments, an observation record may be augmented with additional features about processes that are relevant to the hunt process. For example, in some embodiments, the observation record may be augmented to include a risk score associated with the executable that was executed by the process (e.g. obtained from a third party knowledgebase). In some embodiments, additional process features may be inferred from historical data. For example, the observation record may be augmented to indicate whether the process is the first time a particular executable has executed on the particular host. As another example, another feature may indicate whether the execution time of the process ranks in the top quartile of previous processes in the process category. As yet another example, a feature may indicate whether the process represents a whitelisted process that is known to be a benign process on the host. In some embodiments, these augmented features may be added to the observation record using engineered tokens before the binarization or TF-IDF steps described above.

3.2 Matrix Representation

Figure 2A:
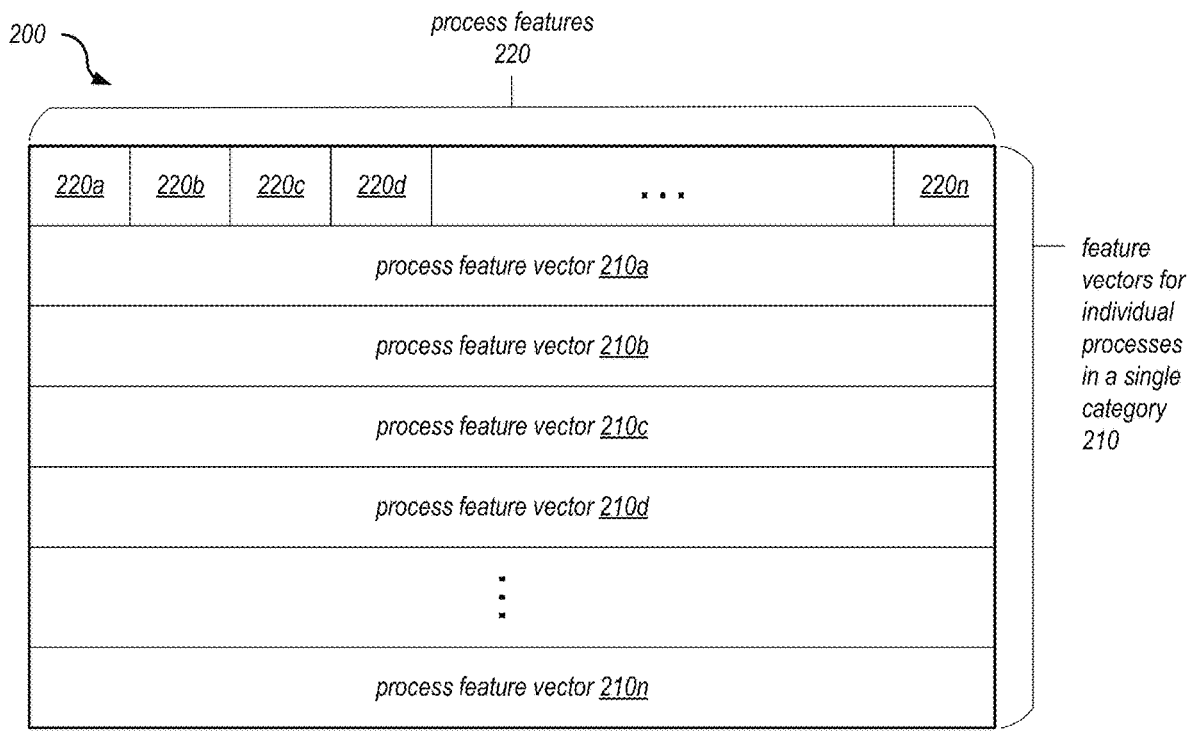
FIGS. 2A and 2B illustrate matrices of different types of feature vectors that are extracted from observation data by a machine learning anomaly detection system, according to some embodiments.
Figure 2B:
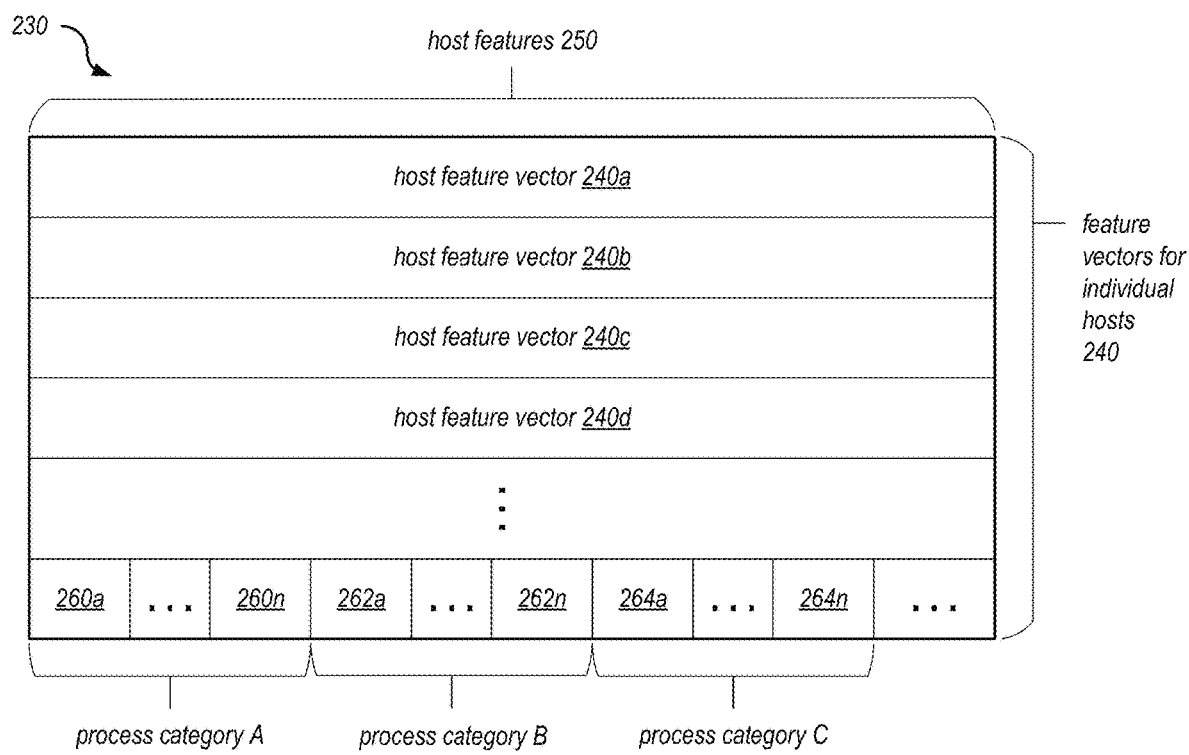

FIGS. 2A and 2B illustrate matrices of different types of feature vectors that are extracted from observation data for use by a machine learning anomaly detection system, according to some embodiments.

FIG. 2A depicts a matrix 200 that is generated from the observation records 130. The matrix 200 may be produced from the feature extraction processes described in the previous section. As shown, in matrix 200, each row 210*a-n* represents a feature vector for an individual process. The processes included in the matrix 200 may belong to a single process category (e.g. process category 120 of FIG. 1A). Each column 220*a-n* in the matrix represents an extracted feature of a process (e.g. a binary value or a TF-IDF value generated from the observation records). In some embodiments, the anomaly detection system will use machine learning model(s) to identify one or more outlier processes from the processes represented in the matrix 200.

FIG. 2B depicts another matrix 230 that may be generated by the anomaly detection systems. In this example, the rows 240*a-d* in the matrix 230 represent features vectors of individual hosts 112 in the network. Thus, the columns 250 in the matrix represent features of individual hosts. As shown, in some embodiments, each host feature vector 240 may include features of the different process categories 120 (e.g. features 260*a-n* for process category A, features 262*a-n* for process category B, and feature 264*a-n* for process category C). Features for a given process category (e.g. features 260*a-n*) may indicate information about processes in the category, such as the number of processes that were observed on the host for the category, any common process features for processes in the category (e.g. the path of the executable), and various aggregate features computed from the observed processes in the category. For example, an aggregate process feature may indicate the longest execution time of all processes in the category, the average number of disk accesses performed by the processes in the category, the total number of network requests by the processes in the category, etc. In some embodiments, the host matrix 230 may be constructed after an outlier detection has been performed on the observed processes. In that case, the host feature vectors 240 may include results of the process outlier detection process, such as whether an outlier was identified in each process category, and the highest outlier metric found in each process category, among other findings.

In some embodiments, the anomaly detection system will use machine learning model(s) to identify one or more outlier hosts from the hosts represented in the matrix 230. In some embodiments, the hosts in matrix 230 may represent all hosts 112 in the network 110 seen during an observation period. In some embodiments, the hosts in the matrix 230 may include a category of observed hosts that satisfy one or more category criteria.

As may be appreciated, the matrices 200 and 230 may have very high feature dimensionality (columns) due to the large number of distinct feature values observation records. For example, matrix 200 may include a column for each distinct feature value seen in the observation records (e.g.

each DLL name, each MD5 value, etc.). Matrix 230 may also have high dimensionality based on the large number of distinct process categories.

3.3 Dimensionality Reduction

Figure 3A:
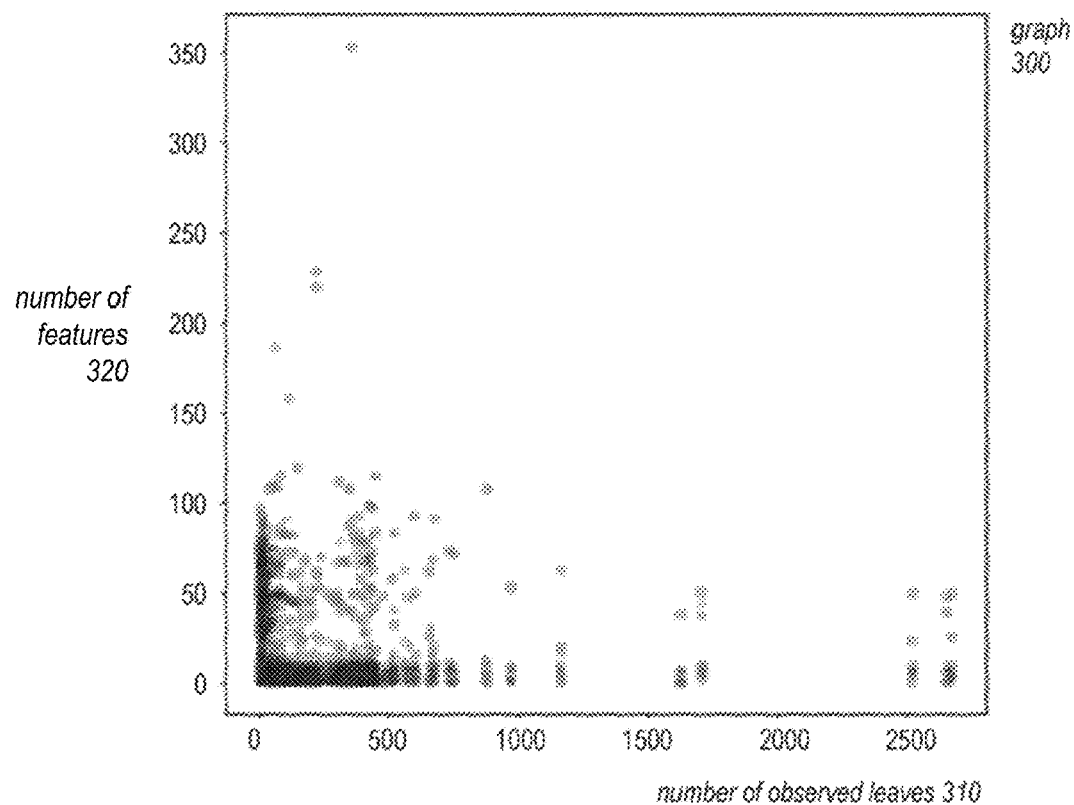
FIG. 3A is a graph 300 showing the shape of leaves of a process category tree determined by a machine learning anomaly detection system, according to some embodiments.
Figure 3B:
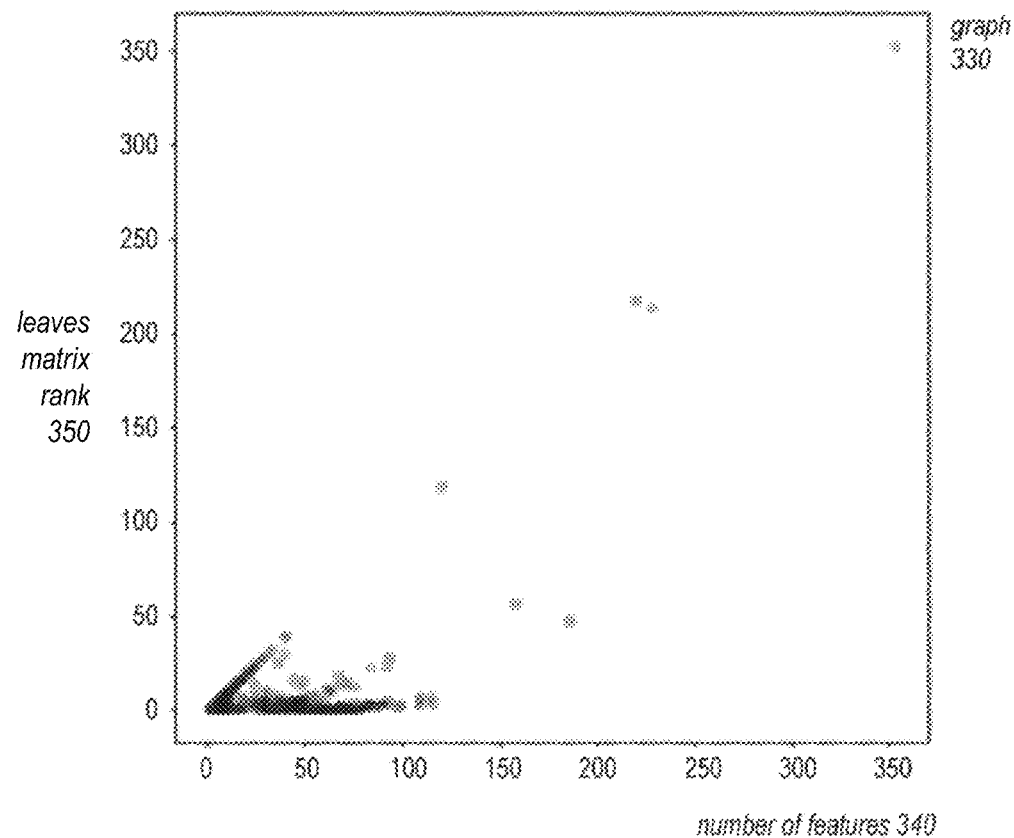
FIG. 3B is a graph 330 of the leaves matrix rank as a function of number of features determined by a machine learning anomaly detection system, according to some embodiments.

In some embodiments, given the high dimensionality of the input feature vectors under consideration (e.g., as shown in FIG. 3A), the anomaly detection system will apply one or more dimensionality reduction techniques to reduce the dimensionality of the vectors to cast the input data to a lower dimensional space (e.g., given the low rank of the leaves as shown in FIG. 3B).

FIG. 3A is a graph 300 that shows a distribution of the number of features 320 that were extracted for many observed leaves (e.g. process categories 120), according to one study. The x-axis 310 shows the frequency count of leaves that had a particular number of features. As shown, the anomaly detection system generated some leaves with large numbers of features (e.g. greater than 100 process features). This means that the matrix of feature vectors (e.g. matrix 200) is a fairly wide and sparse matrix. However, as shown in FIG. 3B, for most process categories, with their number of features shown in the x-axis 340, the "rank" of the matrix (e.g. the linearly independent features of the process category), shown in the y-axis 340, are much smaller. This result thus suggests that the feature vectors could benefit greatly from dimensionality reduction.

Depending on the embodiment, dimensionality reduction in the anomaly detection system may be performed using one or more of several methodologies. The methodologies include but are not limited to:

Principal Component Analysis (PCA);

Non-Negative Matrix Factorization (NMF), which may be adapted to positive data, with variants such as Binary Matrix Factorization (BMF);

Logistic PCA, which is type of PCA that accounts for the binary nature of the data and is particularly relevant to hunt data;

Robust PCA, which is yet another type of PCA that accounts for the potential presence of outliers in the data by taking into account the L1 norm (calculating the variance by using absolute values to diminish the impact of outliers on the data) versus the L2 norm (calculating the variance by using squared differences);

Auto Encoder, which is a type of feed-forward neural network that is trained using machine learning to approximate an identity function that maps a high-dimensional feature vector onto itself, but using an intermediate representation that has reduced dimensionality; and Randomized Projection, which uses random projection to reduce dimensionality while preserving pairwise distances, thus allowing for distance-based methods in downstream tasks.

Given the size of the hunt data, there are number of technology-related challenges associated with assessing the effectiveness of the dimensionality reduction methods on the quality of predictions in the downstream task. These challenges are further compounded by the fact that there are no labels to measure the effectiveness of anomaly detection. Therefore, in one study, synthetic data is used to generate a regression with binary data and previous algorithms on the downstream task of the regression are compared.

Figure 4A:
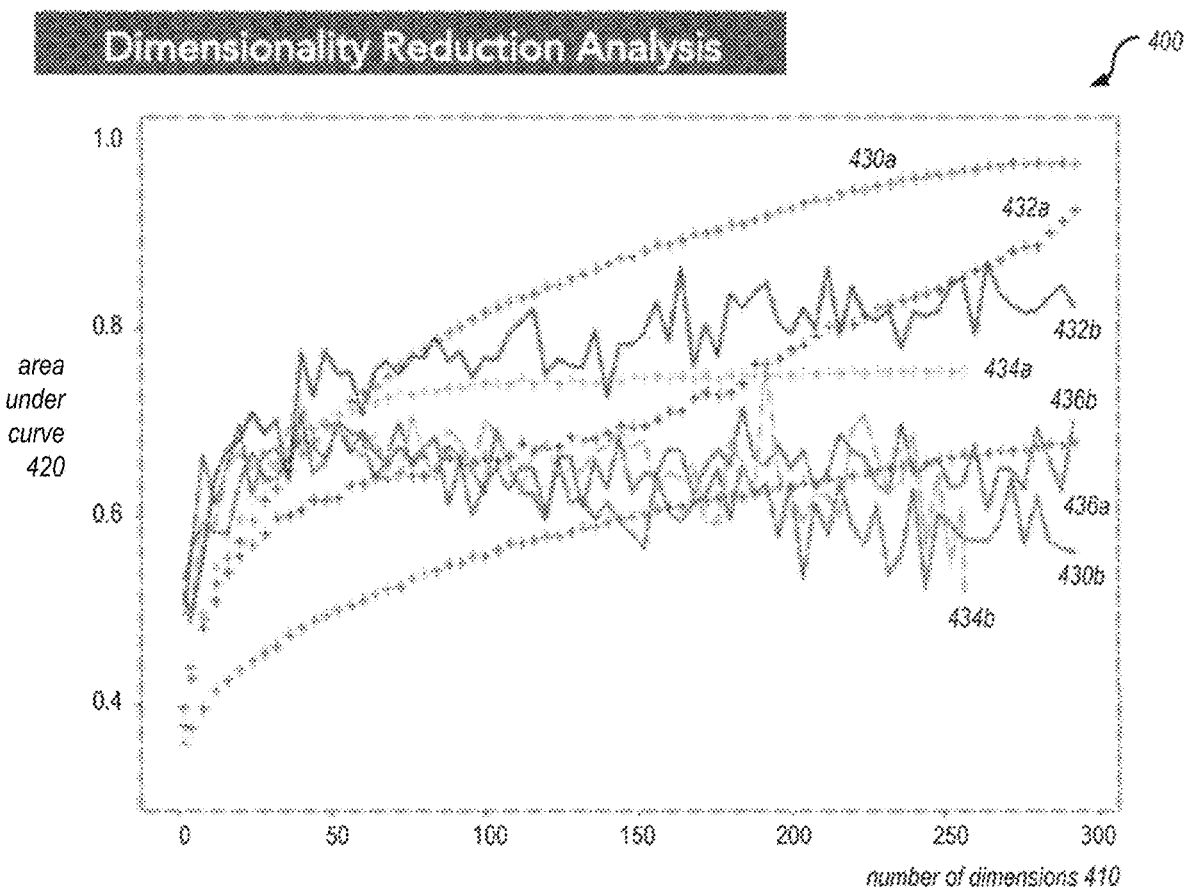
FIG. 4A is a graph 400 showing the performance of different dimensionality reduction techniques that may be used in a machine learning anomaly detection system, according to some embodiments.

The results of the study are shown in FIG. 4A. As shown in graph 400, the area under curve 420 for model accuracy metrics are plotted for datasets that were transformed using different dimensionality reduction techniques. As shown along the x-axis 410, the number of resulting dimensions 410 of the dataset was also varied, so that the graph shows how the ultimate model performance varied with the magnitude of dimensionality reduction. In the graph 400, curves 430a and 430b are the performance results for PCA, curves 432a and 432b are the results for NMF, curves 434a and 434b are the results for BMF, and curves 436a and 436b are the results for randomized projection. In the graph 400, the dotted lines 430a, 432a, 434a, and 436a represent explained variance, and the solid lines 430b, 432b, 434b, and 436b represent accuracy.

In the study, it is determined that NMF not only performs the best (on average), but also offers better resistance to dimensionality. Moreover, the results indicated that PCA tended to remove small perturbations (as discussed later with respect to scenario-based model testing). At least for these reasons, Robust PCA may be used as a preferred method for dimensionality reduction to get the best of both worlds by extracting a general low rank matrix L as well as a sparse matrix S denoting potential anomalies. However, if computing power is a limiting factor, PCA may be used instead of Robust PCA as a preferred method.

In some embodiments, the anomaly detection system may be configured to support multiple types of dimensionality reduction methods. The anomaly detection system may be configured to select one or more of the dimensionality reduction methods at runtime, either automatically based on runtime conditions (e.g. recent model evaluation results), or based on configuration settings specified by analysts. In some embodiments, the dimensionality reduction models used by the anomaly detections system may be periodically updated using unsupervised machine learning techniques, so that no manually labeling of the data is required. In this manner, the dimensionality reduction models can be gradually adapted to the hunt data with little or no human supervision.

3.3.1 Finding the Best Dimension

A significant task when performing dimensionality reduction is to tune the number of dimensions of the final space. However, given that the available data for the downstream models are not labeled, a critical metric is missing to evaluate the downstream tasks to determine the right value of this hyper-parameter.

Figure 4B:
FIG. 4B illustrates a technique to determine an ideal number of dimensions for dimensionality reduction used in a machine learning anomaly detection system, according to some embodiments.
Figure 4B:

Therefore, in some embodiments, columns of the binary dataset are bootstrapped over and the columns are considered as labels of a binary classification algorithm. In this example, anomalies will likely be noticeable through variations in a column and therefore, this is an acceptable proxy to assess the ability to retrieve this information after dimensionality reduction. FIG. 4B shows a summary of this technique to determine the ideal number of dimensions for dimensionality reduction.

As shown in the example, for each leaf, for each column c, for each possible dimension k, at least the following is performed: (1) reduce feature dimensionality to dimension k on columns of the leaf, but excluding column c; (2) training a classifier to predict c based on the data of the previous step; and (3) computing the area under the curve (AUC) of this trained classifier on the left out data. The k that works best on average and gives the best AUC is then selected as the best dimension.

However, in some embodiments, the foregoing process can be very time consuming. Therefore, in some embodiments, a regression algorithm is trained on one or more metrics related to the data alone to predict the associated k. In this manner, computing resource heavy calculations are avoided in production, while an effective predicted value of k is obtained fairly quickly (e.g., with a mean squared error (MSE) of 0.22 for normalized data).

Furthermore, the dimension value determined by the disclosed technique is generally stable and produces close-to-ideal values of k for a wide range of possible dimensions, leading to 95% of the optimal model performance in the anomaly detection system. Therefore, despite the variance in the predictor due to the imperfectness of the input, the technique can be used to generate close-to-optimal values of the dimension k for dimensionality reduction.

4. Machine Learning Models

In some embodiments of the anomaly detection system, the outliers in the hunt data are identified using one or more of the following machine learning models.

4.1 Isolation Forest

In some embodiments, Isolation Forest, which is based on the process and structure of a Random Forest, is used by the anomaly detection system to detect outliers. Isolation Forest models are built on the notion that there are only a few outliers and that they are different from the rest of the data. Under this hypothesis, an Isolation Tree (e.g. tree 510a-c) is built by recursively splitting features space randomly and then computing the depth for each individual point. There is an assumption here that shorter paths in the tree are likely to be associated with anomalies because they are more likely to be sectioned off by an early cut or split.

Figure 5:
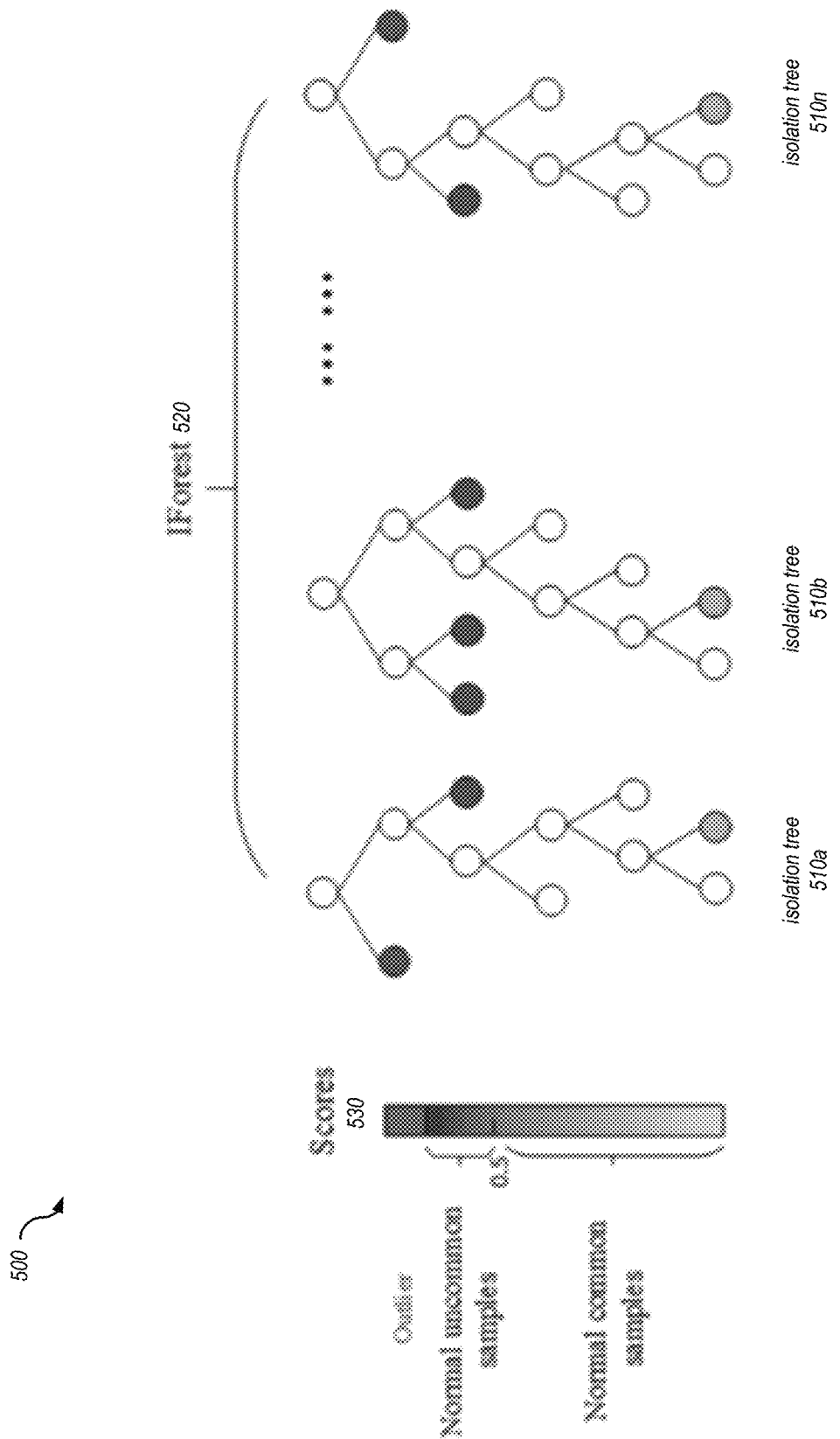
FIG. 5 is an illustration 500 of a visualization of Isolation Forest model that may be used in a machine learning anomaly detection system, according to some embodiments.

As shown in FIG. 5, a number of Isolation Trees 510a-c are used, where each tree selects a random sample size and set of features, which are then merged into an Isolation Forest 520. The outlier score produced by the Isolation Forest 520 may be an average of the depths across each Isolation Tree 510a-c to reduce variance. The score is mapped to a score range 530, which may be calibrated based on scores of historical processes or hosts in the relevant category. In some embodiments, the ranking of a score in the range 530 may be used as the outlier metric of the particular process or host.

In some embodiments, it is observed that Isolation Forest may not perform optimally with highly-dimensional, sparse, and binary data. One reason behind this observation may be that a single flipped bit is not easily caught by the Isolation Trees, as the probability of splitting on it is inversely proportional to the dimension of the space and can therefore rarely influence the depth of such an anomaly within an Isolation Forest. This can make it difficult to pick up anomalies through the Isolation Forest methodology. Therefore, in order to improve the accuracy of Isolation Forest models, it may be necessary to first implement dimensionality reduction using the algorithms discussed earlier, in some embodiments.

4.2 One-Class Support Vector Machine

Figure 6:
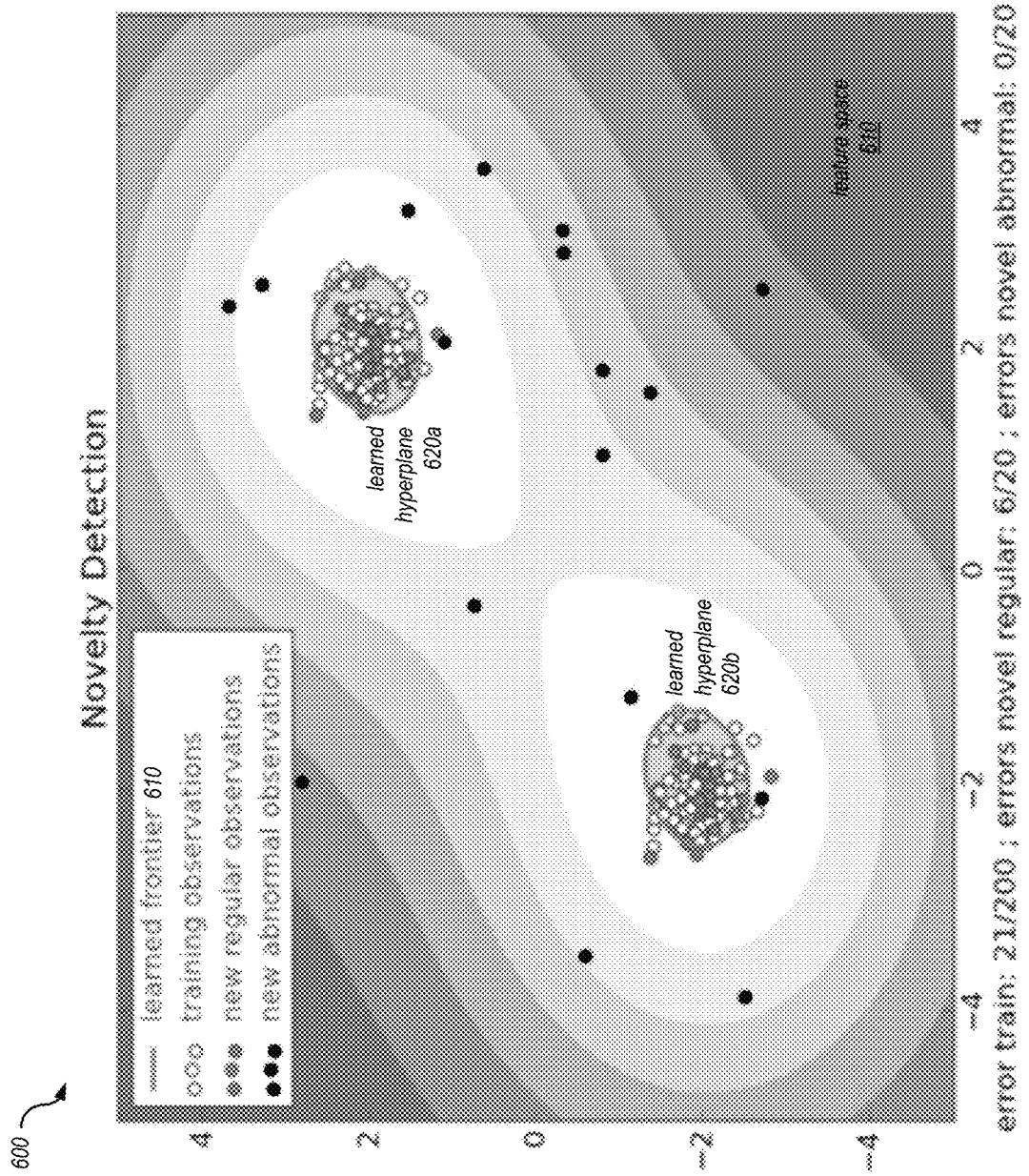
FIG. 6 is an illustration 600 of a visualization of One-Class SVM that may be used in a machine learning anomaly detection system, according to some embodiments.

In some embodiments, the anomaly detection system may be configured to use a One-Class Support Vector Machine (SVM) as an outlier detection model. A One-Class SVM is an unsupervised machine learning algorithm similar to the general SVM in term of formulation. A SVM is a classifier trained to discriminate data based on separating hyperplanes. In other words, given labeled training data (supervised learning), the algorithm outputs an optimal hyperplane which categorizes new examples. In a two-dimensional space, this hyperplane is a line dividing a plane in two parts where the classes lay on different sides of the line. With One-Class Support Vector Machines, the main subtlety is that there is only one class and most of the data is enclosed on one side on the learned hyperplane. One-Class SVMs are trained using an unsupervised machine learning technique without labels, and these models may be trained to learn a frontier between normal and outlier datapoints. FIG. 6 illustrates a feature space 610 projected into two dimension for easier visualization. As shown, the figure depicts a number of observations in the feature space (e.g. process feature vectors 210 or host feature vectors 240), and a hyperplane 620 learned by an example One-Class SVM, and an One-Class SVM's performance in detecting abnormal or outlier observations based on the hyperplane.

4.3 Classifier Trained to Distinguish Real and Synthetic Data

Figure 7:
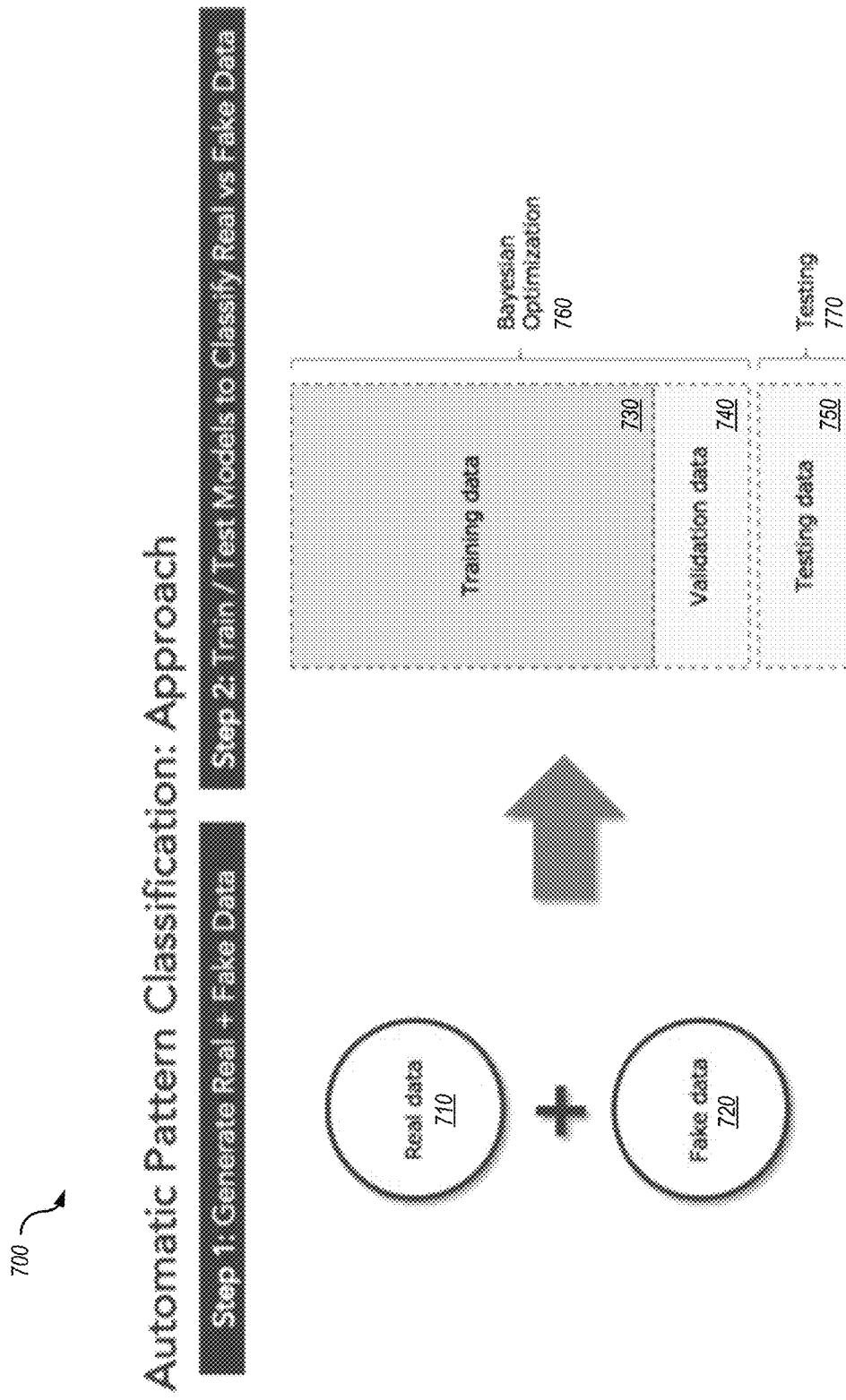
FIG. 7 is a block diagram 700 of an approach to automatic pattern classification that may be used in a machine learning anomaly detection system, according to some embodiments.

In some situations, patterns in the observation data may be mined by comparing the actual data to synthetic data that is generated in the same space. FIG. 7 depicts an approach to automatic pattern classification that may be used to build a classifier model used by the anomaly detection system to detect outliers. As shown, the approach first generates fake or synthetic data 720. In some embodiments, the synthetic data may be uniformly distributed across the feature space. The synthetic data 720 is combined with real data 710 to create a dataset used to train a classifier model. Assuming that the actual observation data is non-random, the classifier can be trained to distinguish between the real data 710 and the fake data 720. In turn, the trained classification model can be used to provide an outlier score for new datapoints (e.g. based a confidence that a new datapoint is a real datapoint).

For example, in some embodiments, an assumption is made that 95% of a real dataset X is expected to lie within a connected and convex volume V, where V is the smallest subset that verifies this property. Next, the smallest hypercube H that contains V is obtained, which increase the size of V and constructed to have the same mean as V. Points in H may be sampled to generate the synthetic datapoints, which are labeled as 1. The points of the real dataset are labeled 0. A non-linear classifier, such as a Random Forest, may then be trained on a balanced subset of real and fake data to learn the volume V within H. Based on this training, this classifier will be able to learn the frontiers of the volume V to separate the real data 710 from fake data 720. The learned frontier may then be used to detect outliers that deviate from the 95% of the "normal" data.

4.3.1 A Classification Task

Now that the problem of anomaly detection is characterized as a classification task, one of a number of machine learning classification models may be used. Example classification models include K-Nearest Neighbors (KNN), Random Forest, Logistic Regression, XGBoost, Support Vector Machine, or Neural Networks. One downside of this approach is that when the data is very high-dimensional, the randomly generated synthetic data may not adequately cover the feature space due to the large dimensionality. However, this problem is mitigated to a degree by using the dimensionality reduction techniques discussed earlier. Note that, although the classification model is trained using labeled data, in this case, the labeling is performed automatically by the computer system. Thus, this approach does not require any manual labeling of data as outlier or non-outlier.

4.3.2 Bayesian Optimization

As shown in FIG. 7, in some embodiments, in order to train the classifier model automatically, the real data 710 and fake data 720 are concatenated into a single dataset, and split in a desired manner into a training dataset 730, a validation dataset 740, and a testing dataset 750. Then, for a given set of hyper-parameters the classifier is trained on the training set 730. The AUC on the validation set 740 is reported on the resulting classifier. In some embodiments, a Bayesian Optimization framework 760 is used to select a next point of hyper-parameters to evaluate. After some number of training-validation iterations performed according to the Bayesian Optimization framework, the trained model may be tested 770 on using test dataset 750 before reporting AUC.

4.3.3 Generating More Useful Synthetic Data

In many cases, it is important to generate good synthetic data that will be instructive for model training. However, a random approach to generating synthetic data often does not produce a good dataset. For example, if the feature space is particularly large in terms of dimensionality and if actual observations occupy a relatively small area in the feature space, randomly generating synthetic data in the space will generally fail to provide sufficient coverage in the salient regions of the features space (e.g. regions near the frontiers of observed data). Most of the synthetic data will be generated in regions that are far away from where the actual observations reside. Such randomly generated synthetic data are not very useful for training a model to learn the frontiers of the data or testing the model's ability to detect the frontiers.

Additionally, it is sometimes useful for data scientists to specify desired characteristics of a frontier to be learned by a model, such as how far a learned frontier should extend from the center of the observed dataset. However, it is generally difficult to specify such characteristics using conventional data generation techniques.

In order to solve the foregoing problems, in some embodiments, the anomaly detection system implements a synthetic data generation system that uses density estimation to generate useful synthetic datapoints in salient areas of the feature space. The disclosed technique can be used to mitigate the problems of inadequate coverage that can result from purely random synthetic data generation. Moreover, the disclosed technique can be controlled so that the synthetic data is generated in particular regions to encourage the learning of desired frontiers in the data. The disclosed process produces better datasets for machine learning and results in faster training times and better models.

Figure 8:
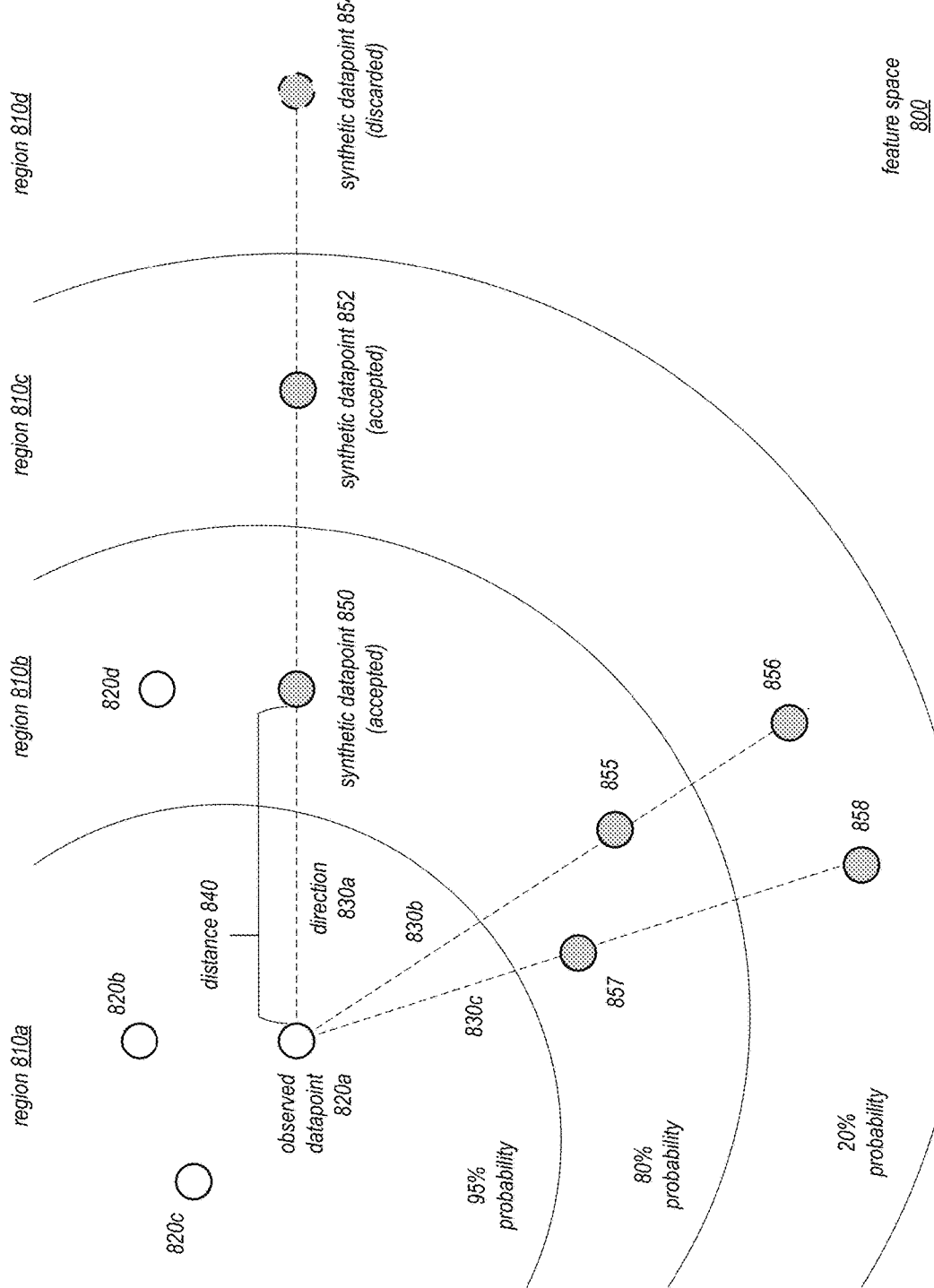
FIG. 8 illustrates a technique for generating synthetic data to train and evaluate machine learning models in a machine learning anomaly detection system, according to some embodiments.

FIG. 8 illustrates a technique for generating synthetic data to train and evaluate machine learning models in a machine learning anomaly detection system, according to some embodiments. As shown, the figure depicts a feature space 800, which for illustration purposes is shown here in two dimensions. In practice, the feature space 800 may be a feature space of high dimensionality, having hundreds or thousands of dimensions.

As shown, a dataset of observed datapoints, including datapoints 820*a-d* shown in white, exist in the features space 800. In some embodiments, the observed datapoints 820 may be feature vectors to be analyzed by the outlier detection models used by the anomaly detection system, as discussed in connection with FIG. 7. In some embodiments, these datapoints 820 may encode behaviors of hosts, such as processes or process categories observed on the hosts.

In some embodiments, a density function may be determined using the dataset of observed datapoints. The density function may represent a statistical model of the observed dataset. In some embodiments, the density function used to determine the probability of any given datapoint in the feature space being observed in the dataset. In some embodiments, density function may be estimated using a density estimation technique such as a Kernel Density Estimator with Gaussian kernels. However, as will be appreciated by those skilled in the art, other types of density estimators with different guarantees may also be used.

As shown in this example, three contours of the density function are shown: a contour with 95% probability of observation, a contour with 80% probability of observation, and contour with 20% probability of observation. These contours (which may be surfaces in n-dimensional space) represent the shape of a density function in the feature space. As shown, the contours divide the feature space 800 into regions 810*a-d*.

In some embodiments, the synthetic datapoint generation process will generate synthetic datapoints (e.g. datapoints 850, 852, 854, 855, 856, 857, and 858 in grey) by sampling and varying the observed datapoints. In this example, observed datapoint 820*a* is selected to generate synthetic datapoints. However, the illustrated process may be repeated for many observed datapoints 820 in the observed dataset. In some embodiments, the observed datapoints used to generate synthetic datapoints may be selected at random. In some embodiments, the observed datapoints may be selected based on one or more selection criteria, such as how far they are from the center of the observed dataset, their respective categories, or their respective feature values.

As shown, to generate synthetic datapoints, a number of different directions (e.g. directions 830*a-c*) are selected from the observed datapoint 820*a*. In some embodiment, a direction may be represented as a unit vector selected from the hypersphere around the observed datapoint 820*a*. In some embodiments, a direction may be based on a selected feature in the feature vector of the datapoint. In some embodiments, the direction 830 may be a linear combination of multiple features in the feature vector. In some embodiments, the directions 830*a-c* may be selected at random. In some embodiments, the directions may be selected based on the location of the observed datapoint in the feature space (e.g. relative to the center of the observed dataset), the density function probability of the observed datapoint, or based on configuration settings (e.g. limiting the synthetic data generation to varying only particular features).

In some embodiments, for each selected direction 830*a-c*, a number of candidate synthetic datapoints are generated in that direction at different distances (e.g. distance 840 for synthetic datapoint 850). As shown, based on the direction 830*a* and the distance 840, the synthetic datapoint 850 is generated from the observed datapoint 820*a*. In some embodiments, the different distances for generating synthetic datapoints in a particular direction may be determined at random. In some embodiments, the distances in a particular direction may be constrained to fall within a specified range. In some embodiments, the process may generate a number of successive synthetic datapoints with increasing distances (e.g. successive datapoints 850, 852, and 854) until the probability of the last generated datapoint falls below a specified threshold. The threshold may be a configured parameter that prevents synthetic datapoints from being generated in regions of the feature space that are too far away from the real data.

In some embodiments, instead of selecting a direction first and then the distance for a synthetic datapoint, the process may first select the distance and then the direction. For example, in some embodiments, the process may select a particular distance, and then generate synthetic datapoints in multiple directions at the particular distance. In some embodiments, the process may employ both methods (direction-first and magnitude-first) to generate synthetic datapoints.

As shown, in this example, three synthetic datapoints 850, 852, and 854 are generated in direction 830*a*. Synthetic datapoints 850 and 852 are accepted, while synthetic datapoint 854 is not accepted and discarded. In some embodiments, the process may generate each synthetic datapoint as a candidate, and then check the candidate datapoint against an acceptance criterion to determine whether the candidate datapoint should be retained (e.g. added to a dataset for machine learning applications). The acceptance criterion may be based on the density function determined for the observed dataset. For example, the acceptance criterion may accept a candidate datapoint if the datapoint is within an acceptable range of probability values indicated by the density function. Datapoint 854 may be discarded because it is outside such an acceptable range, which means that the datapoint is too dissimilar from the observed datapoints.

Depending on the embodiment, generated synthetic datapoints may be discarded for a variety of reasons. In some embodiments, a candidate datapoint may be discarded if its probability of observation based on the density function is too high. In some embodiments, a candidate datapoint may be discarded if it is too close to other synthetic datapoints in the feature space. In some embodiments, a candidate datapoint may be discard if there are already a sufficient number of synthetic datapoints generated in a similarity group of the candidate point. In some embodiments, candidate datapoints may be discarded in a random fashion. For example, in some embodiments, a random value between 0 and 1 may be generated for each candidate point. If the random value is above the density function probability of the candidate datapoint, it is retained. If the random value is below the density function probability of the candidate datapoint, it is discarded. This technique adds some randomness to the synthetic data generation process, while preferring datapoints that are closer and more similar to the observed datapoints.

In some embodiments, the synthetic data generation process may involve a pre-selection of a range of distance values to use for generating synthetic datapoints, which may be implemented as follows. Consider an observed dataset $X \in \mathcal{M}_{(n,d)}$ where $d \in \mathbb{N}^*$. An observed datapoint u is bootstrapped from dataset X. A synthetic datapoint is generated using a direction w for randomly selected from the d-dimensional hypersphere of radius 1 and a distance $\rho$. The assumption is that there exists a density function $\psi$ that dataset X was sampled from. Using a density estimation algorithm, this density may be estimated by $\hat{\psi}$. The density function probability of the resulting synthetic datapoint may be expressed as the random variable $\hat{\psi}(u+\rho \cdot w)$. A value $d(\rho)$ may then be defined as the expected value of this random variable:

$$d(\rho) = \mathbb{E}(u+\Sigma \cdot w))$$

Because $d(\rho)$ is a continuous function of $\rho$, there exist distances $\rho_1$ and $\rho_2$ such that $d(\rho_1)=\delta_1$ and $d(\rho_2)=\delta_2$. The distance values $\rho_1$ and $\rho_2$ may be estimated through an iterative dichotomy process. With the distance range determined, the synthetic datapoint generation process may then generate synthetic datapoints within the distance range of $[\rho_1, \rho_2]$. In some embodiments, the probabilities $\delta_1$ and $\delta_2$ may be specified as configuration information, so that the user can explicitly control how similar or dissimilar the generated synthetic data is to the actual observation data.

Figure 9A:
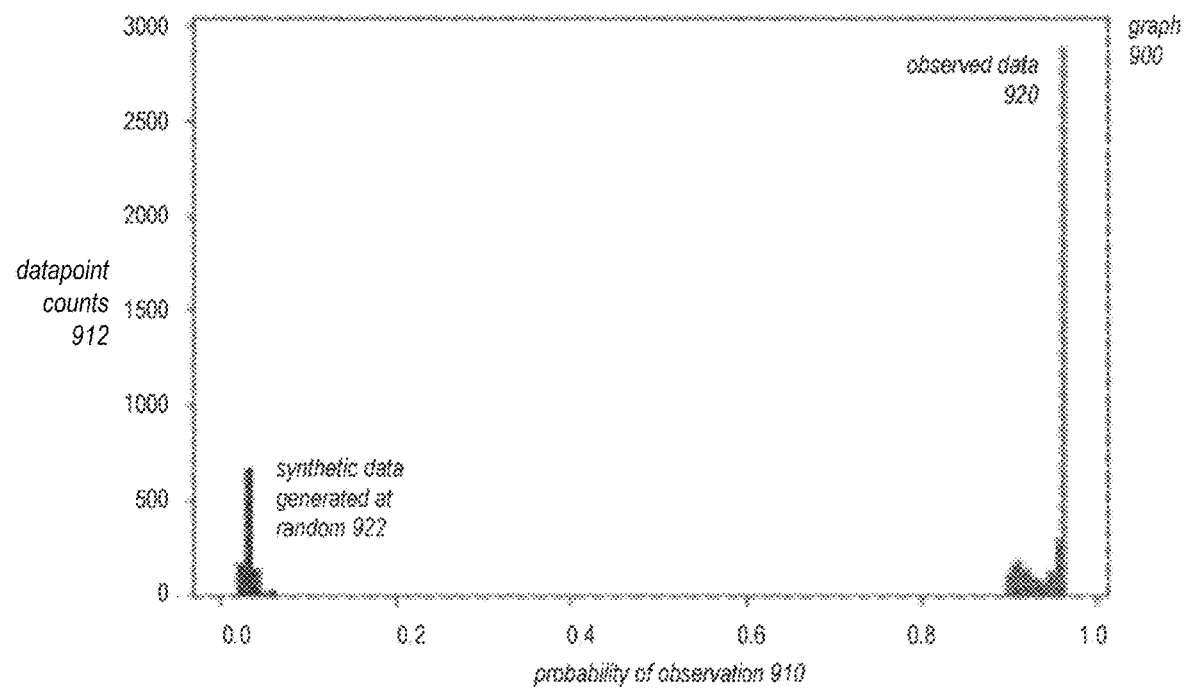
FIG. 9A is a histogram 900 is a showing the probability of observing real data versus synthetic data regenerated uniformly at random, according to a density function of the real data generated by a in a machine learning anomaly detection system, according to some embodiments.
Figure 9B:
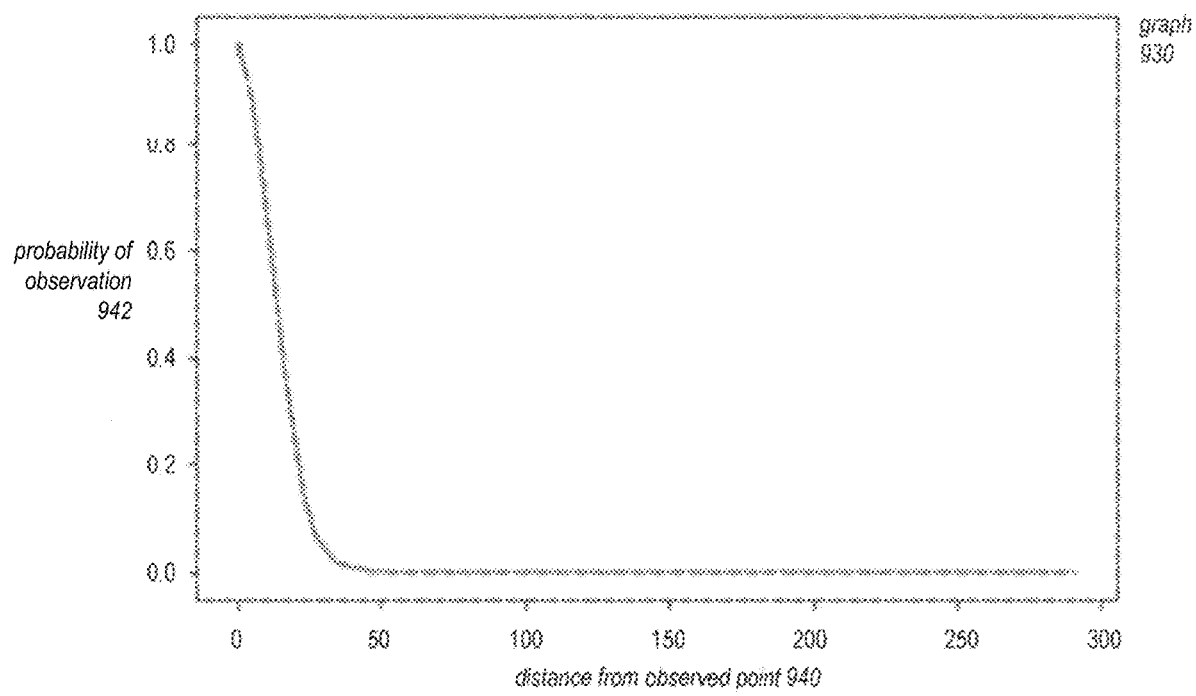
FIG. 9B is a graph 930 showing the relationship between a distance from an observed datapoint and the density function probability of a synthetic datapoint at that distance, according to some embodiments.

In some embodiments, the process may randomly sample p from the distance range to create enough data to perform a linear regression between p and $d(\rho)$, as shown in FIG. 9B. As shown in graph 930, the relationship between the distance 940 and the density function probability 942 may be non-linear. In some embodiments, the determined relationship between the distance 940 and the density function probability 942 may be used to generate successive synthetic datapoints in a particular direction with increasing distances, in such a way that the successive datapoints are spaced to have uniformly decreasing density function probabilities.

In some embodiments, the probabilities $\delta_1$ and $\delta_2$ may be obtained from two different density functions. For example, in some embodiments, probability value $\delta_1$ may be obtained from the density function of the observed dataset. Additionally, the system may randomly generate a dataset of synthetic datapoints that is uniformly distributed across the feature space (or some selected region of the feature space). Probability value $\delta_2$ may be obtained from a second density function that is estimated from the dataset of random synthetic datapoints. In this way, the user can constrain the synthetic datapoints using two probability values from the two different density functions, for example, so that all generated datapoints have greater than the 5th percentile of the probability of being observed in the real dataset according to the first density function and less than a 95th percentile of the probability of being observed in the random dataset.

As may be appreciated by those skilled in the art, the above process may be repeated for many different observed datapoints, in many different directions, and using many different distances to quickly generate a large population of synthetic datapoints. Synthetic datapoints generated in this way tend to be much closer to the actual observed data in the feature space, making these datapoints more useful for machine learning applications.

FIG. 9A shows a histogram 900 of datapoint counts 912 at different probability values 910 of the density function. As shown, the probability values of the actually observed datapoints 920 is high and very far away from the probability values of the synthetic datapoints generated at random 922. This means that the synthetic data points are dissimilar from the observed datapoints, and not very good datapoints for training or evaluating machine learning models for detecting outliers for future observed datasets. It would be more useful to generate synthetic data in the vicinity of the real observed data, where the density function is starting to decrease (e.g. near the frontiers of the observed data 920).

Figure 9C:
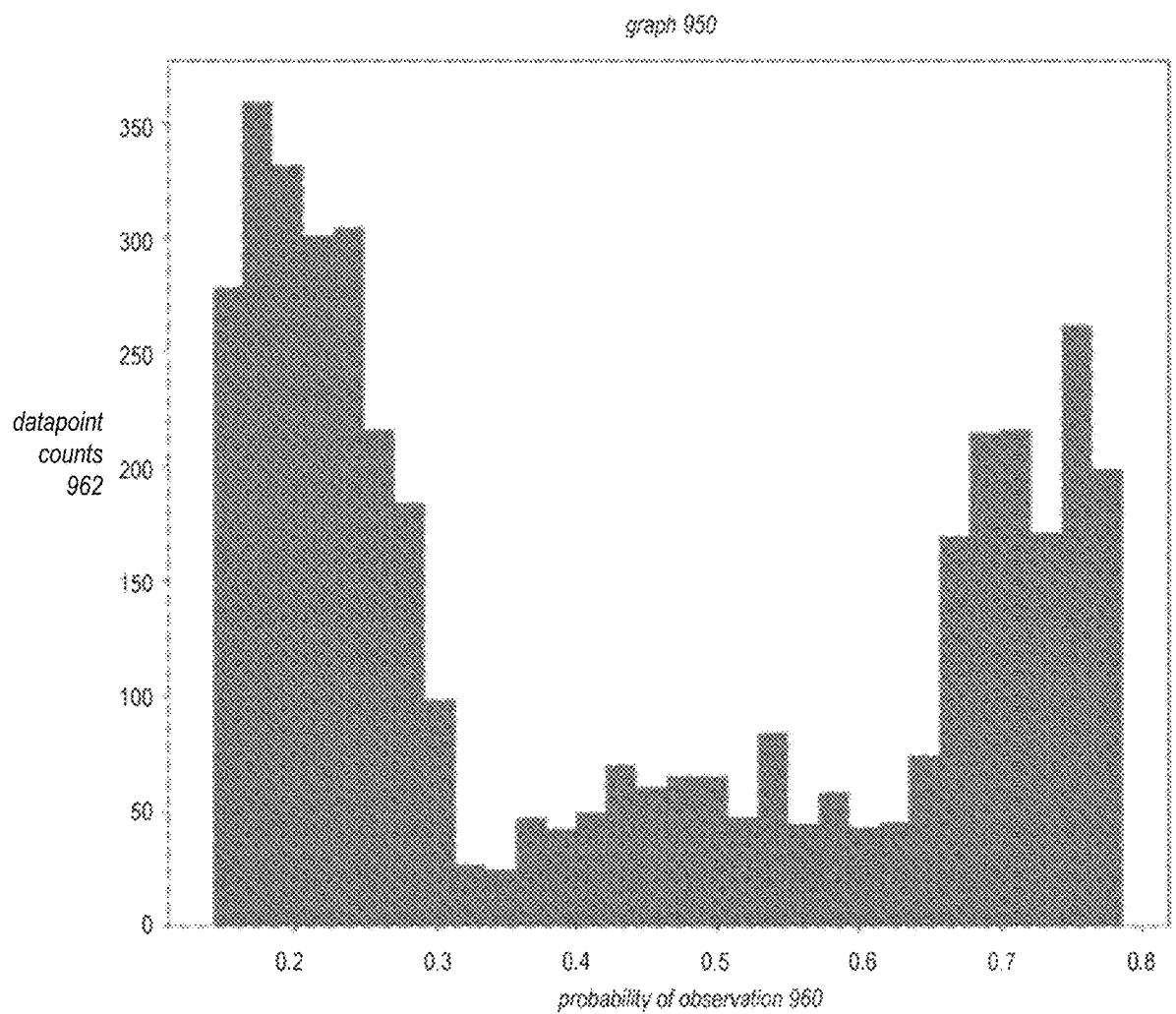
FIG. 9C is a histogram 950 of the probability of observing synthetic data generated by a synthetic data generation system, according to some embodiments.

FIG. 9C shows another histogram 950 of datapoint counts 962 at different density function probability values 960, this time for synthetic datapoints generated using the above-described density estimation technique. As shown in this histogram, the generated synthetic datapoints are closer to the actual datapoints in terms of the density function probability, with some generated datapoints in the 70% range. Moreover, as shown, the generation process may be controlled so that no synthetic datapoints are generated below 10% probability.

Figure 9D:
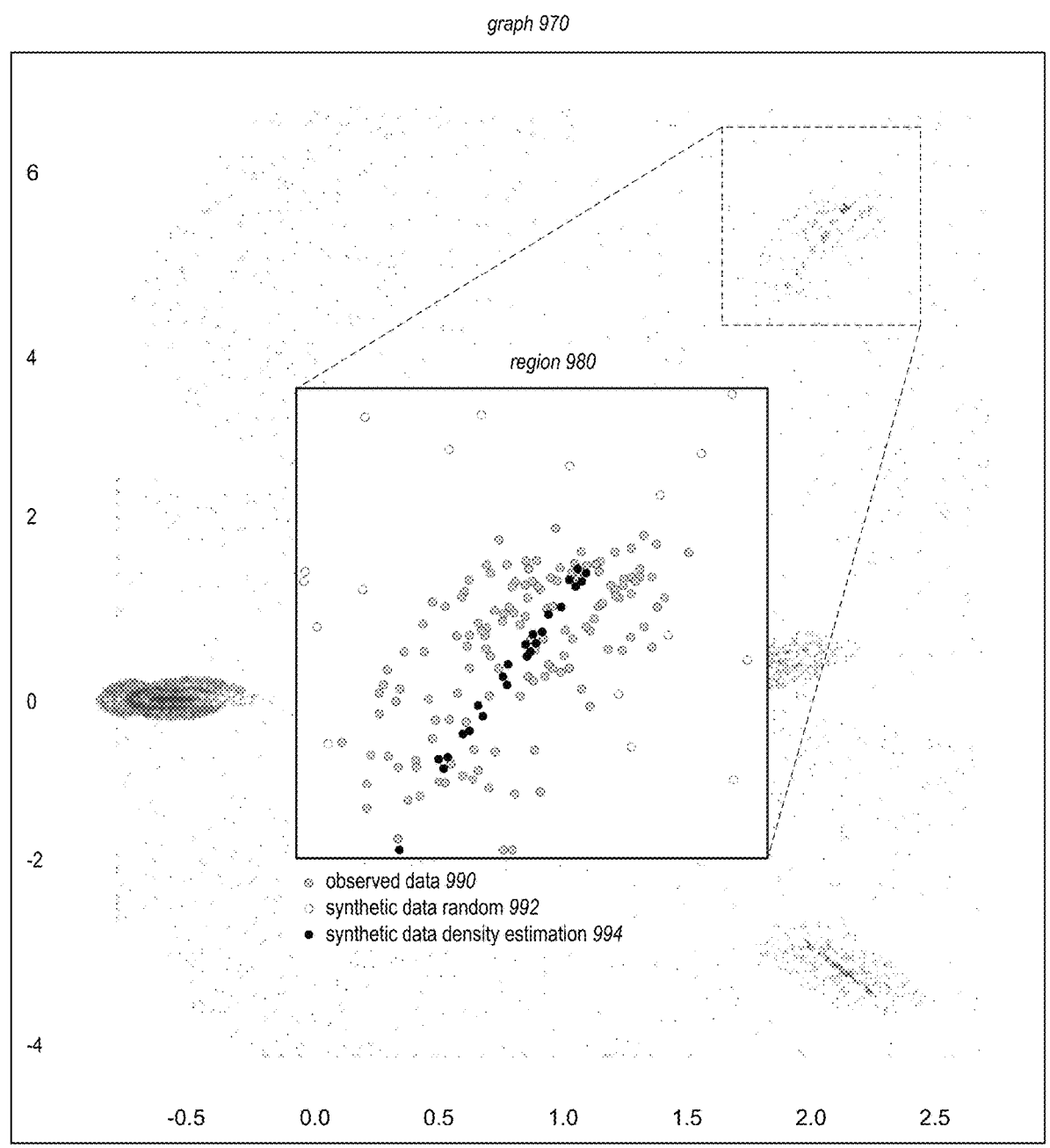
FIG. 9D is a graph 970 showing a plot of real data in an observed dataset, synthetic data generated uniformly at random, and synthetic data generated using a density estimation scheme by a synthetic data generation system, according to some embodiments.

FIG. 9D shows a plot 970 of a feature space with real datapoints of an observed dataset 990, synthetic datapoints generated uniformly at random 992, and synthetic data generated using the above-described density estimation scheme 994. As shown, the feature space here is projected into two dimensions, which may be the first two dimensions determined by a PCA technique. As shown, the plot zooms in on a region 980 of the feature space so that the relative locations of the datapoints may be easily examined. As shown in region 980, the synthetic data generated using density estimation lie much closer to the observed data, making these datapoints better training or testing cases for downstream machine learning models.

Figure 10:
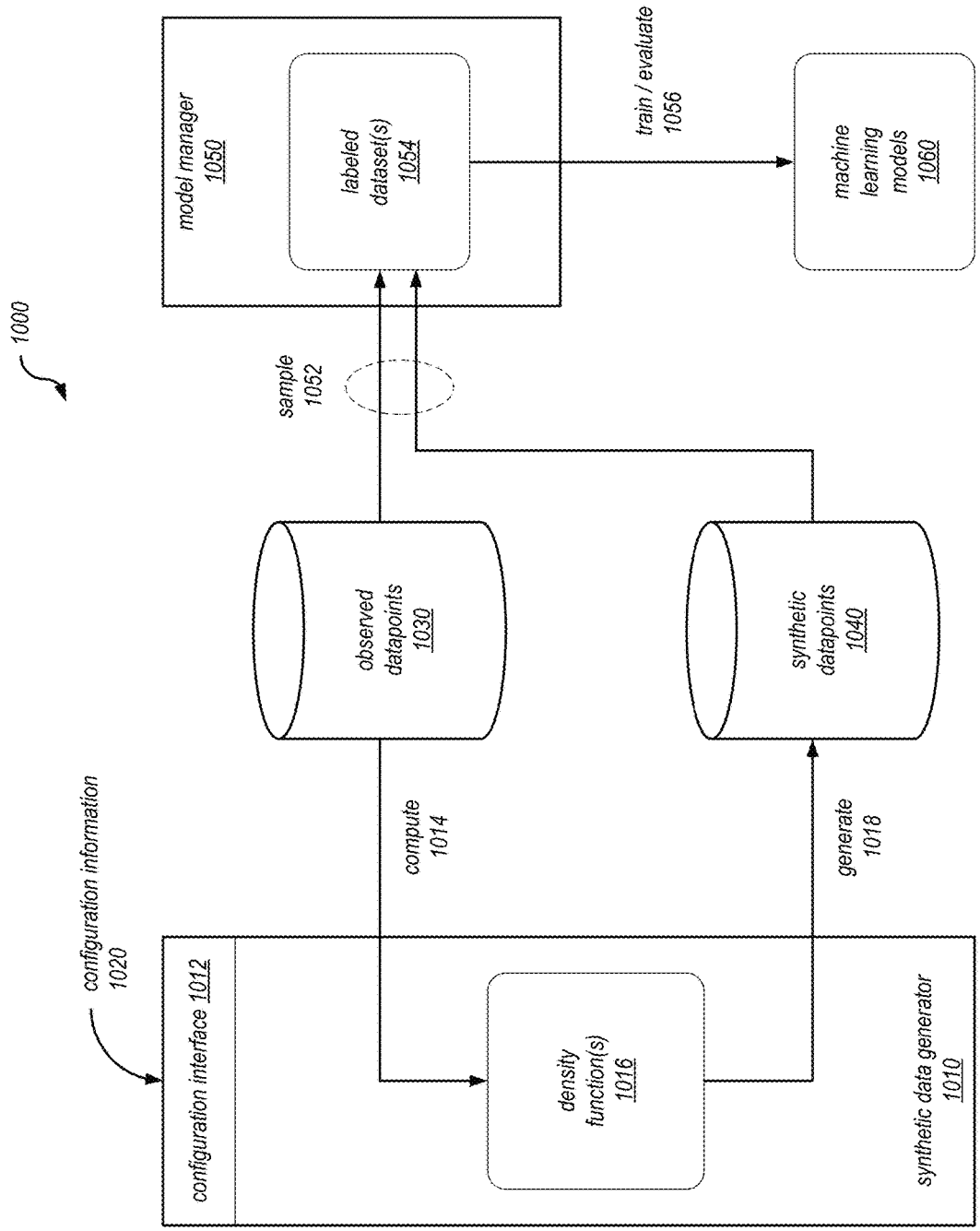
FIG. 10 is a block diagram 1000 illustrating the operations of a synthetic data generation system used in a machine learning anomaly detection system to generate synthetic data for machine learning models, according to some embodiments.

FIG. 10 is a block diagram 1000 illustrating the operations of a synthetic data generation system used in a machine learning anomaly detection system to generate synthetic data for machine learning models, according to some embodiments. In some embodiments, the synthetic data generator 1010 shown in the figure may be used to carry out the synthetic data generation process discussed in connection with FIG. 8.

As shown, in some embodiments, the synthetic data generator 1010 is configured to access a repository of observed datapoints 1030. In some embodiments, these observed datapoints may represent feature vectors that were actually extracted from observation records by the anomaly detection system. In some embodiments, the synthetic data generator 1010 may be configured to periodically access the observed datapoints repository to generate synthetic datapoints into a synthetic datapoints repository 1040. In some embodiments, the repositories 1030 and 1040 may be implemented as the same repository (e.g. a single database or dataset). In some embodiments, the synthetic data generator 1010 may be configured to augment observed data with generated synthetic data, for example, by appending generated synthetic datapoints to the same file containing the observed datapoints.

As shown, the synthetic data generator 1010 may periodically compute 1014 one or more density functions 1016 from the observed data. In some embodiments, the density function 1016 may be estimated for only a recent time window of the observed data. In some embodiments, multiple density functions may be generated, for example, for different clusters or categories seen in the observed data. The density function(s) 1016 are then used to generate 1018 a population of synthetic datapoints, as discussed in connection with FIG. 8.

As shown, in some embodiments, the synthetic data generator 1010 may provide a configuration interface 1012, which may be an interactive interface such as a GUI, or a programmatic interface such as an API or a service interface. The configuration interface 1012 may allow users or other programs to specify configuration information 1020 to control various operational aspects of the synthetic data generator. For example, the configuration information may specify how often (or under what conditions) the synthetic data generator should generate synthetic data. In some embodiments, the configuration information may indicate how to determine the density function. or how to sample the observed datapoints to generate synthetic data. In some embodiments, the configuration information may specify preferred directions or distances for generating synthetic datapoints. In some embodiments, the configuration information may specify constraints for generating synthetic data, such as density function probability bounds, the proportions or amount of datapoints to generate in different ranges, among other types of constraints.

As shown, in some embodiments, a model manager 1050 is implemented to consume the data stored in the observed datapoints repository 1030 and the synthetic datapoints repository 1040. In some embodiments, the model manager 1050 may be configured to perform ongoing training, updating, and/or testing of one or more of the machine learning models 1060 used by the anomaly detection system. As shown in this example, the model manager 1050 may periodically sample 1052 from the two datapoint repositories 1030 and 1040 to create labeled datasets 1054. In some embodiments, the model manager 1050 may automatically label the datapoints according to whether they are observed or synthetic. In some embodiments, the labeling may be performed based on other features of the datapoints. As shown, after the labeled dataset(s) 1054 are created, the model manager may use the dataset(s) to train or evaluate 1056 the machine learning models 1060. For example, the training of these models may be performed as discussed in connection with FIG. 7.

4.4 Anomaly Detection Pipeline

Figure 11:
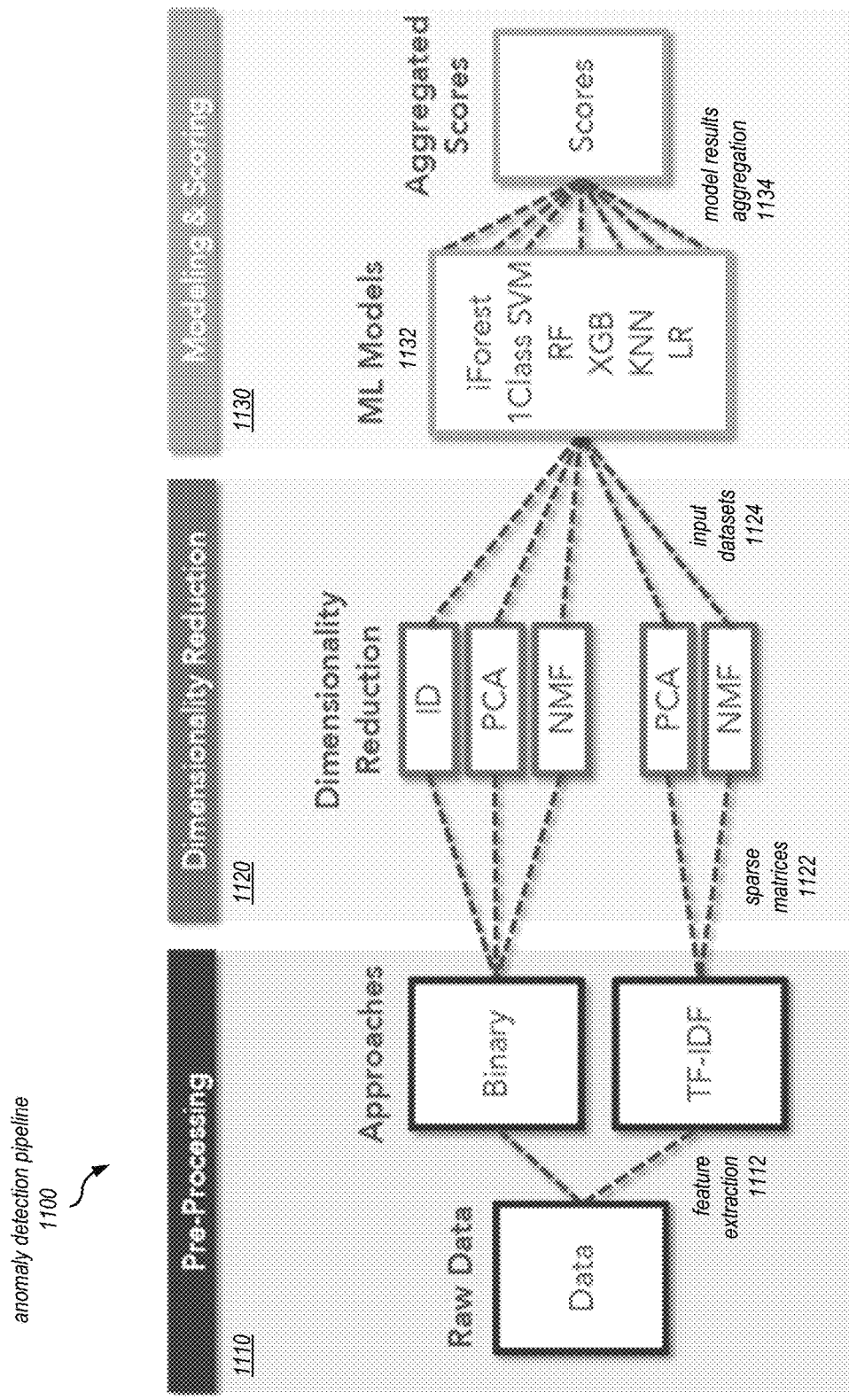
FIG. 11 is a block diagram illustrating an outlier detection pipeline implemented by a machine learning anomaly detection system, according to some embodiments.

FIG. 11 is a block diagram illustrating an example outlier detection pipeline of a machine learning anomaly detection system that is implemented using the techniques discussed previously. In some embodiments, the pipeline 1100 may be implemented by a fleet of computers implemented in a cyberattack monitoring service (e.g. a MDR service). The cyberattack monitoring service may be configured to periodically collect data from a client network and monitor the data for signals of a cyberattack, compromise, or security threat, etc. In some embodiments, the cyberattack monitoring service may be configured to use the pipeline 1100 to programmatically filter regularly received observation data (e.g. once a week), to identify anomalies in the data (e.g. oddly behaving processes or hosts) to be more closely examined by human analysts as part of a hunt process.

As shown in this example, the pipeline 110 is divided into stages, including a pre-processing stage 1110, a dimensionality reduction stage 1120, and a modeling and scoring stage 1130. In some embodiments, the stages are executed sequentially, but not necessarily synchronously. Thus, the completion of one stage in the pipeline does not necessarily cause the next stage to immediately begin execution. Rather, these stages may be performed in a loosely orchestrated manner, which may be controlled via a pipeline manager component (e.g. the anomaly detection pipeline manager 2520 of FIG. 25). In some embodiments, the pipeline manager component may provide a user interface (e.g. a graphical user interface) that can be used by an administrator of the pipeline to view the execution progress of the pipeline, and/or control the execution of the pipeline (e.g. to start, stop, or repeat particular stages in the pipeline).

As shown, the pre-processing stage 1110 begins with raw data, which may be the observation records 130 of processes collected from the client network for a certain observation period (e.g. for a particular week). In some embodiments, the raw data may also include data from other sources, such as intelligence reports from third parties describing known malware, cyberattacks, etc. Such third party data may be used to augment the observed features of the raw data. In some embodiments, the raw data may be reported as logs of process events (e.g. process launch events), which are captured by data collection agents executing within the client network.

As shown, the raw data is converted into feature vectors via feature extraction step 1112. As discussed previously, feature extraction may involve augmenting the features of the observation records with additional features, and then re-encoding the features into a feature vector representation. In some embodiments, the anomaly detection pipeline 1110 may support multiple feature vector representations, such as a binary representation or a TF-IDF representation. In some embodiments, other types of feature vector encodings may also be used. In some embodiments, the anomaly detection pipeline may provide a configuration interface to allow an administrator to select the representation of the feature vectors. In some embodiments, the result of the pre-processing stage may include one or more sparse matrices 1122 of feature vectors (e.g. matrices 200 or 230). In some embodiments, one matrix 1122 will be generated for each category of observation records (e.g. a group of processes having the same executable path). In some embodiments, the matrices may be saved as files at a location that is accessible by the next stage of the pipeline.

As shown, the dimensionality reduction stage 1120 may employ a number of dimensionality reduction techniques, such as PCA, NMF, or an Auto Encoder, etc. In some embodiments, other types of dimensionality reduction techniques may also be used. In some embodiments, these dimensionality reduction techniques may each be associated with a machine learning model, which may be trained using unsupervised learning techniques without the use of labeled data. In some embodiments, the pipeline may allow an administrator to select a particular dimensionality reduction technique via the configuration interface. In some embodiments, the result of stage 1120 will include input datasets 1124 of feature vectors with reduced dimensions, which are ready for use by the outlier detection models 1132 of the next stage.

As shown, the modeling and scoring stage 1130 may be performed using a number of machine learning models, such as Isolation Forest, One-Class SVM, or other classification models trained to distinguish between real and synthetic data. In some embodiments, the models 1132 may be trained using unsupervised learning techniques and without the use of labeled data. In some embodiments, one or more of the models may be trained using programmatically labeled data without human labeling. In some embodiments, each model 1132 will accept input feature vectors from the input datasets 1124 and generate an outlier metric for each input feature vector. The outlier metric may indicate a quantitative measure of how abnormal an observed process or host is based on historical observations. In some embodiments, outlier processes are determined based on historical records of processes in the same process category. In some embodiments, outlier hosts may be determined based on historical records of that host or a similar group of hosts.

In some embodiments, the anomaly detection pipeline may use more than one outlier detection model for each input dataset 1124. For example, each input feature vector may be examined by several machine learned models to obtain a multiple model results, and these results may be aggregated 1134 using an aggregation technique (e.g. a formula or another ML model) to obtain an overall outlier metric or score for the feature vector. In some embodiments, the formula for computing the aggregated score may be configurable by an administrator. In some embodiments, the formula may be automatically adjusted by the anomaly detection system. For example, the weights assigned to individual model results may be periodically tuned by the system based on the recent performance of the models, or based on how far the results of one model deviate from the others.

In some embodiments, the multiple machine learning models 1132 may execute together as a single ensemble. Depending on the embodiment, various result aggregation strategies 1134 may be employed for the ensemble. For example, in some embodiments, the aggregated score may represent a weighted average of scores produced by the constituent models. In some embodiments, the aggregation may ignore the highest and/or lowest scores produced by the constituent models. In some embodiments, a voting scheme may be used where the constituent models cast votes for a particular observation to be designated as an outlier. In some embodiments, the aggregation may be performed by an aggregator model, which may be trained (e.g. using unsupervised techniques) to combine results from the constituent models to generate the aggregated outlier score.

In some embodiments, the models 1132 may be used to produce outlier scores for each observation record that is relative to other records in the observation record's category (e.g. category 120). Thus, for example, to detect an outlier score for a MICROSOFT EXCEL process, that particular process is compared to all "normal" historical processes of MICROSOFT EXCEL seen by the model. In some embodiments, observation records of hosts may also be categorized based on a combination of characteristics of the hosts. In some embodiments, at least some of the models 1132 may be trained (e.g. using supervised training techniques) to generate scores for observation records that are based on historical examples of attacks. In some embodiments, the anomaly detection system may implement different sets of models for each observation category.

In other embodiments, the anomaly detection system may use the same models for all observation categories, but use statistical techniques to generate an outlier score that is specific to each category. For example, the system may use a single model to produce raw outlier scores for all observation categories. However, a raw outlier score may then be ranked against only the scores of observations in the same category, to obtain a percentile ranking of the observation within the category. In some embodiments, the outlier scores may be normalized (e.g. reduced to a value between 0 and 1) so that they can be compared across all categories. In some embodiments, detected outliers for each category may be ranked, and only a specified number of highest ranked outliers are outputted as detected anomalies (e.g. anomalous processes or hosts). In some embodiments, the manner that the aggregated score is calculated may be configurable using a configuration interface of the anomaly detection system.

It will be appreciated that security analysts in modern SOCs deal with a massive amount of data and have to cull through this data to find intrusions and anomalies. The anomaly detection pipeline disclosed herein may be used to reduce the analysts' work during the hunt process. For example, the anomaly detection system may be configured to tag 95% of incoming observation records as normal and 5% as anomalous, leaving this 5% to be the focus of investigations and further action by analysts. In this manner, the time and resources that security analysts spend on hunt analysis is significantly reduced.

It will also be appreciated that in some embodiments, the anomaly detection pipeline may be used for other types of data analysis. For example, in some embodiments, the disclosed pipeline can be used to analyze collected data for vulnerability management, incident detection and response, security workflow generation for automation and orchestration, penetration testing, application security testing, and a variety of other operations of a cyberattack monitoring service.

Figure 12:
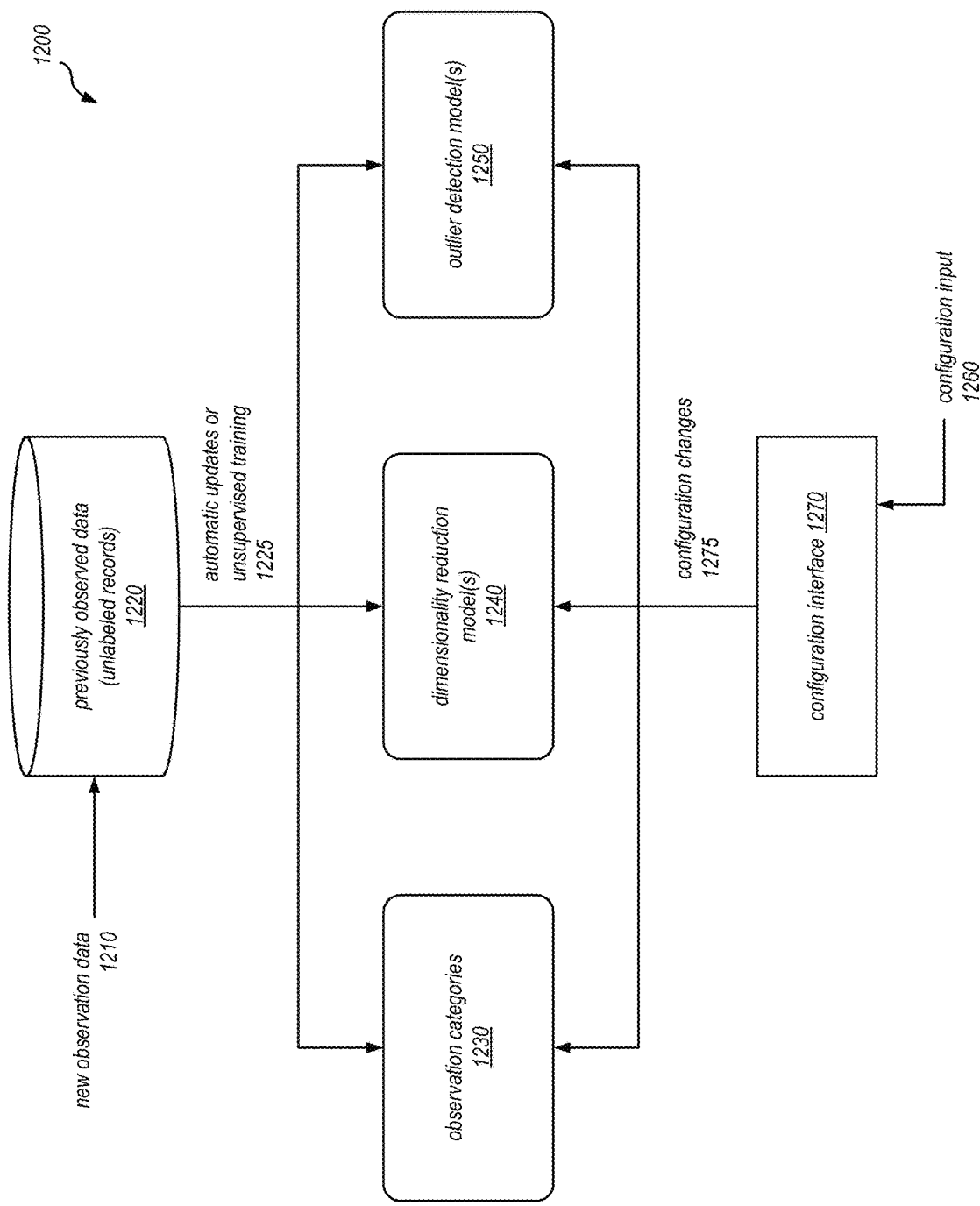
FIG. 12 is a block diagram 1200 illustrating automated updating of components of the machine learning anomaly detection system, according to some embodiments.

FIG. 12 is a block diagram 1200 illustrating automated updating of components of the machine learning anomaly detection system, according to some embodiments.

As shown, the figure depicts the automated updating of a number of pipeline components, including observation categories 1230 (e.g. categories 120 of FIG. 1A), dimensionality reduction models 1240 (e.g. the dimensionality reduction models discussed in connection with FIG. 4A), and outlier detection models 1250 (e.g. the ML models 1132 of FIG. 11). In some embodiments, all of these components may be automatically updated or trained 1225 based on new observation records 1210 collected from client network(s).

As shown, in some embodiments, new observation records 1210 collected for an new observation period (e.g. hunt data including process observation records) may be stored in a data store 1220. The data store 1220 may store an archive of previously observed data about host behavior. In some embodiments, this observation data is unlabeled for machine learning purposes (e.g. the data are not designated with truth labels indicating records as outlier or non-outlier observations). In some embodiments, the previously observed data 1220 may be organized by observation category.

In some embodiments, the previously observed data 1220 may only contain "normal" observations that were not later determined to be associated with cyberattacks. For example, in some embodiments, if a process is later confirmed to be part of a cyberattack after human review, that process may be removed from the data store 1220, so that the models of the anomaly detection system are not trained to identify such a process as a "normal" observation. In some embodiments, processes or hosts that are confirmed to be associated with cyberattacks and/or intrusions may be archived in a different database. In some embodiments, the feature vectors of such processes or hosts may be used to scan future observation data to programmatically detect similar attacks or intrusions. In some embodiments, archived incidents of attacks may be used as examples of anomalies or further leveraged to create synthetic data in their vicinity.

As shown, the observation categories 1230 may be periodically updated using the previously observed data 1220. For example, when new software (e.g. new executables) is installed on hosts in the client network, additional observation categories (e.g. categories based on paths of the executables) may be automatically generated. In some embodiments, the observation categories may be machine learned classes or aggregate data structures, and these classes or data structures may be periodically relearned or updated using recent observations. In some embodiments, when the observation categories 1230 are changed, an update of some or all of the downstream models may be triggered.

As shown, the dimensionality reduction models 1240 may also be periodically updated or trained 1225 using unsupervised learning techniques. For example, a set of dimensions determined by a PCA dimensionality reduction technique may be periodically updated based on a sample of recent data stored in the data store 1220. Such periodic adjustments to the dimensionality reduction models 1240 will ensure that the rest of the anomaly detection pipeline uses the best features for detecting outliers in the data. In some embodiments, changes in the dimensionality reduction models will also cause downstream models such as the outlier detection models 1250 to be updated.

As shown, in some embodiments, the outlier detection models 1250 may also be periodically updated or trained 1225 using unsupervised learning techniques. For example, an Isolation Forest model may periodically be regenerated to adapt to new features in newly observed data. In some embodiments, the outlier detection models may also be periodically evaluated using automated model evaluation techniques (e.g. using model evaluator 2528 of FIG. 25). Model updates may be triggered based on the results of these evaluations.

In some embodiments, the observation categories 1230, dimensionality reduction models 1240, and outlier detection models 1250 may be updated via configure settings received via a configuration interface 1270 of the anomaly detection system. In some embodiments, the manner in which these components are automatically updated are also controllable via the configuration interface. In some embodiments, the configuration interface 1270 may be provided as a web-based GUI configured to receive configuration input 1260 from an administrator. The configuration interface will translate the configuration input 1260 into configuration changes 1275 for the management subsystems for each of the pipeline components. In some embodiments, the configuration input 1260 may specify the schedule of the automatic updates or conditions that will trigger pipeline component updates. In some embodiments, the configuration input may explicitly define specific observation categories (e.g. combining multiple executable paths into a single category, and which execution paths to be ignored, etc.). In some embodiments, the configuration input may specify which dimensionality reduction models are to be used, and the number of features that will be retained in the input datasets. In some embodiments, the configuration input may specify which outlier detection models will be used under what conditions, and how the results of the outlier detection models will be aggregated to determine the ultimate outlier metric for an observation.

It will be appreciated that while the configuration interface 1270 allows humans to control certain behaviors of the anomaly detection system when desired, the system does not require any human input to perform the automatic updates 1225. That is, embodiments of the anomaly detection system are capable of making self-adjustments based on the incoming observation data in a completely unsupervised manner. Accordingly, the anomaly detection system is designed to automatically and continuously learn from new observation data without human input.

Figure 13:
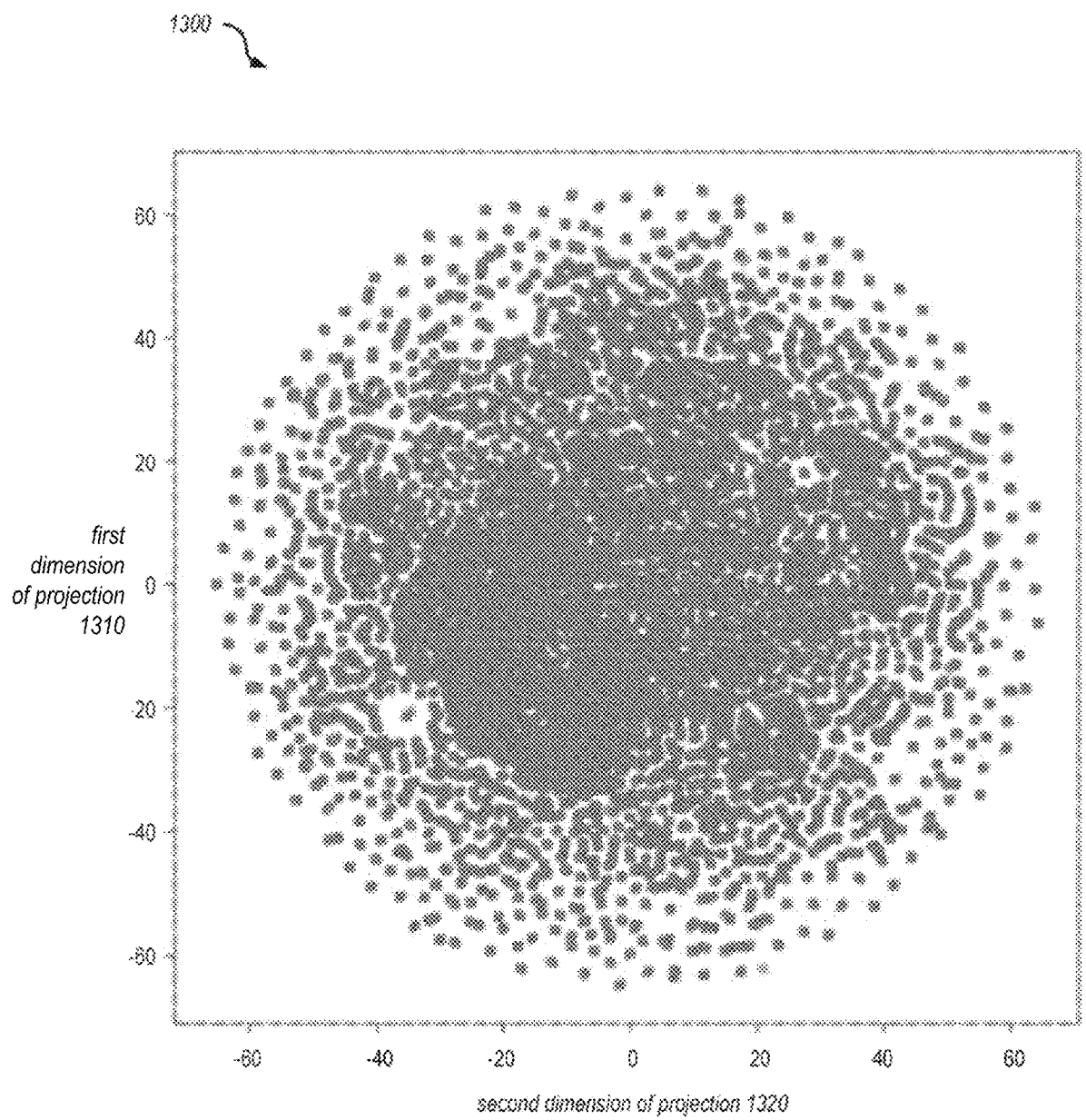
FIG. 13 is a graph 1300 that illustrates a projection of process datapoints analyzed by a machine learning anomaly detection system, according to some embodiments.

FIG. 13 is a graph 1300 that illustrates a projection of process datapoints analyzed by a machine learning anomaly detection system, according to some embodiments. In one study, when the anomaly detection pipeline 1100 was applied on a real dataset, scores are obtained on each host of a client network for a hunt. The datapoint for each process on each host are projected into a two-dimensional space for visualization purposes (e.g., as shown in FIG. 13). As shown in the figure, the datapoints are projected into dimensions 1310 and 1320 in the two-dimensional space, as determined using T-distributed Stochastic Neighbor Embedding (t-SNE). As shown in the graph 1300, there is high density in the center of the graph that decreases toward the edge of the graph, which indicates that most of the observed processes exhibit fairly common behavior, with only a few outliers. In some embodiments, the anomaly detection system may implement a graphical user interface that provides the results of graph 1300 as an aid to security analysts in the hunt process.

In one study, an embodiment of the anomaly detection system was able to identify from actual data anomalous processes that were indicative of: (1) unregistered software to control a given computing device from another malicious computing device, (2) software to move a mouse (or other pointing device) automatically (e.g., a potential security breach), and (3) data transfer software making connections to a malicious external entity (e.g., an exfiltration), among other types of attacks and security incidents.

5. Pipeline Testing Using Synthetic Data

In certain embodiments, given the lack of labeled data, the anomaly detection pipeline is configured to evaluate its models by generating synthetic observation data. In some embodiments, the synthetic data are generated to mimic different scenarios of actual observation data.

5.1 Scenarios
5.1.1 Scenario 1

Figure 14:
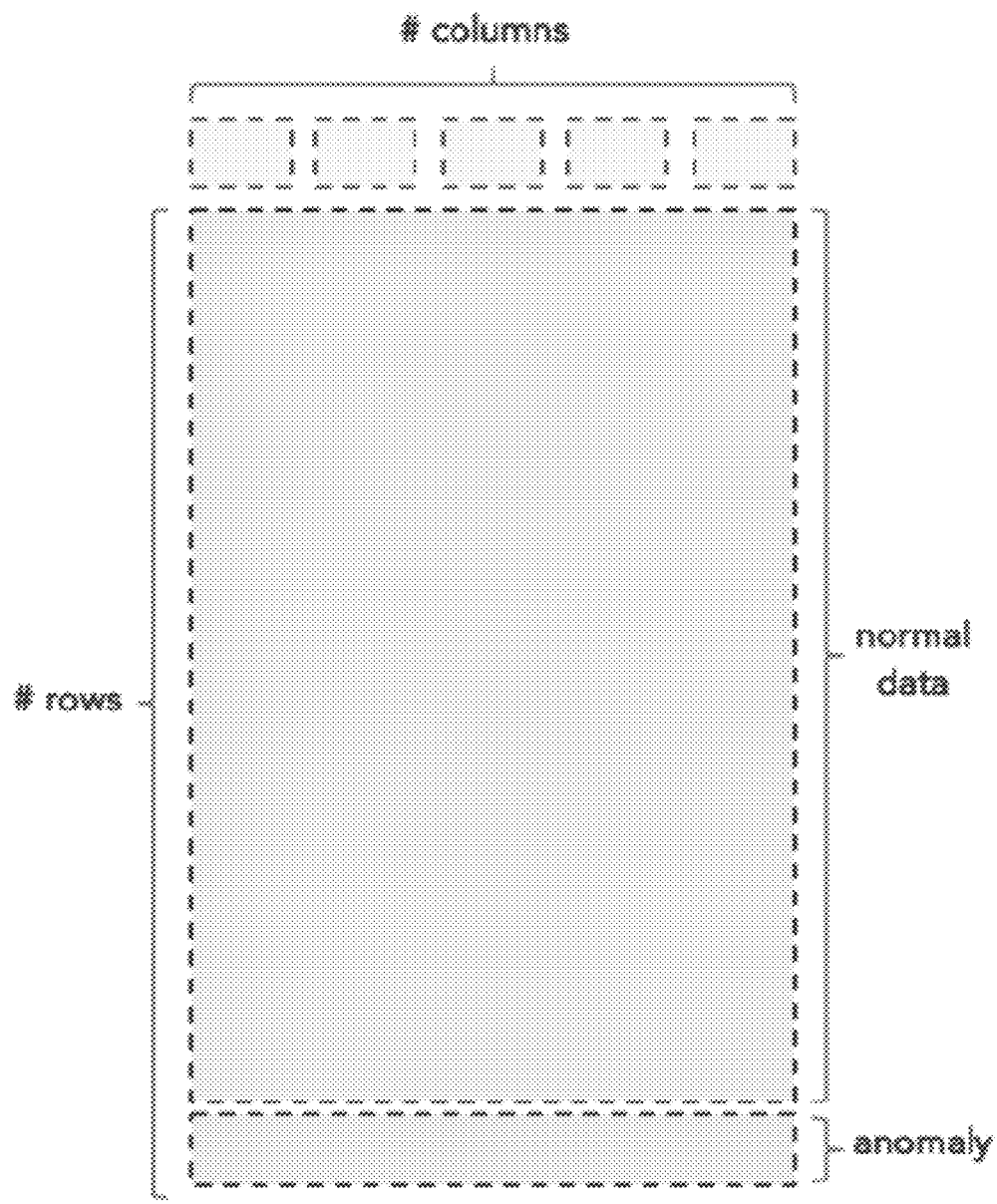
FIG. 14 is a block diagram 1400 of a first scenario of using synthetic data to evaluate models in a machine learning anomaly detection system, according to some embodiments.

In Scenario 1, shown in FIG. 14, n is the number of observations and k is the number of features that are denoted as $e_i=(0, \ldots 0, 1, 0, \ldots, 0)$ are the canonical base of $\mathbb{R}^k$. This provides (or generates) the following matrices:

$$X_i = \begin{pmatrix} e_i \\ \vdots \\ e_i \end{pmatrix}$$

of size $h_i$ such that $$\sum_{i=1}^{k-1} h_i = n - 1$$

and $h_i > \min(0.01*n, 100)$.

In turn, the following matrix is built and/or generated:

$$X = \begin{pmatrix} X_1 \\ \vdots \\ X_{k-1} \\ e_k \end{pmatrix}$$

In one embodiment, each row will be only one 1, while the rest of the columns are 0. In this example, prior to shuffling the rows, the last row will be the anomaly, where all columns except the last column will be 0s. Overall, this scenario tests whether or not the machine learning models can identify anomalies in an idealized context.

5.1.2 Scenario 2

Figure 15:
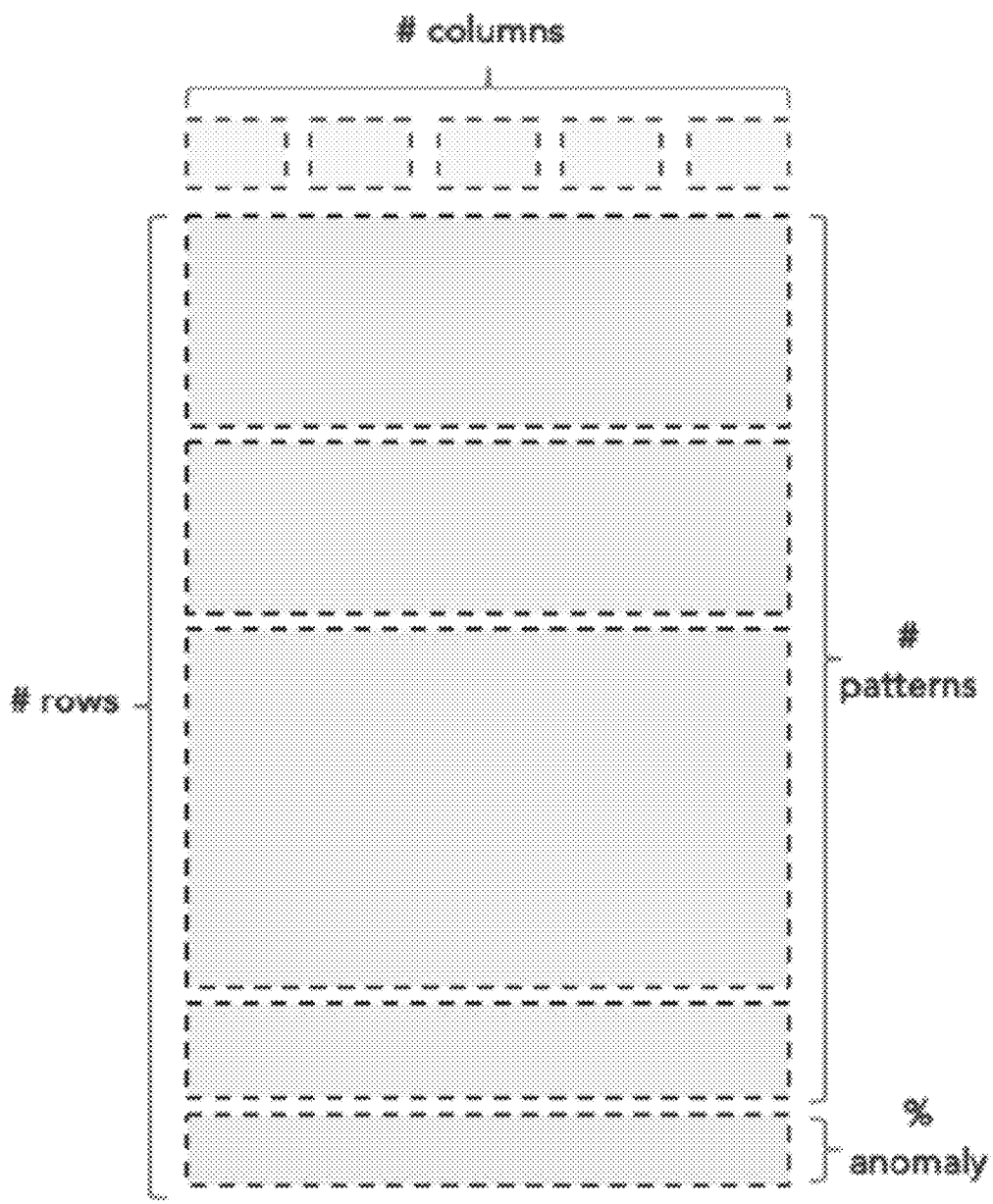
FIG. 15 is a block diagram 1500 of a second scenario of using synthetic data to evaluate models in a machine learning anomaly detection system, according to some embodiments.

In Scenario 2, shown in FIG. 15, the complexity over Scenario 1 is increased by allowing multiple features to be non-zero for each row. A fixed set of unique patterns $(p_1, \ldots, p_m)$, $m \geq 0$ are created such that:

$$\mathbb{P}\left(p[i] = \frac{s}{i^3}\right)$$

where $$s = \sum_i \frac{1}{i^3}.$$

Then, as in Scenario 1, the fixed set of unique patterns are stacked with associated frequencies $h_1, \ldots, h_m$.

Finally, an anomaly a is generated (e.g., a chosen percentage of total amount of data, n) and the difference from previous patterns is measured:

$$\delta = \min(\|a-p_1\|_1, \ldots, \|a-p_m\|_1)$$

Overall, Scenario 2 tests the sensitivity of the unsupervised anomaly detection models to detect anomalies within varying data. However, it is noted that in other embodiments, the probability function may be different.

5.1.3 Scenario 3

Figure 16:
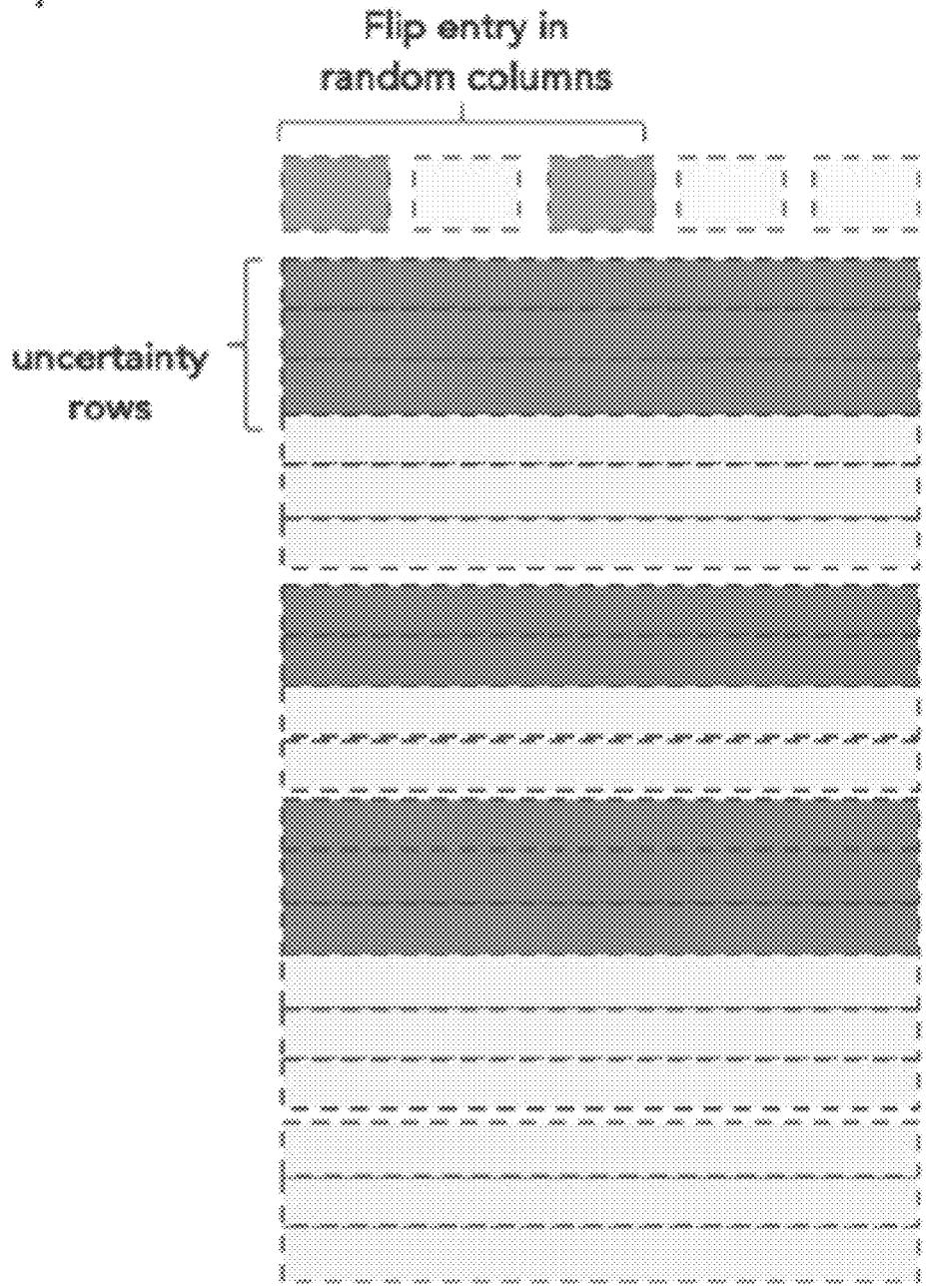
FIG. 16 is a block diagram 1600 of a third scenario of using synthetic data to evaluate models in a machine learning anomaly detection system, according to some embodiments.

In certain embodiments, Scenario 3, which is shown in FIG. 16, builds on the complexity of Scenario 2 by injecting a level of uncertainty into the data. In this context, uncertainty involves flipping 0s to 1s (or vice versa) within generated patterns.

As in Scenario 2, a fixed set of unique patterns are first generated, which accounts for the non-anomalous data. Then, within each pattern, uncertainty is injected by selecting a number of rows (0% to 100%), and choosing different columns in each selected row to flip (0 to 1, 1 to 0). This allows patterns to generally maintain their construct, while adding noise, which can make it more difficult for the models to detect anomalies.

Lastly, an anomaly a is generated again, represented as a percentage of the total data, and difference from other patterns is measured. Overall, this scenario tests for the robustness of the anomaly detection models to find signal within noisy data.

5.2 Scenario Analysis

Given the foregoing three scenarios simulated by synthetic data, a number of different types of analysis are disclosed below to comprehensively test the data. However, as will be appreciated by those skilled in the art, other strategies may be employed in other embodiments to test the pipeline. As just one example, the testing scenarios could be encoded using continuous rather than binary features. Continuous data would allow for more complex analysis of the anomaly detection pipeline, for example, to determine whether the pipeline is able to detect outliers of normal points generated following a multi-dimensional Gaussian, among other types of analysis.

5.2.1 Base Case Analysis

Figure 17:
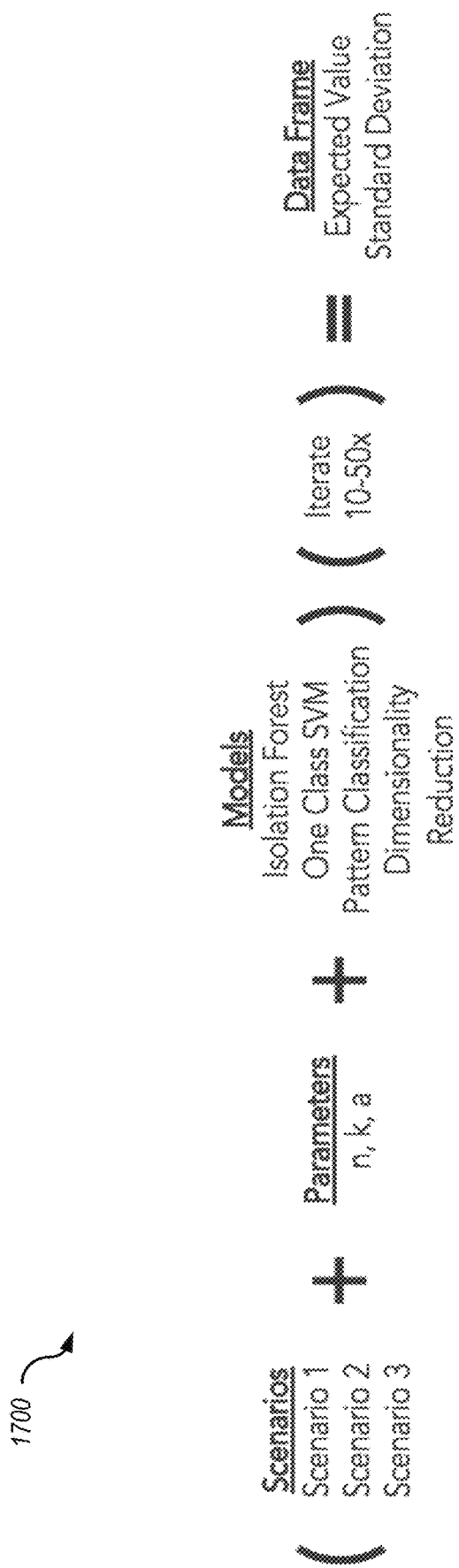
FIG. 17 is an illustration 1700 of a base case analysis performed using synthetic data to evaluate models in a machine learning anomaly detection system, according to some embodiments.

In the base case, as shown in FIG. 17, a combination of the following is contemplated to comprehensively understand how different models perform across different scenarios and across differing parameters. In this example, Scenarios will be isolated from each other (e.g., scenarios will not be combined with each other, at least in the base case):

Scenarios
    Scenario 1
    Scenario 2
    Scenario 3
Parameters
    Number of rows (n)
    Number of features (k)
    Number of anomalies (a)
Algorithms/Methodologies
    Isolation Forest
    One-Class SVM
    Bootstrap—Random Forest
    Bootstrap—XGBoost
    Bootstrap—SVM
    Bootstrap—Logistic Regression
    Bootstrap—K Nearest Neighbors For example, in one embodiment, Scenario 1 is selected, a specific n, k, and a is chosen, an algorithm (for those noted above) is selected, and the foregoing combination is run or executed between 10 and 50 times to extract an expected value (E) and standard deviation (s). Next, a range of scenarios, parameters, and algorithms are selected to be able to construct a view into unsupervised anomaly detection model performance. The output of this process results in a large data frame with all permutations of the above. Linear regressions are then run to determine how different elements impact the overall score of the models.

5.2.2 Mixed Scenario Analysis

In the mixed scenario analysis, the performance of models is tested with data generated with any combinations of scenarios and parameters. This contrasts from the data generated from the base case in that different scenarios are mixed together.

For example, n and K (the number of blocks that make up different scenarios can be fixed). Next, a list of scenarios matching the number K is created, where the scenarios from 1-3 (above) can both include or exclude anomalies. Each of these scenarios will be associated with its own k (number of features) and p (% anomaly).

In the above example, each list of different scenarios applied on each algorithm outputs a variable, phi, where 1 means a model detected the anomaly, and 0 means that the anomaly was not detected by the anomaly detection model. By creating a sampling across many different combinations of scenarios, a linear/logistic regression can be executed/run to determine what elements lead to better detection of anomalies.

5.2.3 Model Aggregation Analysis

Figure 18:
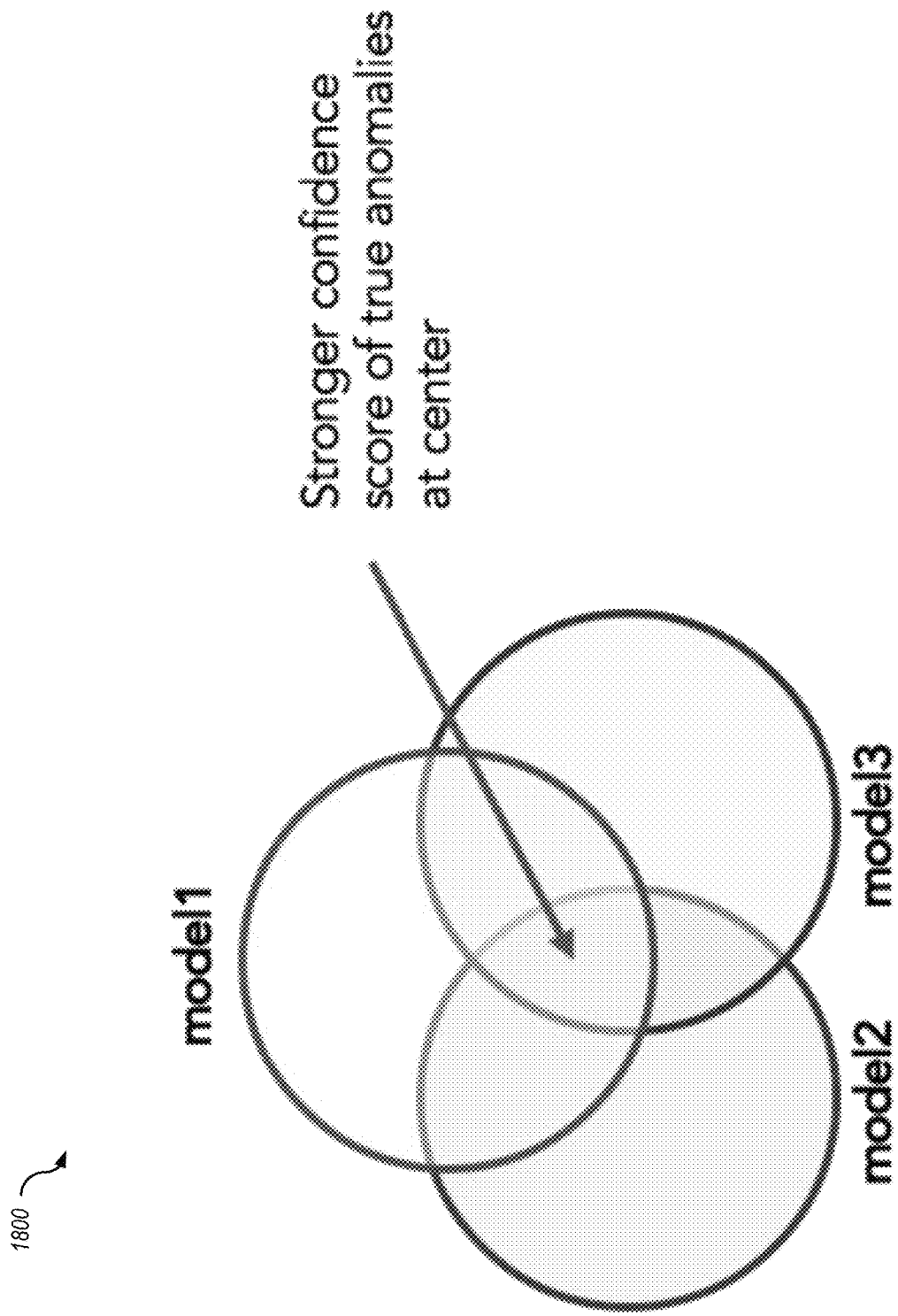
FIG. 18 is an illustration 1800 of a model aggregation analysis performed using synthetic data to evaluate models in a machine learning anomaly detection system, according to some embodiments.

In certain embodiments, in the model aggregation or ensembling analysis, as shown in FIG. 18, specific anomalies that one or more of the algorithms are able to detect across a fixed number of scenarios are analyzed. In this example, the goal is to figure out if and which algorithms are picking up (or identifying) the same anomalies in a given scenario.

When extrapolating this exercise to real data and by using multiple models to identify anomalies, confidence in what looks anomalous when greater than a threshold of algorithms are identifying them is significantly strengthened (e.g., as shown in FIG. 18).

5.2.4 Anomaly Distance Analysis

In some embodiments, in the anomaly distance analysis, a security analyst can understand how the distances of anomalies from normal data affects the algorithms' abilities to detect them. In this example, the hypothesis is that greater distance would increase chances of identifying the anomalies. By running this exercise, the foregoing hypothesis can be validated by generating a comprehensive set of synthetic data.

In other embodiments, distance can be an additional feature to be analyzed in the base case. Therefore, the methods, systems, and processes disclosed herein facilitate unsupervised anomaly detection in cybersecurity computing environments (e.g., by generating several anomaly detection (ML) models for anomaly identification in data).

5.3 Results
5.3.1 Scenario 1

Figure 19:
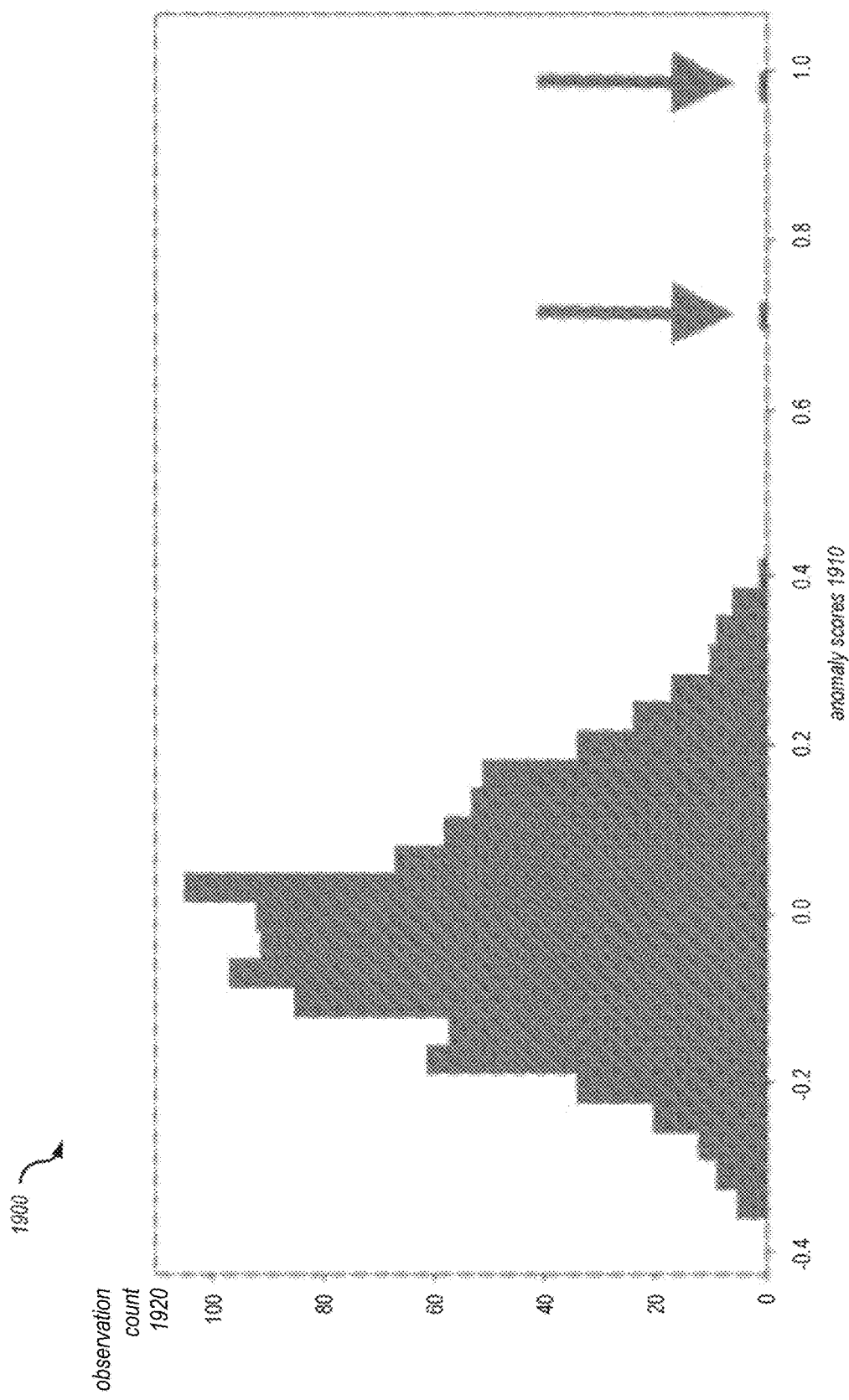
FIG. 19 is a graph 1900 showing two anomalies detected during model evaluation using synthetic data in a machine learning anomaly detection system, according to some embodiments.

For the Base Case in Scenario 1, and in certain embodiments, synthetic data is run to capture the results across different sample sizes and different number of features (e.g., sample size ranged from [100, 5000] and number of features ranged from [2, 18]). Having generated synthetic data for Scenario 1, it is determined that a significant portion of the models perform as expected. It should also be noted that the foregoing experiment is performed with uniformly random fake data, although other models may improve results in high-dimension. FIG. 19 illustrates the models' ability to identify outliers determined using this evaluation strategy (n=1000, k=87). FIG. 19 depicts a histogram of anomaly scores, where the x-axis 1910 is the normalized anomaly scores, and the y-axis indicates an observation count in each score bucket.

Figure 20:
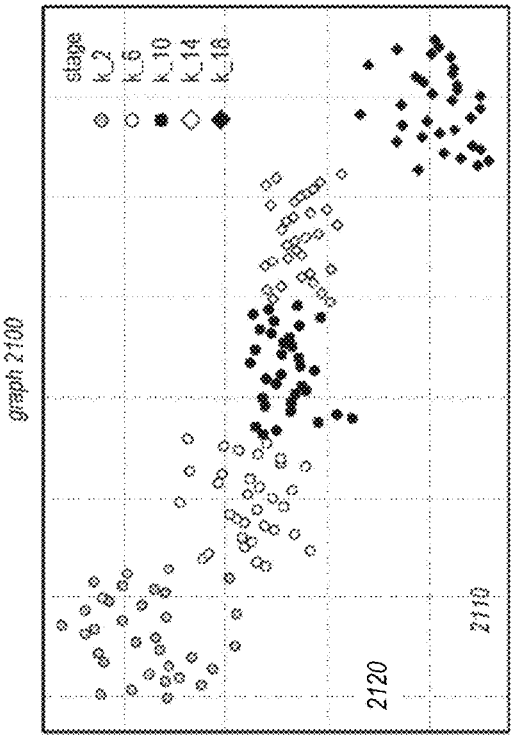
FIG. 20 is a graph 2000 that illustrates anomaly scores for Isolation Forest as determined during model evaluation using synthetic data, according to some embodiments.
Figure 21:
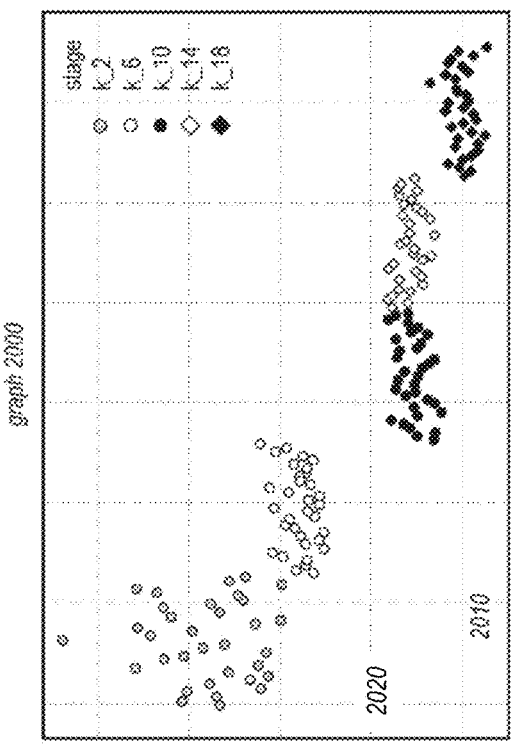
FIG. 21 is a graph 2100 that illustrates anomaly scores from Bootstrap Random Forest as determined during model evaluation using synthetic data, according to some embodiments.
Figure 22:
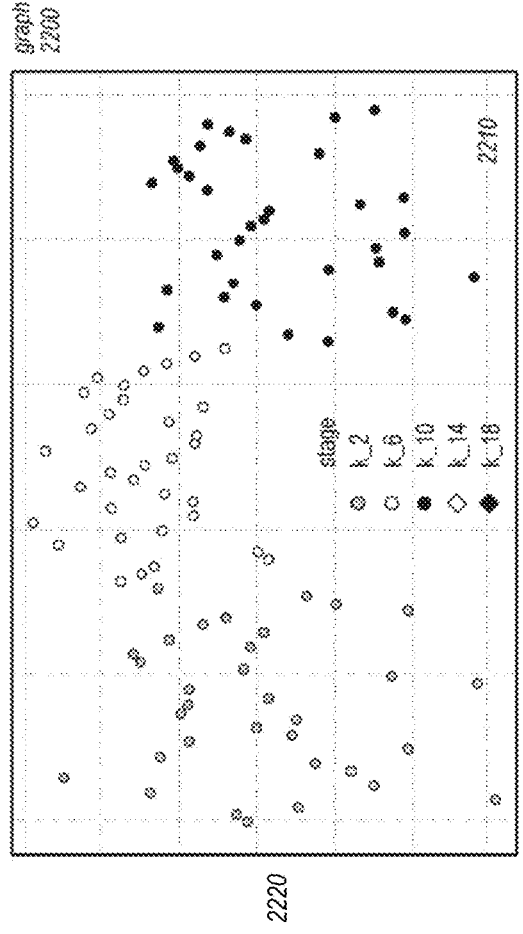
FIG. 22 is a graph 2200 that illustrates anomaly scores from Bootstrap KNN as determined during model evaluation using synthetic data, according to some embodiments.

Regarding specificity of the different models in Scenario 1, FIG. 20 illustrates the results for Isolation Forest, FIG. 21 illustrates the results for Bootstrapped Random Forest, and FIG. 22 illustrates the results for Bootstrapped KNN to show the varying performances across models, as well as across the number of features. In these graphs, the x-axis 2010, 2110, and 2210 represent the dimensionality of the data, the y-axis 2020, 2120, and 2220 represent the anomaly scores of the from the models as determined during model evaluation.

It should be noted that performance of the model(s) may decrease as the number of features increase. Looking specifically at Isolation Forest, this model can detect anomalies when the number of features is low, but performance can drop as the number of features reaches k=18. However, this drop makes sense due to the nature of Isolation Forest (e.g., because an Isolation Forest is made up of numerous Isolation Trees, each of which take a random sampling of features; as the number of features increase, it can become increasingly rarer for an Isolation Tree to pick up the one column that defines the anomaly).

In one embodiment, the Bootstrapped Random Forest produces stronger performances across each count of features compared to other models. This differs from the Isolation Forest model because the process of bootstrapping turns the problem into a classification problem, which Random Forest performs well in.

In some studies, Bootstrapped KNN does not perform as well as Isolation Forest or Bootstrapped Random Forest. Therefore, it should be noted that clustering may be less preferred for finding, detecting, and identifying anomalies, in some embodiments.

Detection Rate: Executing the unsupervised anomaly detection pipeline on earliest on synthetic data under Scenario 1 discussed above achieves a 85% detection rate at $2\sigma$ from the mean. It is contemplated that the effectiveness of the unsupervised anomaly detection pipeline can also be established under Scenarios 2 and 3 discussed above under more complex simulations.

6. Model Interpretability

In certain embodiments, model interpretability is important to cybersecurity solution providers. However, because of the complexity of the unsupervised anomaly detection model and the ensemble approach used, direct interpretability can be a challenging technological problem. Therefore, the following two methodologies are presented to add interpretability to final anomaly scores.

6.1 Sparse Linear Regression

In one embodiment, the process for performing sparse linear regression includes: (1) execute the model against client data to obtain anomaly scores, (2) execute sparse linear regression with 10% sparsity against final anomaly scores on original features, and (3) use feature importance to explain what impacts anomaly scores and generate an impact report of missing or present values.

6.2 Individual Anomaly Score

In certain embodiments, an anomaly detection model can be trained individually for each feature, leading to a personalized anomaly score for each feature for each process. In this manner, a security analyst in a SOC can merely observe the scores and determine the reasons as to why a given process was deemed anomalous.

6.3 Anomalous Interaction Among Variables

For example, if a process P has two features A and B—whenever A takes value 1 and B takes value 0 and vice-verse—a process with both features to 0 would be an anomaly; however, both features would not be considered anomalies individually. Therefore, to explain anomalous interaction among variables, in one embodiment, an interpretability layer is implemented to explain such interactions (e.g., using a tree based approach).

7. Anomaly Detection Pipeline for Identifying Anomalous Processes or Hosts in Hunt Data Analyzing metadata about processes in a computer network can be an effective method to identify compromised machines, assets, devices, and the like. Unfortunately the enormous volume of process-related data makes existing and traditional approaches of analyzing the data difficult from a technological standpoint. Accordingly, to address these and other problems in the state of the art, a machine learning anomaly detection system is disclosed to detect outlier processes or hosts to be prioritized for human investigation. In some embodiments, the machine learning models used by the system are trained using unsupervised machine learning methods, so that the data for training and testing models do not need to be manually labeled.

Figure 25:
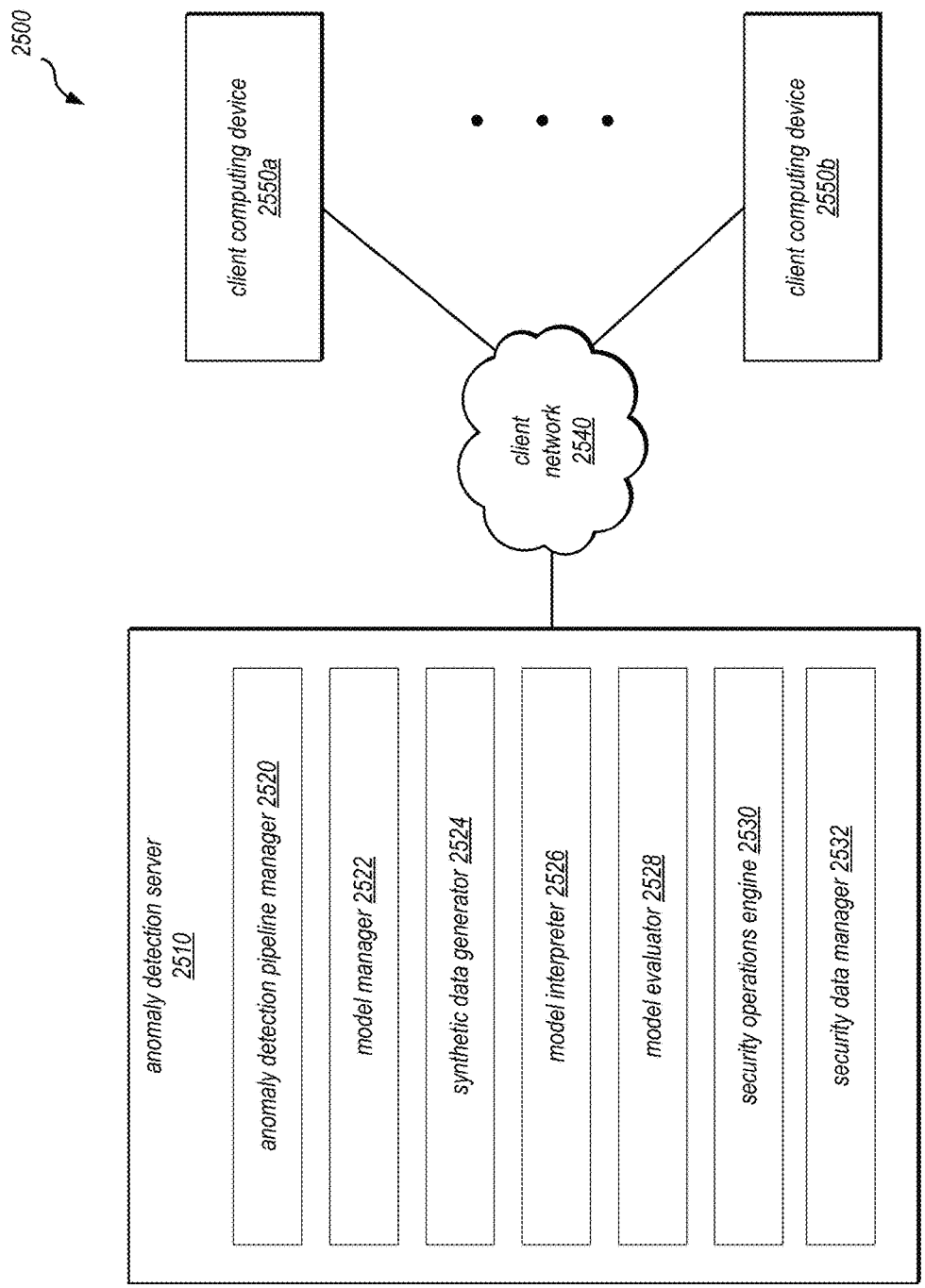
FIG. 25 is a block diagram 2500 of an anomaly detection server used to implement a machine learning anomaly detection system, according to some embodiments.

In some embodiments, the anomaly detection system may be implemented using one or more anomaly detection servers 2510, as shown in FIG. 25. For example, the anomaly detection server 2510 may implement an anomaly detection pipeline manager 2520 that implements the pipeline 1100 as shown in FIG. 11. In some embodiments, the anomaly detection pipeline addresses the unique technical challenges the hunt process, and is configured to detected outliers in the hunt data by performing: (1) a normalizing step to remove small variations in the data (e.g. in the naming of the processes), (2) a dimensionality reduction step to reduce the very large dimensionality of the data (e.g. number of possible processes), and (3) a modeling and scoring step to aggregate results from multiple machine learning models to generate an outlier metric for an observed process or host. In some embodiments, the anomaly detection pipeline manager 2520 may compute and determine an anomaly score using an ensemble of independent machine learning models and aggregates the results. The aggregated scores may be used as the metrics for assigning priority for a security analyst (e.g., in a SOC) to investigate the detected anomalies for further action (e.g., to be performed by the security operations engine 2530).

In certain embodiments, the anomaly detection pipeline manager 2520 may be implemented to perform at least the following operational steps: (1) access or receive raw data for multiple distinct processes (e.g., software processes) executing or running across multiple distinct hosts, (2) perform pre-processing (e.g., binarization or TF-IDF encoding of the data), (3) perform dimensionality reduction (e.g., using PCA, NMF, or Auto Encoder), (4) invoke one or more machine learning models (e.g., as shown in FIG. 11) to produce respective anomaly scores or results, and (5) aggregate the models' scores or results (e.g., using median, mean, or some other type of aggregation technique) to generate an aggregated score for individual observations of processes or hosts.

Figure 23A:
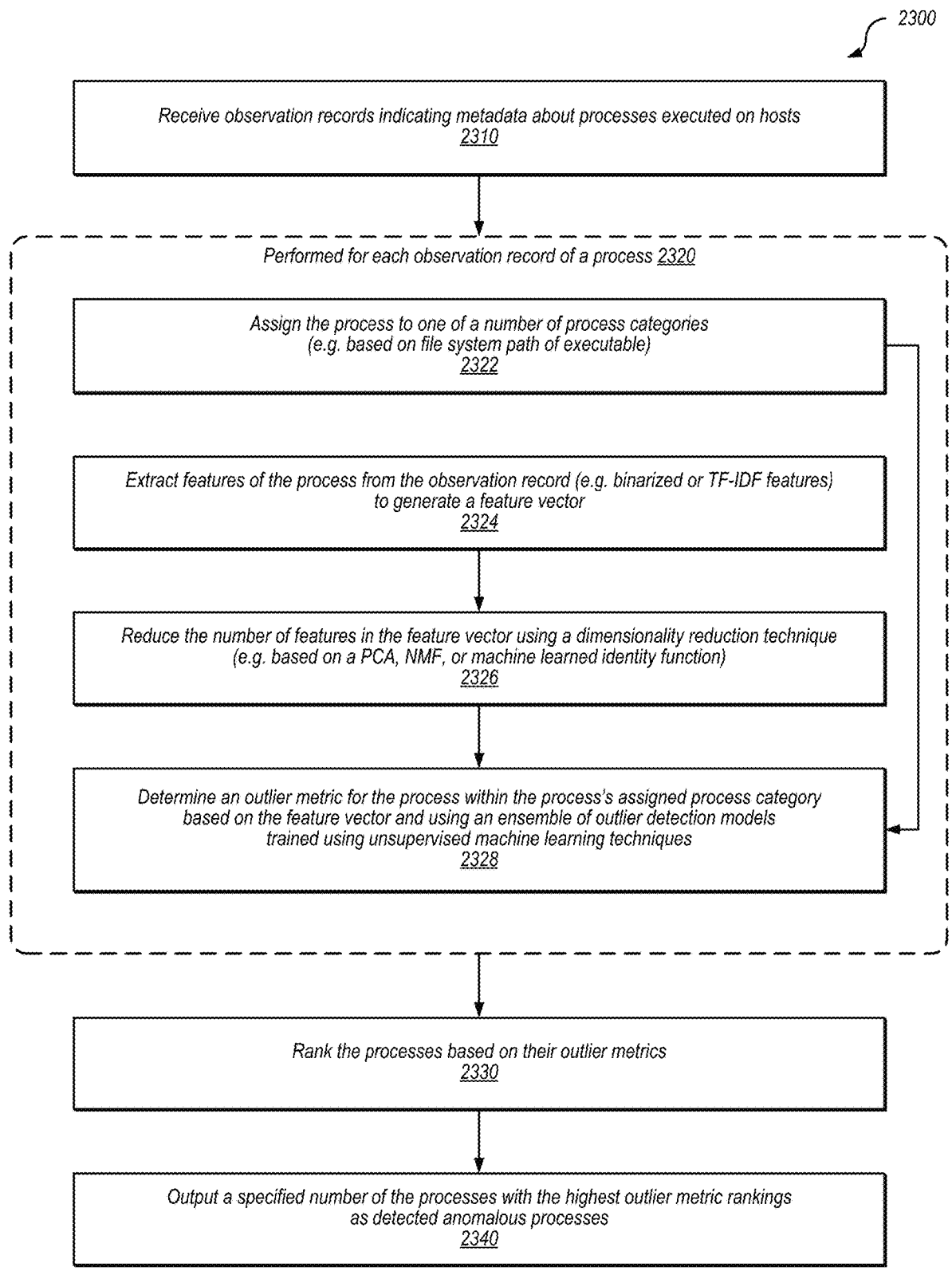
FIGS. 23A and 23B show a flowchart 2300 illustrating a process of detecting anomalous processes and hosts performed by a machine learning anomaly detection system, according to some embodiments.
Figure 23B:
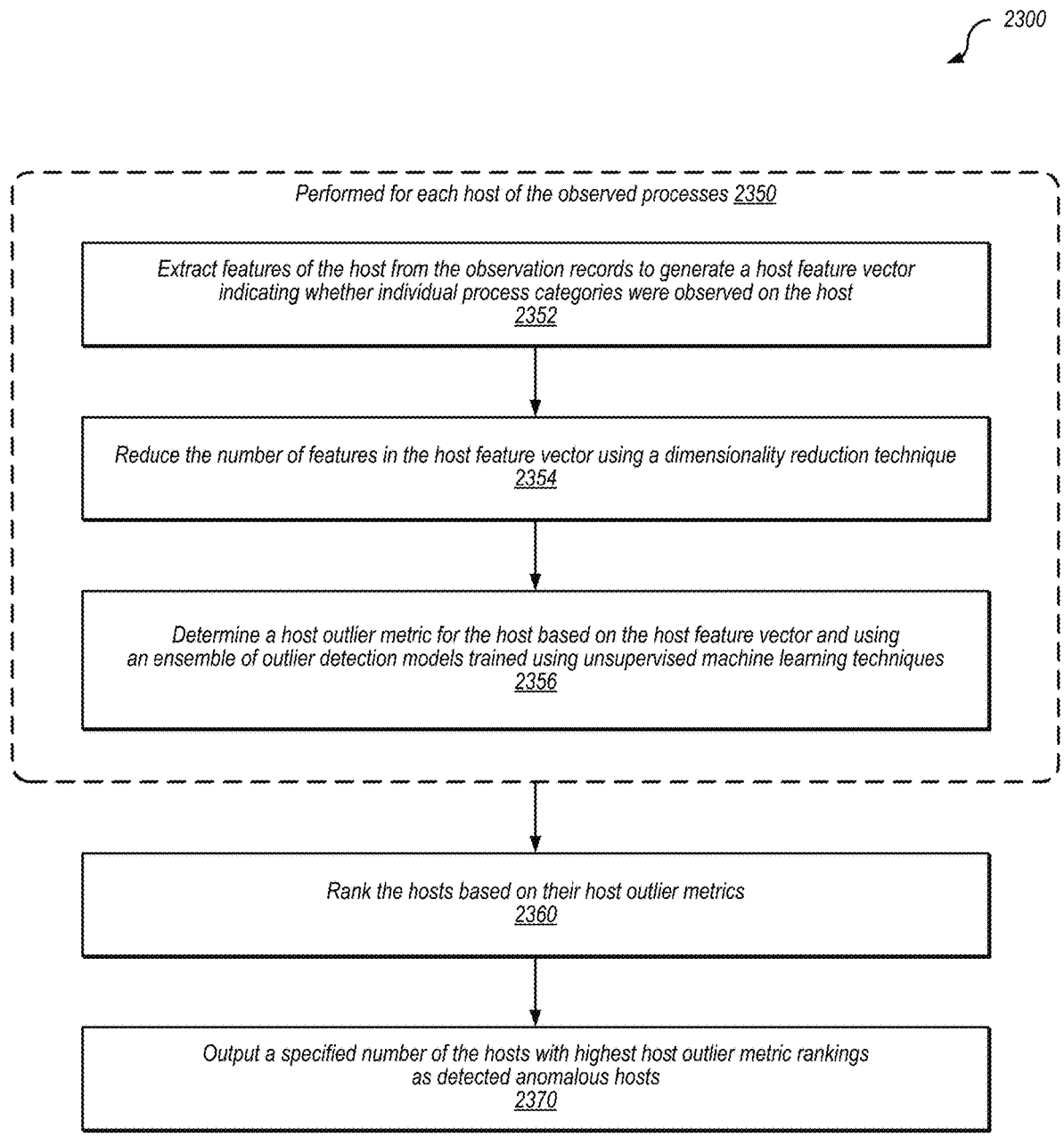

FIGS. 23A and 23B show a flowchart 2300 illustrating a process of detecting anomalous processes and hosts performed by a machine learning anomaly detection system, according to some embodiments. The depicted process may be performed by an embodiment of a machine learning anomaly detection system, as shown for example in FIG. 25 and FIG. 26.

The process begins at operation 2310, where observation records are received. The observation records (e.g. observation record 130 of FIG. 1A) may include metadata about processes that were executed on hosts in a client network monitored by the anomaly detection system. In some embodiments, data collection agents may be deployed on hosts in the client network in order to gather the observation records.

As shown, operations 2322, 2324, 2326, and 2328 are performed 2320 for each observation record associated with an observed process. At operation 2322, the process is assigned to one of a number of process categories (e.g. process categories 120). In some embodiments, each process may be assigned to a category based on the file system path of the executable that was executed by the process. In this manner, all processes assigned to the same category may be processes that executed the same executable or a group of related executables in the same file system directory. In some embodiments, a normalization step may be performed to eliminate irrelevant variations in the naming of the processes, executables, or file system paths. In some embodiments, processes that are assigned to the same category are expected to exhibit similar behavior (e.g. have similar features or attributes), and an outlier process is determined based on other processes in the same category.

At operation 2324, features of the process are extracted from the observation record to generate a feature vector (e.g. feature vector 210 of FIG. 2A). In some embodiments, the feature extraction process may involve augmenting the observation record with additional data from other sources. In some embodiments, a feature vector for a process may encode the process as a document of terms. In a binarized form, the feature vector may include 0s and 1s indicating the absence or presence of individual feature values. In a TF-IDF form, the feature vector may include TF-IDF scores for individual feature values with respect to a corpus of previous observation records. In some embodiments, the generated feature vectors may be compiled into a sparse matrix, such as matrix 200 of FIG. 2A.

At operation 2326, the number of features in the feature vector are reduced using a dimensionality reduction technique. In some embodiments, the dimensionality reduction technique uses a machine learning model that was trained using an unsupervised machine learning technique. In some embodiments, the dimensionality reduction technique may be one or more of PCA, NMF, or an Auto Encoder. The result of the dimensionality reduction operation is an input dataset of smaller feature vectors that are ready for consumption by the outlier detection models.

At operation 2328, the anomaly detection system determines an outlier metric for the process within the process's assigned category based on the feature vector and using an ensemble of outlier detection models trained using unsupervised machine learning techniques. In some embodiments, the individual results of the outlier detection models are aggregated using a weighted average formula, a voting scheme, an aggregator model, or some other aggregation technique. In some embodiments, the outlier detection models in the ensemble may include an Isolation Forest model or a One-Class SVM. In some embodiments, other types of models such as classifiers trained using automatically labeled data may also be used. Example types of classifier models that may be used include Random Forest, XGBoost, K-Nearest Neighbor, and Logistic Regression, Neural Network. In some embodiments, the system may maintain one set of models for each process category. In some embodiments, the system may use the same set of models for multiple process categories.

At operation 2330, the processes are ranked based on their determined outlier metrics. In some embodiments, the outlier metrics of the processes may be normalized so that they can be compared across process categories. For example, a particular process's outlier metric may be normalized to indicate how extreme of an outlier it is within its own category. In some embodiments, all observed processes collected for a given observation period are ranked according to their outlier metrics, so that the highest ranked processes are the most extreme outliers within their respective categories.

At operation 2340, a specified number of processes with the highest outlier metric rankings are selected and outputted as detected anomalous processes. For example, the anomaly detection system may identify the detected anomalous process on a GUI or in an alert. In some embodiments, such output may be used by security analysts at a SOC to assign priority to individual processes or hosts for investigative actions. By outputting only a specified number of anomalous processes, the anomaly detection system does not overwhelm security analysts with a huge volume of anomalies during the hunt process.

FIG. 23B illustrates the building and use of a host feature vector to detect outlier hosts. The depicted process in FIG. 23B may be performed independently or in conjunction with the process outlier detection process of FIG. 23A. In some embodiments, the outlier host detection process may be performed after the process outlier detection process of FIG. 23A.

As shown, operations 2352, 3254, and 2356 in the illustrative process are performed 2350 for each host seen in the observation records. At operation 2352, features of an individual host are extracted from the observation records to generate a host feature vector (e.g. feature vector 240 of FIG. 2B). In some embodiments, the host feature vector will include features of individual process categories, such as whether each individual process category was observed on the host during an observation period. In some embodiments, the host feature vector may include a group of features for each process category (e.g. features 260*a-n* for process category A in FIG. 2B). Depending on the embodiment, such process category features may indicate the number of processes of the category were executed on the host, whether an outlier process was detected in the category, the number of outlier processes that were detected in the category, the total amount of network connections made by processes in the category, the average execution time of processes in the category, among other types of features.

At operation 2354, the number of features in the host feature vector is reduced using a dimensionality reduction technique. In some embodiments, the dimensionality reduction may be performed using a machine learned model that was trained using an unsupervised machine learning technique. Operation 2354 may be performed in a similar manner as operation 2326 of FIG. 23A.

At operation 2356, a host outlier metric is determined for the host based on the host feature vector and using an ensemble of outlier detection models trained using unsupervised machine learning techniques. In some embodiments, the host outlier detection models used by operation 2356 are different from the process outlier detection models of operation 2328. In some embodiments, an outlier host is determined with respect to all hosts in the client network in the historical data. In some embodiments, a host is determined to be an outlier by comparing its feature vector with previous feature vectors collected for the same host. In some embodiments, an outlier host is determined with respect to a category of similar hosts (e.g. similar file servers) and with a specified time period (e.g. within the last month), as configured by administrators of the anomaly detection system. In some embodiments, operation 2356 may be performed in a similar manner as operation 2328 of FIG. 23A.

At operation 2360, the hosts are ranked based on their host outlier metrics. Operation 2360 may be performed in a similar manner as operation 2330 of FIG. 23A for processes. Finally, at operation 2370, a specified number of hosts with the highest host outlier metric rankings are outputted as detected anomalous hosts. Operation 2370 may be performed in a similar manner as operation 2340 of FIG. 23A.

8. Generating Synthetic Anomalies

Machine-learned anomaly detection is a valuable approach for a variety of cybersecurity applications (e.g., identifying unusual traffic, atypical usage of known applications, and the like). However, applying existing or traditional machine learning methods to anomaly detection in cybersecurity is hampered by the lack of labeled anomaly data signals indicative of the wide variety of attack strategies used by attackers. Such data is needed to train or test robust anomaly detection models.

One method to address the lack of truth data is to create synthetic data as a proxy. However, randomly generating synthetic data results in a distribution across the feature space that is uniform, and not at all representative of actual data that may be observed for real-world software processes seen on computing hosts. Moreover, such real-world data is typically very high-dimensional and sparse, making feature space coverage a significant problem with synthetic data generation.

Therefore, to address these technology-related challenges of simulating useful synthetic data in a high-dimensional feature space (e.g., a feature space for managed detection and response (MDR) process data), disclosed herein are methods, systems, and processes of generating synthetic data that preferentially samples points near the lower dimensional manifold where the real data lies. It will be appreciated that this approach may be used to create synthetic data that represents a more realistic set of synthetic datapoints than conventional synthetic data generation techniques.

As noted, in a high dimensional feature space, sampling in a hyper-cube uniformly across all dimensions results in data that is "far" (e.g., from the density point of view) from the manifold on which the real data is observed. This presents a technological problem to security analysts who would like to train machine learning models to detect anomalies. Security analysts would benefit from simulating anomalies that are closer to the manifold where the real data lies. Therefore, in some embodiments, a synthetic data generator (e.g. synthetic data generator 1010 of FIG. 10 or synthetic data generator 2524 of FIG. 25) is implemented to bootstrap from the real data to create synthetic data that contain qualitative anomalies, which are close to the real data as evaluated based on a density function.

In some embodiments, a synthetic data generation process may be implemented to perform at least the following steps: (1) compute the boundary of an observed dataset in a high-dimensional space, with the goal of generating a synthetic dataset that lies near the boundary according to a density function of the observed dataset; (2) generate a candidate synthetic datapoint using a randomly sampled datapoint from the observed dataset (e.g., using the formula $Y=X+\rho \cdot W$, wherein X is the observed datapoint, $\rho$ is a distance or step size from X, and W is a unit step in the hypersphere surrounding X); (3) decide whether to keep the candidate datapoint using the density function (e.g., by generating a random number between 0 and 1 and checking if random number is less than the output of the density function at Y. This process may be performed for a fixed value of ρ and repeated for multiple directions W. Alternatively, this process may be performed for a fixed direction W for different values of ρ. For example, the process may start from a distance ρ=0, and increase the distance until the density falls below a specified threshold (e.g. a desired boundary or density level of the observed dataset).

In some embodiments, another synthetic data generation process may be implemented to perform at least the following steps: (1) fit a density function $\hat{\psi}$ that evaluates a likelihood of being sampled from the manifold of a dataset of real data; (2) estimate a first distance from an observed datapoint using $\hat{\psi}$ that corresponds to a percentile (e.g. 5th percentile) of the output of this function ("delta 1"); (3) repeat steps (1) and (2) for a dataset of uniformly sampled data to estimate a second distance from the observed datapoint that corresponds to a percentile (e.g. 95th percentile) of the output of the second function ("delta 2"), (4) divide the separation between the two distances, delta 1 and delta 2, into equal intervals, (5) estimate the changes in distance that provides uniform steps of changes in density (e.g., by sampling a number of synthetic datapoints between the two distances to determine how the density function(s) are changing with the distance); and (6) using the estimated distances, generate synthetic datapoints between delta 1 and delta 2 until a desired synthetic datapoints at each density level is obtained. In this manner, the foregoing process provides a way of generating a set of synthetic datapoints that are likely to be stratified near the desired boundaries of the observed data.

Figure 24:
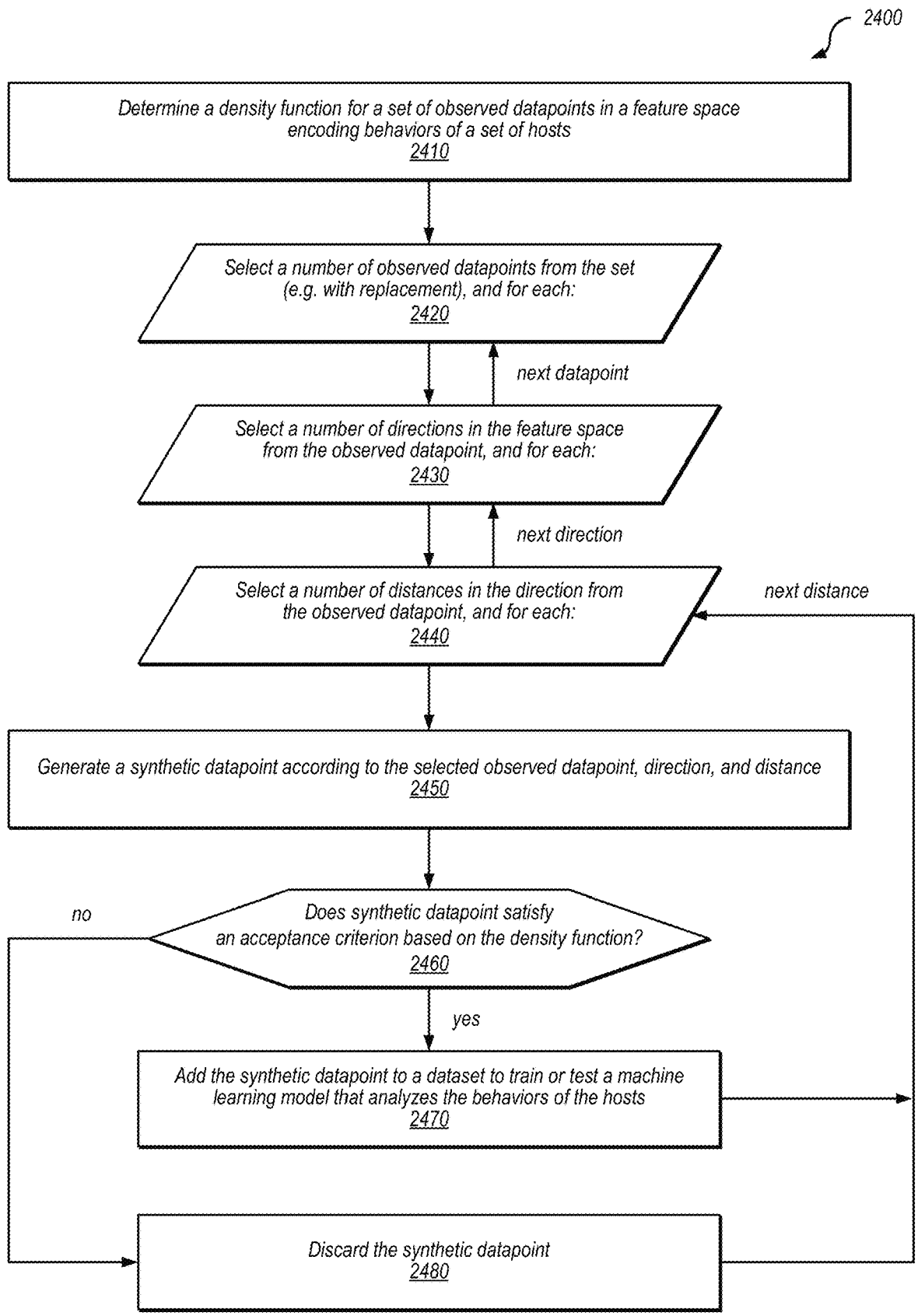
FIG. 24 is a flow chart 2400 illustrating a process performed by a synthetic data generation system to generate synthetic data used to train or test machine learning models in an anomaly detection system, according to some embodiments.

FIG. 24 is a flow chart 2400 illustrating a process performed by a synthetic data generation system to generate synthetic data to train or test machine learning models in an anomaly detection system, according to some embodiments. In some embodiments, the process shown may be performed by a synthetic data generator, such as the synthetic data generator 1010 of FIG. 10 or synthetic data generator 2524 of FIG. 25.

At operation 2410, a density function is determined for a set of observed datapoints in a feature space (e.g. feature space 800 of FIG. 8). In some embodiments, the observed datapoints may encode behaviors of a set of hosts, for example, feature vectors of processes or hosts that are used to train a machine learning model used by an anomaly detection system (e.g. the ML models 1132 of FIG. 11). In some embodiments, the density function may be determined using a density estimation technique such as a Kernel Density Estimator with Gaussian kernels. The density function may be used to determine, for any given datapoint in the feature space, a probability that the datapoint will be observed or sampled in the dataset.

At operation 2420, a number of observation datapoints are selected from the set. In some embodiments, the observed datapoints may be selected with replacement, meaning that the same datapoint may be selected more than once. In some embodiments, the observation datapoints may be selected randomly. In some embodiments, the observation datapoints may be selected using one or more selection criteria (e.g. based on its feature values), which may be controlled via configuration information provided to the system.

As shown, operation 2430 is performed for each observation datapoint selected. At operation 2430, a number of directions in the feature space are selected from a particular observation point. The direction will be used to generate one or more synthetic datapoints in the feature space. In some embodiments, the selected direction may be a feature in the feature vector of the observed datapoint. In some embodiments, the selected direction may be some linear combination of multiple features in the feature vector (e.g., a selected unit vector in the hypersphere around the observed datapoint). In some embodiments, the direction may be selected randomly. In some embodiments, the direction may be selected based on configuration information specified for the system (e.g. based on the location of the observed datapoint relative to the rest of the observed datapoints).

As shown, operation 2440 is performed for each direction selected in operation 2430. At operation 2440, a number of distances are selected in the direction from the observed datapoint. In some embodiments, the distance may be selected at random. In some embodiments, the distances may be constrained by configuration information, for example, to limit the distances to a particular distance range. In some embodiments, the configuration information may specify a probability range, which can be used to calculate the distance range using the density function.

In some embodiments, the range may be bounded by a first probability value calculated using a first density function and a second probability value calculated using a second density function. For example, the distance range for a particular direction may be bounded by the 5th percentile probability of a first density function of the observed dataset, and the 95th percentile probability of a second density function of a dataset of randomly generated synthetic data. In some embodiments, after a distance range is determined, a logistic regression may be performed to estimate the relationship between the distance and one or both of the density functions (e.g. as shown in FIG. 9B). Using this determined relationship, successive synthetic datapoints of increasing distance values may be generated in such a manner that each datapoint corresponds to a uniform decrease in the density function probability value.

As shown, operation 2450 is performed for each distance selected. At operation 2450, a synthetic datapoint (e.g. synthetic datapoint 850 of FIG. 8) is generated according to the selected observed datapoint, the selected direction, and the selected distance. Thus, operations 2420, 2430, 2440, and 2450 may be repeated to generate a large number of synthetic datapoints in the feature space. In some embodiments, the process may successive synthetic datapoints in a particular direction at increasing distances. The generation of the successive datapoint will continue until the density function probability of a datapoint falls below a specified threshold. Though not shown here, in some embodiments, the synthetic datapoint generation process may first select a particular distance, and then select multiple directions with that distance to generate synthetic datapoints. In some embodiments, synthetic datapoints may be generated with a randomly drawn pair of a direction and a distance.

At operation 2460, a check is performed to determine whether the generated synthetic datapoint satisfies an acceptance criterion based on the density function. For example, in some embodiments, the acceptance criterion may require that the synthetic datapoints have a density function probability value that is above or below a certain configured threshold. In some embodiments, the acceptance criterion may include a random component. For example, a synthetic datapoint may be accepted if its density function probability is more than a randomly generated value between 0 and 1.

If the synthetic datapoint satisfies the acceptance criterion, the process proceeds to operation 2470, where the datapoint is added to a dataset that is used to train or test a machine learning model that is used to analyze the behaviors of the hosts. For example, the machine learning model may be a classification model discussed in connection with FIG. 7. In some embodiments, the generated synthetic datapoints may be combined with actually observed datapoints in a single dataset (e.g. dataset 1054 of FIG. 10), where the datapoints are automatically labeled to indicate whether they are observed or synthetic. In some embodiments, such a dataset may be used to train a classification model to distinguish between observed datapoints and synthetic datapoints. In some embodiments, the dataset may also be used as validation or testing data for the classification model.

If the synthetic datapoint does not satisfy the acceptance criterion, the process proceeds to operation 2480, where the synthetic datapoint is discarded. In some embodiments, generated datapoints may be discarded for reasons that are not related to the density function. For example, in some embodiments, the system may discard synthetic datapoints if it is determined that too many synthetic datapoints have been generated in a vicinity of the feature space. In some embodiments, the illustrated process may repeat until a sufficient number of synthetic datapoints have been generated.

9. Evaluating a Model by Generating Patterns, Perturbing Patterns & Injecting Anomalies Anomaly detection applied to managed detection and recovery (MDR) hunt data is a valuable tool for identifying previously unseen types of malicious behavior. Unfortunately, existing algorithms and methodologies are difficult to test quantitatively because they deal with scenarios where labeled ground truth does not exist. Accordingly, in some embodiments of an anomaly detection system, an anomaly detection model evaluator (e.g. model evaluator 2528 of FIG. 25) is used to implement methods, systems, and processes to test the robustness of machine learning models in scenarios most commonly found in MDR hunt data. Hunts analyze individual computing assets and collect data about the (software/computing) processes running (or executing) on the computing assets. To obtain benchmarks for acceptable, adequate, or optimized performance in this context, cases corresponding to the presence of an unusual process, unusual combination or processes, and robustness to noise are accessed for analysis.

In some embodiments, the model evaluator 2528 may be configured to perform at least three functions: (1) access detected/found anomalies, (2) evaluate how sensitive the outlier detection models are to detecting said anomalies, and (3) evaluate or determine how robust the models were in cutting through noise to find the anomalies.

In certain embodiments, the model evaluator 2528 simulates feature vectors of 0s and 1s with n rows and k features. In some embodiments, this step represents a departure from the existing/traditional method of testing anomaly detection using continuous values. For a first scenario, shown in FIG. 14, and in some embodiments, a particular column is zero across all rows, except the anomaly row where it is one. For a second scenario, shown in FIG. 15, and in some embodiments, there is a fixed number of patterns that are preset (e.g., 0111000). In this scenario, and in certain embodiments, the anomaly is a row that is not compatible with the preset patterns. In a third scenario, as shown in FIG. 16, and in some embodiments, uncertainty is added by flipping bits within preset patterns. With this scenario, the model is tested for robustness to noise.

As noted, and in some embodiments, the three scenarios can be combined for more rigorous testing and evaluation. In other embodiments, the false positive rate can be estimated by not adding any anomalies and determining what anomalies the models identify. In certain embodiments, an ensemble approach can be implemented that determines which models are able to identify the same anomalies for a given scenario.

In certain embodiments, the anomaly detection pipeline or model can be modified, trained, evaluated, or tested using mixed scenario analysis, model aggression analysis, and/or anomaly distance analysis to determine the individual and collective performance of various models and other methodologies implemented (in addition to reducing the computational complexity of the pipeline).

In the mixed scenario analysis, it can be beneficial to evaluate the performance of the models with data generated with combinations of scenarios and parameters, as noted above. With each list of different scenarios applied to the models, a variable ($\Phi$) will be outputted for each model, where 1 means a model detected the anomaly and 0 means that the anomaly was not detected. By creating a sampling across many different combinations of scenarios, in certain embodiments, a regression can be run to determine which elements lead to better detection of anomalies.

In the model aggregation analysis, specific anomalies that the algorithms are able to detect across a fixed number of scenarios can be analyzed. The goal here is to determine if and which models identify the same anomalies in a given scenario, thereby strengthening confidence in what looks anomalous when greater than a threshold of algorithms are identifying the same anomalies.

In the anomaly distance analysis, determining how distances of anomalies from normal data affects algorithms' abilities to detect those anomalies is important. For example, greater distance increases changes of identifying the anomalies. In one embodiment, distance can be a newly added feature to be analyzed in the base case, discussed above.

10. Providing an Interpretable Explanation for Model Feature Importance

Machine learning models can output suggestions for what a security analyst should prioritize for further investigation and/or security operations. In order to provide the security analyst with a starting point for where to start investigating, it would be beneficial to provide an explanation of why a process or piece of data was flagged as an anomaly. Accordingly, in some embodiments, an anomaly detection system may implement an anomaly detection model interpreter (e.g. model interpreter 2526 of FIG. 25) that quantifies the effect of each feature individually on the anomaly score.

In certain embodiments, the model interpreter 2526 keeps one feature at a time, suppresses all other features, and determines the anomaly score. When the foregoing step is repeated for each feature, the resulting set of scores provide(s) a way to determine which feature was most anomalous for each process. In this manner, a security analyst can obtain an understanding of which feature is determinant for generating an alert on a detected anomaly, and use this information to begin their investigation.

In some embodiments, the model interpreter 2526 may perform at least the following operational steps: (1) keep/maintain one feature only and reruns or re-executes the anomaly detection pipeline (as shown in FIG. 11) to obtain an anomaly score and (2) repeat step (1) for each feature to obtain the full set of anomaly scores. In some embodiments, the interpretive process treats the set of features as independent. In another embodiment, a linear regression approach is performed by fitting a linear model to the aggregate anomaly score results, and reports features with the highest coefficients.

11. Unsupervised Choice of Dimensionality Reduction and Linear Regression

As noted, anomaly detection on MDR hunt data is plagued by high dimensionality. The number of possible computing and software processes on a given network is enormous and makes outliers much more difficult for algorithms to identify. To reduce the number of dimensions, embodiments of the anomaly detection system may implement an anomaly detection model manager (e.g. model manager 2522 of FIG. 25), which is capable of automatically determining which features retain the most information for anomaly detection.

It is technically challenging to determine the most salient input features in a feature space in an unsupervised machine learning system, where the accuracies of downstream models cannot be measured. Therefore, in certain embodiments, the model manager 2522 is configured to perform at least the following operational steps: (1) for each column, (i) remove the column c, (ii) reduce the matrix to a desired number of columns, (iii) fit a random forest to predict values in c, and (iv) repeat over all columns c to get an average quality; (2) repeat over k to get average metrics for each value of k; (3) repeat for each size of lower dimensions; and (4) speed up and optimize the foregoing process by training a model over k, number of rows, density, and rank.

12. Anomaly Detection Server That Implements an Anomaly Detection Pipeline

FIG. 25 is a block diagram 2500 illustrating an anomaly detection server 2510, according to some embodiments. In some embodiments, the anomaly detection server 2510 may include one or more computer systems configured to perform various tasks associated with the anomaly detection pipeline as discussed in connection with FIG. 11, such as: (1) scheduling different anomaly detection jobs for periodic execution, (2) executing anomaly detection jobs according to pipeline configurations, (3) periodically testing, evaluating, and/or modifying the outlier detection models used by the pipeline, and (4) performing security operations based on the detected anomalies.

As shown in this example, the anomaly detection server 2510 is implemented in a client network 2540, which includes a number of client computing devices (2550a and 2550b) to be monitored by the anomaly detection server. The server 2510 may be any type of physical or virtual computing device, and may implement some of all of the following components: an anomaly detection pipeline manager 2520, a model manager 2522, a synthetic data generator 2524, a model interpreter 2526, a model evaluator 2528, a security operations engine 2530, and a security data manager 2532. Depending on the embodiment, some of these components may be implemented on different hosts (possibly external to the client network 2540), as individual nodes (e.g. virtual machines), or over multiple servers or nodes as part of a distributed system. In some embodiments, some of the components shown may be implemented in a platform-as-a-service network such as AMAZON WEB SERVICES or MICROSOFT AZURE.

In some embodiments, the anomaly detection pipeline manager 2520 is tasked with overseeing and orchestrating the execution of the anomaly detection process for batches of observation data (e.g. observation records 130) collected from the client computing devices 2550. In some embodiments, the pipeline manager 2520 may initiate the collection of the observation records. In some embodiments, the pipeline manager may collect data and/or perform anomaly detection according to a set schedule (e.g. once a week). Anomaly detection may be performed on different sets of machines in a client's network, and the results generated by the detection process (e.g. detected outlier processes or hosts) may be used for a weekly hunt performed by security analysts. In some embodiments, the pipeline manager 2520 may execute individual stages in the pipeline by, for example, launching different processes or jobs to pre-process the observation data, reduce the feature dimensionality of the data, execute the various outlier detection models, and aggregating the models' results, as discussed in connection with FIG. 11. In some embodiments, the pipeline manager 2520 may provide a management or configuration interface to allow certain users to view the progress or status of an execution, and to control various operational parameters of the detection process. In some embodiments, the pipeline manager 2520 may provide a notification interface (e.g. an API or an email interface) to alert security analysts or other computer systems about detected anomalies within the observed data.

In some embodiments, the model manager 2522 is tasked with maintaining the various machine learning models used by the pipeline. In some embodiments, different sets of machine learning models may be maintained for different hosts or host categories within the client network 2540. In some embodiments, the models may be stored in a database, which may be accessed via the security data manager 2532. In some embodiments, the model manager 2522 may be configured to perform or orchestrate periodic training of the models using unsupervised machine learning techniques, as discussed in connection with FIG. 12. In some embodiments, the model manager may maintain successive versions of individual models that were trained using observation data in different time periods, and select a version of the model to use for a particular execution of the pipeline. In some embodiments, the model manager 2522 may also apply various configuration parameters to the models, which may be received via configuration interface 1270 of FIG. 12.

In some embodiments, the security operations engine 2530 may implement various actions to respond to detected cyberattacks, intrusions, breaches, or compromises of the client network 2540. In some embodiments, the security operations engine 2530 may be implemented by many computers that collectively implement the securities operations center (SOC) of a company. In some embodiments, the security operations engine 2530 may implement various reporting interfaces for detected incidents. In some embodiments, the security operations engine 2530 may implement a number of remediation processes or pipelines for responding to detected events, such as to isolate particular parts of the client network or make configuration changes in the network. In some embodiments, the security operations engine 2530 may implement a variety of tools to allow security analysts to more fully investigate a detected anomaly during the hunt process.

In some embodiments, the security data manager 2532 may be used to provide an interface for all data stored by the anomaly detection pipeline. Such data may include, for example, the collected observation data (including historical data collected in previous collection periods), generated synthetic data, the machine learning models, and various configuration and execution metadata associated with the anomaly detection pipeline. In some embodiments, the saved data may also include manual input from security analysts (e.g., the analysts' findings about a particular outlier process or host). Such information may be used to label the stored observation data, which may be used in some cases to perform supervised training of some machine learning models. In some embodiments, such labeled data may indicate that a process is part of a recognized malicious attack. The features of such a process may be archived in a library so that they can be used to easily detect similar processes in future observation data.

As shown in this example, a number of client computing devices 2550 reside in the client network 2540 being monitored by the anomaly detection server 2510. In some embodiments, the client network 2540 may be a virtual network hosted in a platform-as-a-service (PaaS) provider network, such as AMAZON WEB SERVICES, MICROSOFT AZURE, or GOOGLE CLOUD PLATFORM. The client computing devices 2550 may encompass many different types of computing resources, including hosts, workstations, servers, mobile devices, or virtual machines, and the like. In this context, a virtual machine may be an instance of a computer and operating system that is emulated and hosted on a physical virtual machine host. The virtual machine host may implement virtualization hardware and/or software (e.g. a hypervisor) to execute and manage multiple instances of guest operating systems. Example implementations of such virtualization technologies include VMWARE ESX/ESXI, MICROSOFT HYPERV, AMAZON WEB SERVICES, MICROSOFT AZURE, GOOGLE CLOUD PLATFORM.

13. Example Networking Environment

Figure 26:
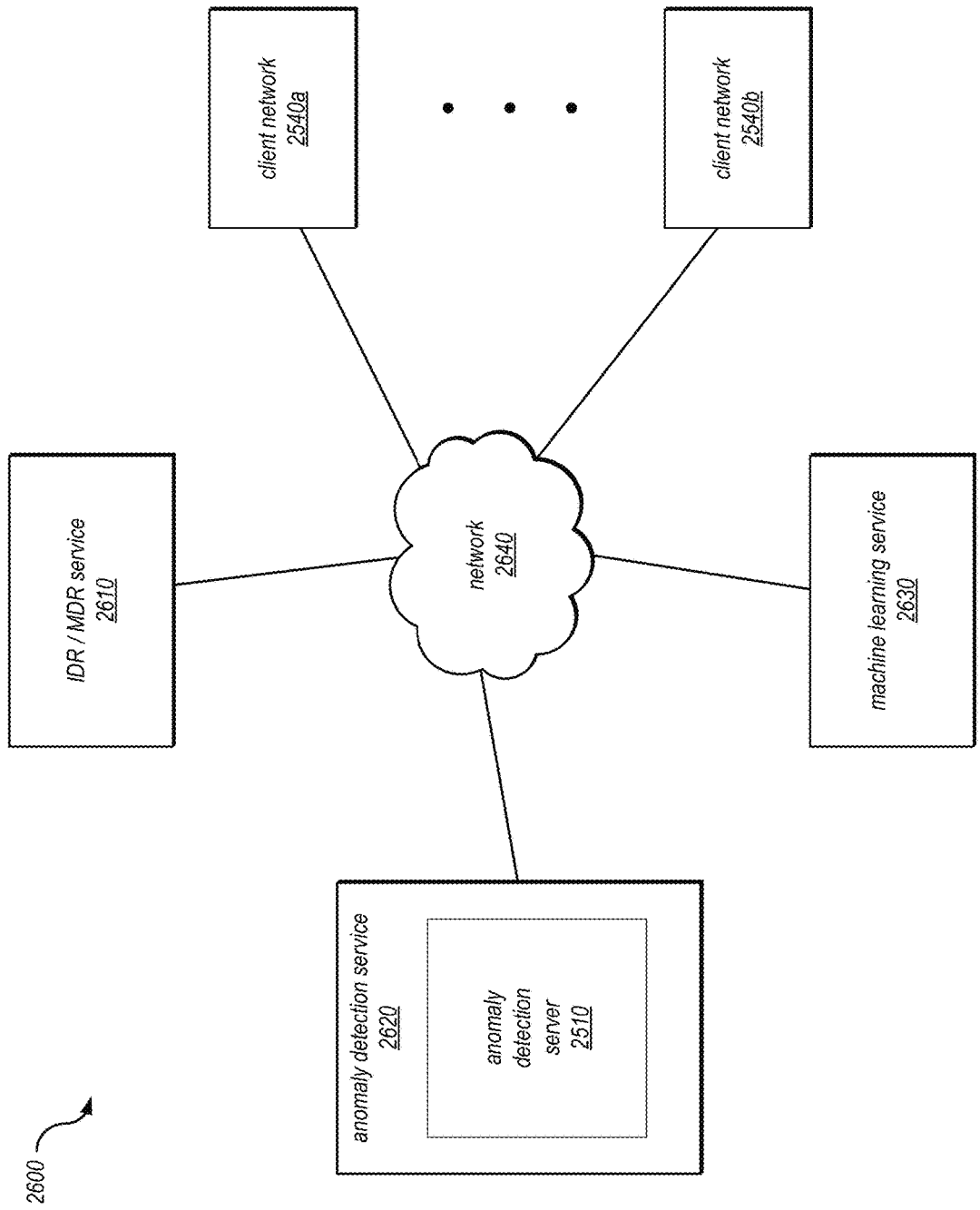
FIG. 26 is a block diagram 2600 of a networked system that implements and uses a machine learning anomaly detection system, according to some embodiments.

FIG. 26 is a block diagram of a networked system, illustrating how an anomaly detection service 2620 is implemented and used using a network 2640.

As shown, the anomaly detection service 2620 is implemented using an anomaly detection server 2510, as discussed in connection with FIG. 25. The anomaly detection service 2620 in this example is communicatively coupled with multiple client computing networks 2540a and 2540b to monitor for anomalies within those networks. The client networks 2540 may be the private networks of different clients, which may be associated with different entities, companies, organizations, groups, geographic locations, etc.

In some embodiments, the anomaly detection service 2620 may be implemented remotely from the client networks 2540. The anomaly detection service 2620 may be configured to collect or receive observation data from the client networks over the network 2640. In some embodiments, the anomaly detection service 2620 may communicate with data collection agents executing on machines in the client networks. The data collection agents may be configured to periodically gather and upload observation data about the client machines to the anomaly detection service. In some embodiments, the observation data may be collected using one or more proxy or an intermediary machines, which may be located in the private network of the client.

In various embodiments, the network 2640 may encompass any suitable combination of networking hardware and protocols necessary to enable communications between the service 2620 and the client networks 2540. In some embodiments, the monitored client devices may execute in a private network of a company, behind a company firewall, and the network 2640 may be a public network such as the Internet, which lies outside the firewall. The network 2640 may encompass the different telecommunications networks and service providers that collectively implement the Internet. In some embodiments, the network 2640 may also include private networks such as private local area networks (LANs), private wide area networks (WANs), or private wireless networks. The network 2640 may be implemented using different hardware (e.g., modems, routers, switches, load balancers, proxy servers, etc.) and software (e.g., protocol stacks, routing software, firewall/security software, etc.) for establishing networking links between the client networks and the anomaly detection service. In some embodiments, communication links between the anomaly detection service 2620 and the client networks 2540 are established using secure communication channels such as transport layer security (TLS) connections.

In some embodiments, the anomaly detection service 2620 may be used by a downstream service such as an incident detection and response (IDR) or managed detection and response (MDR) service provided by a service provider 2610. Such services may be implemented as outsourced services that provide clients with threat hunting services and responds to threats once they are discovered. In some embodiments, IDR and MDR services employs human security analysts to review and investigate detected anomalies from a monitored client network. In some embodiments, some of these anomalies may be identified using the anomaly detection service 2620. In some embodiments, the anomaly detection service 2620 may be implemented as one of a suite of services used or implemented by the IDR/MDR service 2610. In some embodiments, real-time IDR data with a continuous time component can be used by the anomaly detection service in combination with MDR hunt data to perform anomaly detection.

In some embodiments, the anomaly detection service 2620 may be implemented using a machine learning service 2630, which is also accessible via the network 2640. In some embodiments, the machine learning service 2630 may implement a host of features to build and deploy machine learning models and applications. For example, the machine learning service may provide features to allow model developers to experiment with different types of machine learning models, training dataset features, training techniques, etc. In some embodiments, such a service may be used to host a machine learning model or application to be executed based on periodically collected observation data. In some embodiments, the machine learning service may also allow hosted models to be evaluated and retrained using specified model update processes. Examples of such a machine learning service include AWS SAGEMAKER, AZURE MACHINE LEARNING STUDIO, and GOOGLE AUTOML. In some embodiments, the machine learning service 2630 may be hosted in a cloud-based PaaS service provider network. In some embodiments, all or a portion of anomaly detection service 2620, IDR/MDR service 2610, and client networks 2540 may also be hosted in the PaaS service provider network. In some embodiments, some functions provided by services 2610, 2620, or 2630, or the client networks 2540 may be provided through a remote desktop environment provided by the PaaS provider network.

14. Example Computing Environment

Figure 27:
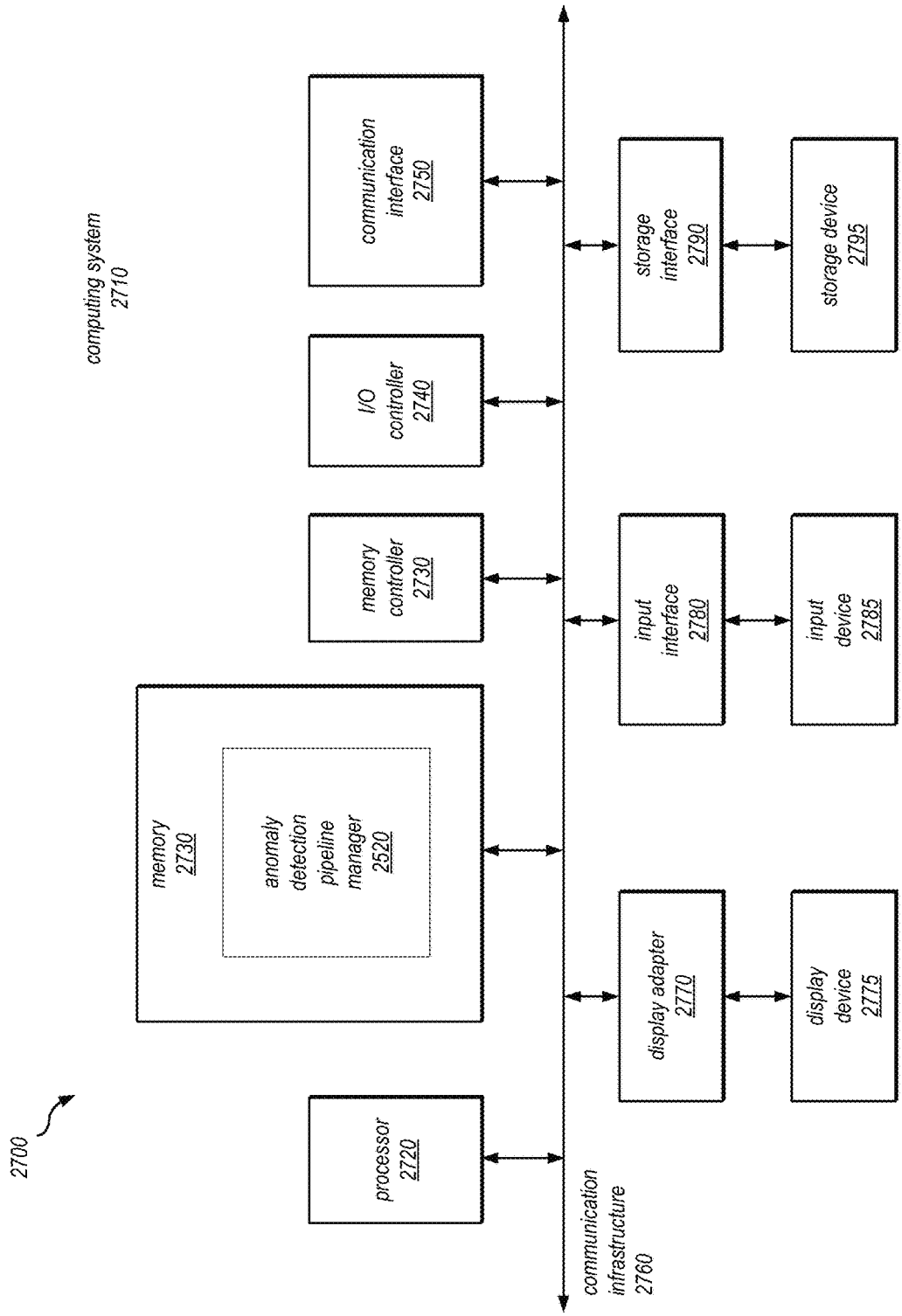
FIG. 27 is a block diagram 2700 of a computing system that may be used to implement one or more portions of a machine learning anomaly detection system, according to some embodiments.

FIG. 27 is a block diagram 2700 of a computing system 2711, which may be used to implement at least a portion of the anomaly detection system or service of FIGS. 25 and 26. For example, computing system 2710 can be used to implement the anomaly detection pipeline manager 2520 of FIG. 25. Computing system 2710 broadly represents a single or multi-processor computing device or system capable of executing computer-readable instructions. Examples of computing system 2710 include, without limitation, any one or more of a variety of devices including workstations, personal computers, laptops, client-side terminals, servers, distributed computing systems, handheld devices, network appliances, storage controllers, and the like. In one configuration, computing system 2710 may include at least one processor 2720 and a memory 2730. By executing the software that implements the anomaly detection pipeline manger 2520, computing system 2710 becomes a special purpose computing device that is configured to perform anomaly detection.

Processor 2720 generally represents any type or form of processing unit capable of processing data or interpreting and executing instructions. In certain embodiments, processor 2720 may receive instructions from a software application or module that may cause processor 2720 to perform the functions of one or more of the embodiments described and/or illustrated herein. For example, processor 2720 may perform and/or be a means for performing all or some of the operations described herein. Processor 2720 may also perform and/or be a means for performing any other operations, methods, or processes described and/or illustrated herein. Memory 2730 generally represents any type or form of volatile or non-volatile storage devices or mediums capable of storing data and/or other computer-readable instructions. Examples include, without limitation, random access memory (RAM), read only memory (ROM), flash memory, or any other suitable memory device. In certain embodiments, computing system 2710 may include both a volatile memory unit and a non-volatile storage device. In one example, program instructions implementing anomaly detection pipeline manager 2520 may be loaded into memory 2730.

In certain embodiments, computing system 2710 may also include one or more components or elements in addition to processor 2720 and/or memory 2730. For example, as shown, computing system 2710 may include a memory controller 2740, an Input/Output (I/O) controller 2740, and a communication interface 2750, each of which may be interconnected via a communication infrastructure. Communication infrastructure 2760 generally represents any type or form of infrastructure capable of facilitating communication between one or more components of a computing device. Examples of communication infrastructure 2760 include, without limitation, a communication bus (such as an Industry Standard Architecture (ISA), Peripheral Component Interconnect (PCI), PCI express (PCIe), or similar bus) and a network.

Memory controller 2730 generally represents any type/form of device capable of handling memory or data or controlling communication between one or more components of computing system 2710. In certain embodiments memory controller 2730 may control communication between processor 2720, memory 2730, and I/O controller 2740 via communication infrastructure 2760, and may perform and/or be a means for performing, either alone or in combination with other elements, one or more of the operations or features described and/or illustrated herein. I/O controller 2740 generally represents any type or form of module capable of coordinating and/or controlling the input and output functions of a computing device. For example, in certain embodiments I/O controller 2740 may control or facilitate transfer of data between one or more elements of computing system 2710, such as processor 2720, memory 2730, communication interface 2750, display adapter 2770, input interface 2780, and storage interface 2790.

Communication interface 2750 broadly represents any type/form of communication device/adapter capable of facilitating communication between computing system 2710 and other devices and may facilitate communication between computing system 2710 and a private or public network. Examples of communication interface 2750 include, a wired network interface (e.g., network interface card), a wireless network interface (e.g., a wireless network interface card), a modem, and any other suitable interface. Communication interface 2750 may provide a direct connection to a remote server via a direct link to a network, such as the Internet, and may also indirectly provide such a connection through, for example, a local area network. Communication interface 2750 may also represent a host adapter configured to facilitate communication between computing system 2710 and additional network/storage devices via an external bus. Examples of host adapters include, Small Computer System Interface (SCSI) host adapters, Universal Serial Bus (USB) host adapters, Serial Advanced Technology Attachment (SATA), Serial Attached SCSI (SAS), Fibre Channel interface adapters, Ethernet adapters, etc.

Computing system 2710 may also include at least one display device 2775 coupled to communication infrastructure 2760 via a display adapter 2770 that generally represents any type or form of device capable of visually displaying information forwarded by display adapter 2770. Display adapter 2770 generally represents any type or form of device configured to forward graphics, text, and other data from communication infrastructure 2760 (or from a frame buffer, as known in the art) for display on display device 2775. Computing system 2710 may also include at least one input device 2785 coupled to communication infrastructure 2760 via an input interface 2780. Input device 2785 generally represents any type or form of input device capable of providing input, either computer or human generated, to computing system 2710. Examples of input device 2785 include a keyboard, a pointing device, a speech recognition device, or any other input device.

Computing system 2710 may also include storage device 2795 coupled to communication infrastructure 2760 via a storage interface 2790. Storage device 2795 generally represents any type or form of storage devices or mediums capable of storing data and/or other computer-readable instructions. For example, storage device 2795 may include a magnetic disk drive (e.g., a so-called hard drive), a floppy disk drive, a magnetic tape drive, an optical disk drive, a flash drive, or the like. Storage interface 2790 generally represents any type or form of interface or device for transmitting data between storage device 2795, and other components of computing system 2710. Storage device 2795 may be configured to read from and/or write to a removable storage unit configured to store computer software, data, or other computer-readable information. Examples of suitable removable storage units include a floppy disk, a magnetic tape, an optical disk, a flash memory device, or the like. Storage device 2795 may also include other similar structures or devices for allowing computer software, data, or other computer-readable instructions to be loaded into computing system 2710. For example, storage device 2795 may be configured to read and write software, data, or other computer-readable information. Storage device 2795 may also be a part of computing system 2710 or may be separate devices accessed through other interface systems.

Many other devices or subsystems may be connected to computing system 2710. Conversely, all of the components and devices illustrated in the figure need not be present to practice the embodiments described and/or illustrated herein. The devices and subsystems referenced above may also be interconnected in different ways from that shown in the figure. Computing system 2710 may also employ any number of software, firmware, and/or hardware configurations. For example, one or more of the embodiments disclosed herein may be encoded as a computer program (also referred to as computer software, software applications, computer-readable instructions, or computer control logic) on a computer-readable storage medium. Examples of computer-readable storage media include magnetic-storage media (e.g., hard disk drives and floppy disks), optical-storage media (e.g., CD- or DVD-ROMs), electronic-storage media (e.g., solid-state drives and flash media), and the like. Such computer programs can also be transferred to computing system 2710 for storage in memory via a network such as the Internet or upon a carrier medium.

The computer-readable medium containing the computer program may be loaded into computing system 2710. All or a portion of the computer program stored on the computer-readable medium may then be stored in memory 2730, and/or various portions of storage device 2795. When executed by processor 2720, a computer program loaded into computing system 2710 may cause processor 2720 to perform and/or be a means for performing the functions of one or more of the embodiments described/illustrated herein. Alternatively, one or more of the embodiments described and/or illustrated herein may be implemented in firmware and/or hardware.

Although the present disclosure has been described in connection with several embodiments, the disclosure is not intended to be limited to the specific forms set forth herein. On the contrary, it is intended to cover such alternatives, modifications, and equivalents as can be reasonably included within the scope of the disclosure.

What is claimed is:

1. A system comprising:
   one or more computing devices that implement an anomaly detection system, configured to:
   receive a plurality of observation records indicating metadata about a plurality of processes executed on hosts in a computer network, wherein individual ones of the observation records indicate (a) an executable executed by a particular process, (b) a digital fingerprint of the executable, and (c) a certificate used to digitally sign the executable;
   for each observation record of a process:
   assign the process to one of a plurality of process categories;
   extract a plurality of features of the process from the observation record to generate a feature vector; and
   process the feature vector using one or more outlier detection models to determine an outlier metric for the process within the process's assigned process category, wherein the one or more outlier detection models are trained using one or more unsupervised machine learning techniques;
   rank processes assigned to an individual process category based on outlier metrics of the processes within the individual process category;
   detect a set of anomalous processes in the individual process category, wherein the set of anomalous processes are a specified number or percentile of processes in the individual process category that have highest outlier metric rankings; and
   output the set of detected anomalous processes.

2. The system of claim 1, wherein the anomaly detection system is implemented as part of a cyberattack monitoring system, configured to:
   periodically collect metadata about the processes executed on the hosts in the computer network and provide the collected metadata to the anomaly detection system; and
   generate a notification identifying the anomalous processes detected by the anomaly detection system as a signal of a potential cyberattack.

3. The system of claim 1, wherein an individual observation record for an individual process indicates one or more of:
   (a) a command line used to launch the individual process,
   (b) a list of network addresses that the individual process connected to,
   (c) one or more software modules loaded by the individual process, and
   (d) one or more digital fingerprints of the one or more software modules loaded by the individual process.

4. The system of claim 1, wherein the anomaly detection system is configured to assign the processes to the process categories based on a file system path of the executable executed by individual ones of the process.

5. The system of claim 1, wherein to extract features from the observation record, the anomaly detection system is configured to generate binary values indicating presence or absence of different feature values in the observation record.

6. The system of claim 1, wherein to extract features from the observation record, the anomaly detection system is configured to generate Term Frequency-Inverse Document Frequency (TF-IDF) values of different feature values in the observation record.

7. The system of claim 1, wherein to generate the feature vector of the process, the anomaly detection system is configured to reduce a number of extracted features of the process using a dimensionality reduction technique, wherein the dimensionality reduction technique is based on one or more of a Principal Component Analysis (PCA), a Non-Negative Matrix Factorization (NMF), or an Auto Encoder.

8. A method comprising:
   performing, by one or more computing devices that implement an anomaly detection system:
   receiving a plurality of observation records indicating metadata about a plurality of processes executed on hosts in a computer network, wherein individual ones of the observation records indicate (a) an executable executed by a particular process, (b) a digital fingerprint of the executable, and (c) a certificate used to digitally sign the executable;
   for each observation record of a process:
   assigning the process to one of a plurality of process categories;
   extracting a plurality of features of the process from the observation record to generate a feature vector; and
   processing the feature vector using one or more outlier detection models to determine an outlier metric for the process within the process's assigned process category, wherein the one or more outlier detection models are trained using one or more unsupervised machine learning techniques;

ranking processes assigned to an individual process category based on outlier metrics of the processes within the individual process category;

detecting a set of anomalous processes in the individual process category, wherein the set of anomalous processes are a specified number or percentile of processes in the individual process category that have highest outlier metric rankings; and outputting the set of detected anomalous processes.

9. The method of claim 8, wherein the assigning of the process to the process category is performed based on a file system path of the executable executed by the process.

10. The method of claim 8, wherein the anomaly detection system uses the same one or more outlier detection models for the process categories but different statistical techniques to determine outlier metrics for different ones of the process categories.

11. The method of claim 8, further comprising performing, by the anomaly detection system:

periodically training the one or more outlier detection models based on newly received observation records using the one or more unsupervised machine learning techniques.

12. The method of claim 8, wherein the one or more outlier detection models comprises an Isolation Forest model or a One-Class Support Vector Machine.

13. The method of claim 8, wherein the determining of the outlier metric comprises combining multiple results produced by a plurality of outlier detection models in an ensemble.

14. The method of claim 13, wherein the ensemble includes a classification model, and the method comprises, periodically:

generating synthetic observation records with synthetic process features;

generating a training dataset that includes the synthetic observation records and actual observation records of processes, wherein the synthetic and actual observation records are labeled automatically; and training the classification model to distinguish between the synthetic and actual observation records.

15. The method of claim 8, further comprising performing, by the anomaly detection system:

generating, based on the observation records, a plurality of host feature vectors for a plurality of hosts that executed the processes, wherein each host feature vector indicates whether individual ones of the process categories were observed on respective hosts according to the observation records;

determining a host outlier metric for each host based on the host feature vectors and using one or more machine learning models trained using the one or more unsupervised machine learning techniques; and outputting one or more of the hosts as detected anomalous hosts based on the host outlier metrics.

16. One or more non-transitory computer-accessible storage media storing program instructions that when executed on or across one or more processors implement an anomaly detection system and cause the anomaly detection system to:

receive a plurality of observation records indicating metadata about a plurality of processes executed on hosts in a computer network, wherein individual ones of the observation records indicate (a) an executable executed by a particular process, (b) a digital fingerprint of the executable, and (c) a certificate used to digitally sign the executable;

cause each observation record of a process to be analyzed, including to:

assign the process to a process category of a plurality of process categories;

extract a plurality of features of the process from the observation record to generate a feature vector; and process the feature vector using one or more outlier detection models to determine an outlier metric for the process within the process's assigned process category, wherein the one or more outlier detection models are trained using one or more unsupervised machine learning techniques;

rank processes assigned to an individual process category based on outlier metrics of the processes within the individual process category;

detect a set of anomalous processes in the individual process category, wherein the set of anomalous processes are a specified number or percentile of processes in the individual process category that have highest outlier metric rankings; and output the set of detected anomalous processes.

17. The one or more non-transitory computer-accessible storage media of claim 16, wherein the program instructions when executed on or across the one or more processors cause the anomaly detection system to assign the processes to the process categories based on a file system path of the executable executed by individual ones of the processes.

18. The one or more non-transitory computer-accessible storage media of claim 16, wherein the program instructions when executed on or across the one or more processors cause the anomaly detection system to:

uses the same one or more outlier detection models for the process categories but different statistical techniques to determine outlier metrics for different ones of the process categories.

19. The one or more non-transitory computer-accessible storage media of claim 16, wherein the program instructions when executed on or across the one or more processors cause the anomaly detection system to:

cause the one or more outlier detection models to be trained based on newly received observation records and using the one or more unsupervised machine learning techniques.

20. The one or more non-transitory computer-accessible storage media of claim 16, wherein the program instructions when executed on or across the one or more processors cause the anomaly detection system to:

generate, based on the observation records, a plurality of host feature vectors for a plurality of hosts that executed the processes, wherein each host feature vector indicates whether individual ones of the process categories were observed on respective hosts according to the observation records;

determine a host outlier metric for each host based on the host feature vectors and using one or more machine learning models trained using the one or more unsupervised machine learning techniques; and output one or more of the hosts as detected anomalous hosts based on the host outlier metrics.

* * * * *